United States Patent
Klasson

(10) Patent No.: US 12,412,041 B2
(45) Date of Patent: Sep. 9, 2025

(54) PRIVACY-PROTECTING PANDEMIC-BIO-SURVEILLANCE MULTI PATHOGEN SYSTEMS

(71) Applicant: Pandemic Insights, Inc., Austin, TX (US)

(72) Inventor: Eric Klasson, Austin, TX (US)

(73) Assignee: Pandemic Insights, Inc., Austin, TX (US)

(*) Notice: Subject to any disclaimer, the term of this patent is extended or adjusted under 35 U.S.C. 154(b) by 0 days.

(21) Appl. No.: 18/622,820

(22) Filed: Mar. 29, 2024

(65) Prior Publication Data

US 2024/0273302 A1 Aug. 15, 2024

Related U.S. Application Data

(63) Continuation of application No. 17/869,692, filed on Jul. 20, 2022, now Pat. No. 11,989,522, which is a
(Continued)

(51) Int. Cl.
*G16H 50/80* (2018.01)
*G06F 16/29* (2019.01)
(Continued)

(52) U.S. Cl.
CPC .............. *G06F 40/30* (2020.01); *G06F 16/29* (2019.01); *G06F 40/56* (2020.01); *G06N 20/00* (2019.01);
(Continued)

(58) Field of Classification Search
CPC ..... H04W 12/03; H04W 4/021; H04W 4/023; G16H 50/80; G16H 10/65
(Continued)

(56) References Cited

U.S. PATENT DOCUMENTS

| | | | |
|---|---|---|---|
| 8,280,414 B1 | 10/2012 | Nourse et al. | |
| 8,866,608 B2 | 10/2014 | Balinski et al. | |
| 9,612,123 B1 | 4/2017 | Levinson et al. | |
| 10,366,791 B1 | 7/2019 | Thiagarajan et al. | |
| 10,665,348 B1 | 5/2020 | Krayer et al. | |

(Continued)

FOREIGN PATENT DOCUMENTS

| | | |
|---|---|---|
| JP | 2006215942 A | 8/2006 |
| JP | 2011248802 A | 12/2011 |

(Continued)

OTHER PUBLICATIONS

"Privacy-Preserving Contact Tracing," Jul. 21, 2020, Apple, Inc., [online] all pages, [Year: 2020]. Retrieved from the Internet via Wayback Archive: <URL: https:// web.archive.org/web/20200717191643/https://covid19.apple.com/contacttracing>.

(Continued)

*Primary Examiner* — William Nealon
(74) *Attorney, Agent, or Firm* — Pillsbury Winthrop Shaw Pittman, LLP

(57) ABSTRACT

Provided is a process, including: obtaining movement transactions without having server-side access to information by which the members of the population undergoing the changes in geolocation indicated by the movement transactions can be identified, either personally or pseudonymously; obtaining for movement transactions corresponding to a designated window of time, geographic-pathogen-risk scores of starting geolocations that include the starting geographic positions; updating for the movement transactions corresponding to the designated window of time, geographic-pathogen-risk scores of the ending geolocations based on both geographic-pathogen-risk scores of the starting geolocations involved in movement transactions ending at the ending geolocations and rates of traffic at the ending geolocations indicated by movement transactions ending or starting at the ending geolocations.

30 Claims, 8 Drawing Sheets

Related U.S. Application Data continuation of application No. 17/382,076, filed on Jul. 21, 2021, now Pat. No. 11,397,861.

(60) Provisional application No. 63/110,860, filed on Nov. 6, 2020, provisional application No. 63/055,243, filed on Jul. 22, 2020.

(51) Int. Cl.

| | |
|---|---|
| *G06F 40/30* | (2020.01) |
| *G06F 40/56* | (2020.01) |
| *G06N 20/00* | (2019.01) |
| *G06Q 10/105* | (2023.01) |
| *G06Q 10/1093* | (2023.01) |
| *G16H 10/60* | (2018.01) |
| *G16H 10/65* | (2018.01) |
| *G16H 15/00* | (2018.01) |
| *G16H 40/20* | (2018.01) |
| *G16H 40/67* | (2018.01) |
| *G16H 50/20* | (2018.01) |
| *G16H 50/30* | (2018.01) |
| *G16H 50/70* | (2018.01) |
| *G16H 80/00* | (2018.01) |
| *H04L 51/222* | (2022.01) |
| *H04W 4/02* | (2018.01) |
| *H04W 4/021* | (2018.01) |
| *H04W 4/029* | (2018.01) |
| *H04W 12/03* | (2021.01) |
| *H04W 12/033* | (2021.01) |
| *G16H 10/20* | (2018.01) |

(52) U.S. Cl.
CPC ....... *G06Q 10/105* (2013.01); *G06Q 10/1093* (2013.01); *G16H 10/60* (2018.01); *G16H 10/65* (2018.01); *G16H 15/00* (2018.01); *G16H 40/20* (2018.01); *G16H 40/67* (2018.01); *G16H 50/20* (2018.01); *G16H 50/30* (2018.01); *G16H 50/70* (2018.01); *G16H 50/80* (2018.01); *G16H 80/00* (2018.01); *H04L 51/222* (2022.05); *H04W 4/021* (2013.01); *H04W 4/023* (2013.01); *H04W 4/025* (2013.01); *H04W 4/029* (2018.02); *H04W 12/03* (2021.01); *H04W 12/033* (2021.01); *G16H 10/20* (2018.01)

(58) Field of Classification Search
USPC ..................................... 455/456.1
See application file for complete search history.

(56) References Cited

U.S. PATENT DOCUMENTS

| | | | |
|---|---|---|---|
| 10,726,359 B1 | 7/2020 | Drouin et al. | |
| 10,803,993 B2 | 10/2020 | Huang | |
| 11,011,277 B1 | 5/2021 | Kelly et al. | |
| 11,164,269 B1 | 11/2021 | Locke et al. | |
| 11,397,861 B2 | 7/2022 | Klasson | |
| 11,586,825 B2 | 2/2023 | Klasson | |
| 11,775,570 B2 | 10/2023 | Wheeler | |
| 11,989,522 B2 | 5/2024 | Klasson | |
| 12,175,195 B2 | 12/2024 | Klasson | |
| 2005/0270311 A1 | 12/2005 | Rasmussen et al. | |
| 2006/0036619 A1 | 2/2006 | Fuerst et al. | |
| 2007/0229290 A1* | 10/2007 | Kahn .................... G16H 50/80 |
| | | | 702/19 |
| 2009/0265106 A1 | 10/2009 | Bearman et al. | |
| 2011/0161116 A1 | 6/2011 | Peak et al. | |
| 2011/0225046 A1 | 9/2011 | Eldering et al. | |
| 2012/0143430 A1 | 6/2012 | Broggi et al. | |
| 2012/0203459 A1 | 8/2012 | Spindler et al. | |
| 2013/0138451 A1 | 5/2013 | Shiono et al. | |
| 2013/0147820 A1 | 6/2013 | Kalai et al. | |
| 2013/0321401 A1 | 12/2013 | Piemonte et al. | |
| 2013/0325979 A1 | 12/2013 | Mansfield et al. | |
| 2013/0328862 A1 | 12/2013 | Piemonte | |
| 2014/0114677 A1 | 4/2014 | Holmes | |
| 2014/0136226 A1 | 5/2014 | Dittmer et al. | |
| 2014/0141803 A1 | 5/2014 | Marti et al. | |
| 2014/0152657 A1 | 6/2014 | Johnston et al. | |
| 2015/0100330 A1* | 4/2015 | Shpits .................... G16H 50/80 |
| | | | 705/2 |
| 2015/0300823 A1 | 10/2015 | Kahn et al. | |
| 2015/0371347 A1 | 12/2015 | Hayward | |
| 2016/0117937 A1 | 4/2016 | Penders et al. | |
| 2016/0180060 A1* | 6/2016 | Nelson .................... H04L 67/12 |
| | | | 702/19 |
| 2016/0196577 A1 | 7/2016 | Reese et al. | |
| 2016/0203522 A1 | 7/2016 | Shiffert et al. | |
| 2016/0224803 A1 | 8/2016 | Frank et al. | |
| 2017/0024531 A1* | 1/2017 | Malaviya ............... G16H 50/30 |
| 2017/0039339 A1 | 2/2017 | Bitran et al. | |
| 2017/0123421 A1 | 5/2017 | Kentley et al. | |
| 2017/0162197 A1 | 6/2017 | Cohen | |
| 2017/0173262 A1 | 6/2017 | Veltz | |
| 2017/0178037 A1 | 6/2017 | Kaye et al. | |
| 2017/0209102 A1* | 7/2017 | Parthasarathy ...... A61B 5/0059 |
| 2017/0316324 A1 | 11/2017 | Barrett et al. | |
| 2017/0351834 A1 | 12/2017 | Cahan et al. | |
| 2017/0352119 A1* | 12/2017 | Pittman .................. G16H 50/80 |
| 2018/0052970 A1 | 2/2018 | Boss et al. | |
| 2018/0308585 A1 | 10/2018 | Holmes et al. | |
| 2019/0015736 A1* | 1/2019 | Han ...................... A63F 13/214 |
| 2019/0098599 A1 | 3/2019 | Dixon | |
| 2019/0226868 A1 | 7/2019 | Hazrati et al. | |
| 2019/0252078 A1* | 8/2019 | Schubert ............... G06N 3/044 |
| 2019/0373405 A1 | 12/2019 | Jones et al. | |
| 2020/0004746 A1* | 1/2020 | Randall .................. G16H 70/60 |
| 2020/0028735 A1 | 1/2020 | Schlosberg et al. | |
| 2020/0105418 A1 | 4/2020 | Mei et al. | |
| 2020/0134103 A1 | 4/2020 | Mankovskii | |
| 2020/0176125 A1 | 6/2020 | Chatterjea et al. | |
| 2020/0244716 A1 | 7/2020 | Mehta et al. | |
| 2020/0334737 A1 | 10/2020 | Miller | |
| 2020/0335226 A1 | 10/2020 | Hara et al. | |
| 2020/0336450 A1 | 10/2020 | Gao et al. | |
| 2021/0020294 A1 | 1/2021 | Bharmi et al. | |
| 2021/0045362 A1* | 2/2021 | Gritzman ............. A01K 29/005 |
| 2021/0073736 A1 | 3/2021 | Alawi et al. | |
| 2021/0074436 A1 | 3/2021 | Trim et al. | |
| 2021/0090750 A1 | 3/2021 | Sadilek et al. | |
| 2021/0092796 A1 | 3/2021 | Kumar et al. | |
| 2021/0125732 A1 | 4/2021 | Patel et al. | |
| 2021/0209055 A1 | 7/2021 | Winston et al. | |
| 2021/0215610 A1 | 7/2021 | Robertson et al. | |
| 2021/0215693 A1 | 7/2021 | Amiel | |
| 2021/0216677 A1 | 7/2021 | Santarone et al. | |
| 2021/0241879 A1 | 8/2021 | Haggerty et al. | |
| 2021/0280320 A1 | 9/2021 | Arora et al. | |
| 2021/0306797 A1* | 9/2021 | Johnson ................. H04W 4/12 |
| 2021/0313073 A1* | 10/2021 | McSchooler .......... G16H 50/80 |
| 2021/0313074 A1* | 10/2021 | Mesirow ................ H04W 4/029 |
| 2021/0327595 A1* | 10/2021 | Abdallah ............ A61B 5/02055 |
| 2021/0337355 A1 | 10/2021 | Sobol et al. | |
| 2021/0375440 A1 | 12/2021 | Schlameuss et al. | |
| 2022/0027565 A1 | 1/2022 | Klasson | |
| 2022/0028557 A1 | 1/2022 | Klasson | |
| 2022/0028561 A1 | 1/2022 | Klasson | |
| 2022/0028562 A1 | 1/2022 | Klasson | |
| 2022/0028563 A1 | 1/2022 | Klasson | |
| 2022/0030382 A1 | 1/2022 | Klasson | |
| 2022/0285036 A1* | 9/2022 | Merjanian .............. G16H 50/80 |
| 2023/0082658 A1 | 3/2023 | Klasson | |

FOREIGN PATENT DOCUMENTS

| | | |
|---|---|---|
| JP | 2012198717 A | 10/2012 |
| JP | 2014186447 A | 10/2014 |
| JP | 2015161987 A | 9/2015 |
| JP | 2016184196 A | 10/2016 |

(56) References Cited

FOREIGN PATENT DOCUMENTS

| | | |
|---|---|---|
| JP | 2020027610 A | 2/2020 |
| KR | 101733652 B1 | 5/2017 |
| KR | 101885031 B1 | 8/2018 |
| WO | 2013120199 A1 | 8/2013 |
| WO | 2017123905 A1 | 7/2017 |
| WO | 2020012886 A1 | 1/2020 |
| WO | 2020031599 A1 | 2/2020 |

OTHER PUBLICATIONS

Aubrey, Allison, et al., "Green, Yellow, Orange or Red? This New Tool Shows COVI D-19 Risk in Your County," Jul. 1, 2020, [online], 5 pages, [Year 2020]. Retreived from the Internet: <URL: https://www.npr.org/sections/health-shots/2020/07/01/885263658/green-yel low-orange-or-red-this-new-tool-shows-covi d-19-risk-in-your-county>.

Wang, Bowen, et al., "Risk-Aware Identification of Highly Suspected COVID-19 Cases in Social IoT: A Joint Graph Theory and Reinforcement Learning Approach," in IEEE Access, [online], vol. 8, 7 pages, [Year 2020]. Retreived from the Internet: < URL: https://ieeexplore.ieee.org/stamp/stamp.jsp?tp=&arnumber=9121230><DOI: 10.1109/ACCESS.2020.3003750>.

Bambauer, Jane, et al., "COVID-19 Apps are Terrible—They Didn't Have to Be," [online], Nov. 2020, 32 pages. Retrieved from the Internet: <URL: https://s3.documentcloud.org/documents/20424830/bambauer-and-ray-final-2.pdf>.

Brodsky, Isaac, "H3: Uber's Hexagonal Hierarchical Spatial Index," Uber Blog, [online], Jun. 27, 2018, 11 pages. Retrieved from the Internet: <URL: https://eng.uber.com/h3/>.

Chen, Tianqi, et al., "XGBoost: A Scalable Tree Boosting System", In Proceedings of the 22nd ACM SIGKDD International Conference on Knowledge Discovery and Data Mining (KDD '16), Association for Computing Machinery, [online], New York, NY, USA, Aug. 13, 2016, pp. 785-794. Retrieved from the Internet: <URL: https://dl.acm.org/doi/pdf/10.1145/2939672.2939785><DOI:https://doi.org/10.1145/2939672.2939785>.

Du, Peijun, et al., "Advances of Four Machine Learning Methods for Spatial Data Handling: a Review," Journal of Geovisualization and Spatial Analysis [online] 4:13, 2020, 25 pages. Retrieved from the Internet: <URL: https://link.springer.com/article/10.1007/s41651-020-00048-5><DOI:https://doi.org/10.1007/s41651-020-00048-5>.

Final Office Action for related U.S. Appl. No. 17/381,932, issued Jul. 5, 2024, 40 pages.

Final Office Action for related U.S. Appl. No. 17/382,067, issued Mar. 21, 2024, 63 pages.

Final Office Action for related U.S. Appl. No. 17/381,937, issued Nov. 18, 2024, 24 pages.

Final Office Action for related U.S. Appl. No. 17/381,954, issued Feb. 28, 2022, 73 pages.

Final Office Action for related U.S. Appl. No. 17/381,956, issued on Mar. 25, 2022, 49 pages.

Hughes, Eli, "An Introduction to Interrupts," YouTube [online], 2013, 3 pages, all video (runtime 14:06), all transcript. Retrieved from the Internet: <URL: https://www.youtube.com/watch?v=jMnuQMYR3Ro>.

International Search Report and Written Opinion for related International Patent Application PCT/US2021/042817, issued Nov. 11, 2021, 10 pages.

International Search Report and Written Opinion for related International Patent Application PCT/US2021/042820, issued Nov. 18, 2021, 12 pages.

International Search Report and Written Opinion for related International Patent Application PCT/US2021/042821, issued Nov. 16, 2021, 10 pages.

International Search Report and Written Opinion for related International Patent Application PCT/US2021/042822, issued Nov. 16, 2021, 9 pages.

International Search Report and Written Opinion for related International Patent Application PCT/US2021/042826, issued Nov. 16, 2021, 8 pages.

International Search Report and Written Opinion for related International Patent Application PCT/US2021/042827, issued Nov. 11, 2021, 9 pages.

Internet Archive of S2 Cells [online], Jul. 2, 2020, 27 pages. Retrieved from the Internet Web Archive: <URL: https://s2geometry.io/devguide/s2cell_hierarchy.html>.

Jin, et al., "Individual and community-level risk for COVID-19 mortality in the United States," Nature Medicine [online], vol. 27, Feb. 2021, pp. 264-269. Retrieved from the Internet: <URL: https://www.nature.com/articles/s41591-020-01191-8>.

Kazinnik, Roman, "Beyond DAG: Introducing Cyclic Graphs in Neural Networks," [online], Apr. 10, 2018, 4 pages. Retrieved from the Internet: <URL: https://www.romankazinnik.com/post/extending-deep-learning-physically-constrained-gradient-descent>.

Kissick, Chas et al., "What Ever Happened to Digital Contact Tracing?" Lawfare Blog, [online], Jul. 21, 2020, 9 pages. Retrieved from the Internet: <URL: https://www.lawfareblog.com/what-ever-happened-digital-contact-tracing>.

Landau, Susan, "Lessons from Contact-Tracing and Exposure-Notification Apps," Lawfare Blog, [online] May 26, 2021, 5 pages. Retrieved from the Internet: <URL: https://www.lawfareblog.com/lessons-contact-tracing-and-exposure-notification-apps>.

Non-Final Office Action for related U.S. Appl. No. 17/381,932, issued Dec. 21, 2023, 53 pages.

Non-Final Office Action for related U.S. Appl. No. 17/381,937, issued Mar. 14, 2024, 49 pages.

Non-Final Office Action for related U.S. Appl. No. 17/382,067, issued Sep. 8, 2023, 85 pages.

Non-Final Office Action for related U.S. Appl. No. 17/381,932, issued Nov. 21, 2024, 31 pages.

Non-Final Office Action for related U.S. Appl. No. 17/382,076, issued Dec. 7, 2021, 14 pages.

Non-Final Office action for related U.S. Appl. No. 17/381,954, issued Nov. 8, 2021, 58 pages.

Non-Final Office action for related U.S. Appl. No. 17/381,956, issued Dec. 17, 2021, 50 pages.

Notice of Allowance for related U.S. Appl. No. 17/381,956, issued Oct. 14, 2022, 9 pages.

Notice of Allowance for related U.S. Appl. No. 17/382,067, issued Oct. 16, 2024, 18 pages.

Notice of Allowance for related U.S. Appl. No. 17/382,076, issued Mar. 21, 2022, 7 pages.

Notice of Allowance for related U.S. Appl. No. 17/869,692, issued Dec. 29, 2023, 9 pages.

U.S. Appl. No. 17/381,932, filed Jul. 21, 2021, titled Natural-Language Text Generation With Pandemic-Bio-Surveillance Multi Pathogen Systems, 106 pages.

U.S. Appl. No. 17/381,937, filed Jul. 21, 2021, titled Enriching Geographic-Information Systems With Geolocation Attributes To Enhance Accuracy of Pandemic-Bio-Surveillance Multi Pathogen Systems, 104 pages.

U.S. Appl. No. 17/381,954, filed Jul. 21, 2021, titled Personal and Corporate Pathogen-Risk Assessment With Pandemic-Bio-Surveillance Multi Pathogen Systems, 107 pages.

U.S. Appl. No. 17/381,956, filed Jul. 21, 2021, titled Geolocation Pathogen-Risk Assessment With Pandemic-Bio-Surveillance Multi Pathogen Systems, 112 pages.

U.S. Appl. No. 17/382,067, filed Jul. 21, 2021, titled Behavior-Modification Messaging With Pandemic-Bio-Surveillance Multi Pathogen Systems, 108 pages.

U.S. Appl. No. 17/382,076, filed Jul. 21, 2021, titled Privacy-Protecting Pandemic-Bio-Surveillance Multi Pathogen Systems, 108 pages.

Williamson, et al., "Factors associated with COVID-19-related death using OpenSAFELY," Nature [online], 430, vol. 584, Aug. 20, 2020, 17 pages. Retrieved from the Internet: <URL: https://www.nature.com/articles/s41586-020-2521-4>.

Yasuaki et al., "Project Covid19Radar," GitHub [online], Jul. 2, 2020, 10 pages. Retrieved from the Internet Wayback Archive: <URL: https://github.com/Covid-19Radar>.

(56) References Cited

OTHER PUBLICATIONS

Examiner's Answer for related U.S. Appl. No. 17/381,954, issued Apr. 18, 2023, 10 pages.
Decision on Appeal for related U.S. Appl. No. 17/381,954, issued Nov. 22, 2024, 16 pages.
International Preliminary Report on Patentability for related International Patent Application PCT/US2021/042817 issued on Feb. 2, 2023, 7 pages.
International Preliminary Report on Patentability in related International Patent Application PCT/US2021/042820 issued Feb. 2, 2023, 7 pages.
International Preliminary Report on Patentability in related International Patent Application PCT/US2021/042821 issued Feb. 2, 2023, 7 pages.
International Preliminary Report on Patentability in related International Patent Application PCT/US2021/042822 issued Feb. 2, 2023, 5 pages.
International Preliminary Report on Patentability in related International Patent Application PCT/US2021/042826 issued Feb. 2, 2023, 5 pages.
International Preliminary Report on Patentability in related International Patent Application PCT/US2021/042827 dated Feb. 2, 2023, 6 pages.

\* cited by examiner

PRIVACY-PROTECTING PANDEMIC-BIO-SURVEILLANCE MULTI PATHOGEN SYSTEMS

CROSS-REFERENCE TO RELATED APPLICATIONS

This patent application is a continuation of U.S. Non-Provisional patent application Ser. No. 17/869,692, filed 20 Jul. 2022, titled PRIVACY-PROTECTING PANDEMIC-BIO-SURVEILLANCE MULTI PATHOGEN SYSTEMS, which is a continuation of U.S. Non-Provisional patent application Ser. No. 17/382,076, filed 21 Jul. 2021, titled PRIVACY-PROTECTING PANDEMIC-BIO-SURVEILLANCE MULTI PATHOGEN SYSTEMS, now issued as U.S. Pat. No. 11,397,861, which claims the benefit of U.S. Provisional Patent Application No. 63/110,860, filed 6 Nov. 2020, titled GEOLOCATION-BASED INFECTION-RISK ASSESSMENT AND BEHAVIOR MODIFICATION SYSTEM, and U.S. Provisional Patent Application No. 63/055,243, filed 22 Jul. 2020, titled GEOLOCATION-BASED INFECTION-RISK ASSESSMENT AND BEHAVIOR MODIFICATION SYSTEM. The entire content of each afore-listed, earlier-filed application is hereby incorporated by reference for all purposes.

BACKGROUND

1. Field

The present disclosure generally relates to distributed computing applications and, more particularly, to pandemic-surveillance systems.

2. Description of the Related Art

The need for robust, privacy-friendly pandemic-surveillance systems has been recently highlighted by coronavirus disease 2019 (COVID-19), which is primarily transmitted between people in close contact, including via human movement and airborne transmission. Other pathogens are transmitted in a similar manner, and it is expected that future pandemics and other, less-severe outbreaks will give rise to a similar need, in some cases with other modes of transmission driving spread of the pathogen at issue.

SUMMARY

The following is a non-exhaustive listing of some aspects of the present techniques. These and other aspects are described in the following disclosure.

Some aspects include a process, including: obtaining movement transactions without having server-side access to information by which the members of the population undergoing the changes in geolocation indicated by the movement transactions can be identified, either personally or pseudonymously; obtaining for movement transactions corresponding to a designated window of time, geographic-pathogen-risk scores of starting geolocations that include the starting geographic positions; updating for the movement transactions corresponding to the designated window of time, geographic-pathogen-risk scores of the ending geolocations based on both geographic-pathogen-risk scores of the starting geolocations involved in movement transactions ending at the ending geolocations and rates of traffic at the ending geolocations indicated by movement transactions ending or starting at the ending geolocations.

Some aspects include a tangible, non-transitory, machine-readable medium storing instructions that when executed by a data processing apparatus cause the data processing apparatus to perform operations including the above-mentioned process.

Some aspects include a system, including: one or more processors; and memory storing instructions that when executed by the processors cause the processors to effectuate operations of the above-mentioned process.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
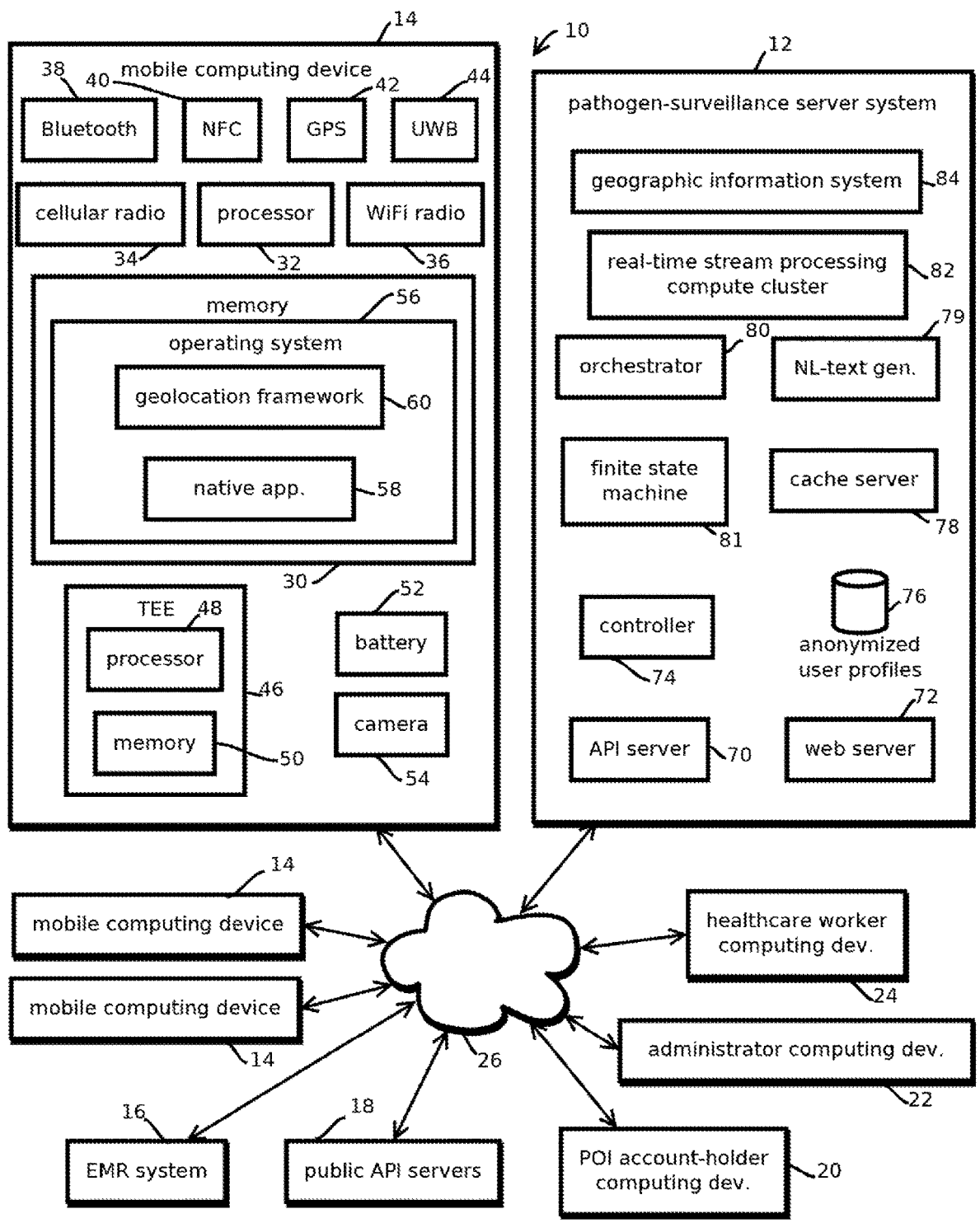
FIG. 1 is a logical and physical architecture block diagram of a computing environment in which a pandemic-surveillance system in accordance with some embodiments may be implemented.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the fields of biosurveillance, pandemic management, public health, neuropsychology, health analytics, public safety, computer science, and national security. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Today, people often have no way of understanding their individual risk of pathogen infection or death during a pandemic based on their personal health profile and their movement decisions related to where they live, work, worship, attend school, shop, or travel. Organizations, corporations, and government agencies often have no way of assessing supply chain risk, the risk of pathogen infection within their individual workplace communities (e.g., employees, contractors, customers, students, or visitors), or how to make remote versus onsite work decisions using data science. Public health agencies are looking for new insights into effective pandemic practices from new public health and biosurveillance digital technologies across the consumer, corporate, non-profit, and federal sectors to drive public health policy decisions.

Many types of software for assessing COVID-19 (or any pathogens and pathogenic) risk leak information that users would prefer to keep private, e.g., with certain types of contact tracing native applications. Further, such applications generally only provide a back-ward looking assessment, indicating that a person might have been exposed in the past. These existing approaches generally do not provide actionable information that users may use to intervene to reduce their COVID-19 risk (or other forms of infections). (None of which is to suggest that systems that produce backward looking assessments or do not provide actional information are disclaimed.)

The need for the present techniques has been highlighted by recent events. A single virus can trigger a global pandemic though a single action: human movement. COVID-19 was able to infect people in 167 countries worldwide in matter of months due to global human movement of infected people.

Government solutions have not proven to be ideal. As COVID-19 reached certain infection and death thresholds, governments mandated forced shelter-in-place restrictions. These restrictions did cause infection and death rate to fall, because human movement was suspended. Given the premise that a virus spreads through human movement, when human movement is suspended, the virus can no longer infect new people. A good thing for sure. But with consequences.

This phenomenon left many populations subject to the Teeter Totter Dilemma: on one end of a Teeter Totter is a Virus Free World. On the other end is a Robust Global Economy. With a government lockdown, the Virus Free World side of the Teeter Totter moves to the ground and the goal of reducing infections and deaths is accomplished. However, the other side of the Teeter Totter has now escalated to extreme heights where workers lose jobs, renters can't pay rent, parents can't feed children, companies lose money or end up bankrupt. To make matters worse, a pandemic attacked the small business owner and not large, international technology companies. When analysts look at ownership of many small businesses, they see underserved communities, communities of color, and people not financially well-off. A pandemic attacks the economic foundations of minorities, the poor, the elderly, and the underserved at disproportionate levels. This is a greatest form of Economic Discrimination ever seen by the World.

To make a bad situation worse, the virus does the same when these communities experience viral exposure—experiencing infection and death rates at 3 to 5 times the level seen in white and wealthy communities. Today, the two sides of the Teeter Totter are in direct conflict with each other.

Presently, governments address the Virus Free World goal by restricting or banning human movement. When this occurs, lives are saved at the cost of massive economic disruption. Alternatively, governments address the Robust Global Economy by removing restrictions and banns on human movement. When this goal is implemented, economies flourish at the cost of loss of human life and the related mental health issues experienced by billions of people. Today, the goals of a Virus Free World and a Robust Global Economy are seemingly at odds. Now a solution is believed to exists that allows both goals to be jointly achieved.

Some embodiments implement a suite of techniques referred to as "Pandemic Insights Roamwell Solution," which in come instantiations removes this conflict so people can remain mindfully mobile while reducing infection and death rates. By using Smart Movement technologies in the form Mobile, SaaS and DaaS solutions-people can remain mobile while reducing infection and death rates. Roamwell, in some embodiments, creates dynamic Personal Risk Indexing, dynamic Location Risk Indexing and dynamic Behavior Modification Messaging to guide a person's, a company's, and a government's movement decisions, all with the singular goal of reducing infection and death rates. And when Roamwell is deployed in over 180 countries, including a free mobile app and a free multi-pathogen personal risk index deployed in various electronic health record systems, the virus driven economic discrimination is expected to decline and hopefully end, allowing people everywhere to prosper, including those most at risk economically.

Embodiments may implement global public health preventive technologies to reduce infection rates and death rates during pandemics and naturally occurring virus cycles, including the following:

a. MOBILE APPLICATION: EMPOWERING HUMAN MOBILITY DECISIONS i. The Mobile App, in some embodiments, includes three features: Personal Risk Index, Location Risk Indexes for any location in the world (or a subset thereof), and Behavior Modification Suggestions based on a User's movement patterns. Each of these three features may include a dynamic capability and may be interactive. Based on a User's location movement and behavior patterns, each of these features may change with the unified goal of reducing a User's risk of virus exposure and infection by changing their movement behavior.

ii. In some embodiments, the Mobile App predicts the daily risk of infection exposure for any person visiting or working in any home, building, facility, or unique location in the world. The Mobile App may create a location-based risk index for each place the User visits. With this service, Users are expected to be able to make intelligent, fact-based movement decisions during a pandemic in order to reduce their risk of infection and death, and the spread of COVID-19 (or any other virus or pathogen). Risk Index forecasts may also be created for any location a User or family member may visit in the future using various public pandemic forecast models.

iii. Based on a User's individual movement patterns (e.g., number of places visited, time spent at each location, the arrival time for each location, and risk index for each of the locations visited), the Mobile App may deliver behavior modification suggestions to each User. Depending on whether the User follows the behavior modification suggestions, in some embodiments, the Mobile App delivers changing suggestions designed to increase the likelihood of modifying the Users behavior to lower-risk movement patterns.

b. SOFTWARE-AS-A-SERVICE: EMPOWERING ECONOMIC STABILITY AND WORKPLACE SAFETY DURING PANDEMICS i. In some embodiments, the SaaS solution reduces a) the risk of infection for each facility based on where the facility employees live and b) the risk of end-to-end supply chain disruptions during pandemics. Some embodiments of the SaaS solution are designed for corporations, government agencies, and non-profits so they can analyze facility, employee, customer, and supply chain exposure risks. SaaS, in some cases, integrates demographic and virus data with anonymized employee HR data to create a Facility Risk Index and Workforce Risk Pods based on the home locations and demographics for 100% of a facility's local workplace communities (e.g., employees, contractors, customers, students or visitors). SaaS customers can, in some cases, avoid organization-wide workforce strategies and supply chain decisions that ignore site location-risk indexes. Government agencies can, in some cases, help keep employees and contractors healthy by understanding the risks a) in and around facilities and b) where their personnel live and move.

ii. Some embodiments of the SaaS solution also create and end-to-end supply chain risk assessment feature. Companies importing parts and components for manufactured goods can, in some cases, assess vendor supply risk based on the location of each vendor and the related shipping logistics. Based on the daily supply chain risk assessment, companies can, in some cases, make decisions to reallocate purchases to vendors in lower risk regions or seek new vendors in regions with reduce pathogen exposure. Additionally, companies can, in some cases, assess the distribution of finished goods to all points of sale worldwide. Outbound routes can, in some cases, be altered based on the supply chain pathogen assessment to provide the lowest pathogen exposure risk.

c. DATA-AS-A-SERVICE: A PUBLIC HEALTH POLICY AND MOBILE|SAAS INTEGRATION SOLUTIONS i. In some embodiments, the DaaS Pathogen Data Lake delivers daily, hyper-local building level risk indexes that equip public health policymakers with actionable insights and trends for any pathogen. From the first day a pathogen is reported, in some use cases, the SaaS instances tracks and visualizes the hyper-local risk levels and movement patterns. Policymakers can, in some cases, leverage these insights to enhance and improve policy decisions. Further, policymakers may receive insights regarding the Mobile and SaaS applications in countries where deployment to understand how pathogen infection rates are being impacted via the applications. These results can be compared to countries not using the applications to identify the potential for reduce infection rates via new public health policy decisions and the adoption of Mobile, SaaS, and DaaS applications with demonstrated and known public health benefits.

ii. In some embodiments, the DaaS 3rd Party Integrator allows any third-party application and website to access the DaaS Pathogen Data Lake and its hyper-local risk index end points and display that information within the solution based on a logical trigger (e.g., destination arrival or system query). The User may be presented with risk indexes in the digital asset that informs them of the virus infection risk for a location. Third party digital asset integration Use Cases may include: mapping and navigation—to reduce pathogen exposure risk during automotive trips (e.g., On-star™, Google Maps™, Waze™, etc.), travel planning-see a city's or travel route risk score before a user travels (e.g., American Airlines™, Crystal Cruise Lines™, Kayak.com™, etc.), lodging—to see the future risk score for a rental property or hotel prior to booking (e.g., Marriott™, Hilton™, Airbnb™, VRBO™, etc.), education-university administrators can see the risk index for all university students (based on the students home address) prior to the start of classes to develop safe campus movement strategies, and transportation—a management tool for fleet assets to reduce exposure risks (e.g., FedEx™, UPS™, USPS, etc.) or ride share trips (e.g., Uber™, Lift™, etc.).

FIG. 1 is a physical and logical architecture block diagram illustrating an example of a computing environment 10 in which a pathogen-surveillance server system 12 may cooperate with mobile computing devices 14 to surveilled a plurality of different pathogens and variants thereof. As explained in greater detail below, the illustrated distributed computing architecture may be operative to determine personal pathogen-risk scores of individual users; determine geolocation pathogen-risk scores of various places-of-interest; generate and customize behavior modification messaging for individuals to reduce their pathogen risk; and generate and customize behavior modification messaging for organizations to reduce the organizations' collective pathogen risk linked to the movement of its employees, contractors, customers, and manufacturing and distribution assets, and all enterprise supply chain movements worldwide. In some embodiments, these features may be implemented with privacy-safe movement transaction processing to assess pandemic risk, in some cases with information about various places-of-interest enriched with self-reported attributes of places-of-interest used to enhance or suppress corresponding risk scores of those places. It should be emphasized that a variety of independently useful inventive techniques are described herein. As such, it should not be assumed that all embodiments deploy the full suite of innovations described, as some embodiments may only use a subset of these innovations. Thus, simply because a technique is described as affording some advantage or addressing some problem, it should not be assumed that embodiments are limited to approaches that afford that advantage or solve that problem.

Some embodiments include a server system, like system 12, (e.g., a single server or a collection of servers, like in a micro-services architecture) that ingests location-indexed information relevant to assessing COVID-19 risk or risk from other pathogens, such as any pathogen (bacterium, virus, or other microorganisms that may cause disease), whether naturally occurring in nature or intentionally manufactured by people, that may create a pandemic. In some cases, various third-party APIs hosted on other server systems 18 may be interrogated for such information.

Some embodiments include a client computing device, like devices 14, 20, and 24 (e.g., physically remote from the server system 12) upon which users interact with the server system via a network, like the Internet. Examples include a desktop computer, laptop computer, mobile phone, automated teller machines, electronic public billboards, and the like. Interaction may be mediated by a web browser or a native application executing on the client computing device. In some cases, the server system hosts a geographic information system 84 in which attributes relevant to assessing COVID-19 (or other pathogen) risk are indexed to geographic places, e.g., coordinates, grid squares (or other regular or irregular tilings), places-of-interest (such as those bounded by a polygon with vertices expressed by latitude and longitude coordinates), metropolitan areas, voting districts, census blocks, ZIP codes, and the like). Examples of places-of-interest in include public places like airports, train stations, port authorities, courts, indoor places, like stores, restaurants, gyms, hotels, office buildings, residential properties, and local and national parks, and other physical and open places.

In some cases, information relevant to COVID-19 (or other pathogen) risk of geographic places is aggregated and analyzed by a server-side application executing on the server system. Examples of such analyses are described in the more expansive description of the figures that follows this overview.

In some cases, a native application 58, e.g., executing in the background of mobile user computing devices 14, interfaces with the server system 12 to obtain information about risks of places being visited. The native application 58 may interact with a geolocation framework or library of the client device's operating system (e.g., a corelocation framework on iOS™ or CLLocationManager class in Android™) to register to obtain events indicative of geolocation or changes thereof, e.g., traversing a geofence corresponding to a place-of-interest for which risk data is available from the server system 12, detecting a dwell, or detecting a change in position of greater than a threshold distance that warrants re-assessment. In some cases, the native application 58 (or a corresponding web application accessed via a browser) may locally compute aggregate measures of personal COVID-19 (or other pathogen) risk based on a sequence of visited places, or some embodiments may compute these values with the server system 12.

In some cases, information about COVID-19 (or other pathogen) risk of places may be aggregated across visits reported by a population of user-computing devices in a privacy-friendly way. For example, some embodiments may implement differential privacy approaches by which noise (e.g., by adding or subtracting random values from client-side metrics) is injected client-side by devices 14 into information reported to the server system 12, thereby frustrating attempts to de-anonymize the client device, while still permitting calculation of accurate population statistics (e.g., of a population that has visited a place) pertaining to COVID-19 (or other pathogen) risk by server system 12.

In some cases, to reduce battery consumption, geofence traversal is determined client-side by maintaining and updating a list of local geofences (e.g., within a threshold distance of a current location) relevant to the user's current location, along with COVID-19 (or other pathogen) risk related attributes of those places. Or some embodiments detect geofence traversal server-side, by reporting geolocation of the user-device to the server, which then cross-references against a geographic information system to retrieve such attributes.

In some cases, notifications intended to modify user behavior are presented on mobile devices 14 by native application 58 or via SMS messages or automated calls. Some embodiments may sense, after such notifications, whether the user complied with the suggestion and report to the server system the result. In some cases, the server system may maintain a list of different phrasings of suggestions and modify which are presented based on reported efficacy, e.g., with automated A/B testing. In some cases, the server system may train a machine learning model to predict efficacy based on various demographic and psychographic attributes of users and historical reported efficacy. The model may be used after training to select which notifications to present to different users.

In some embodiments, end users' computing devices may interface with the server system via web browsers, native applications, app clips, instant apps, and the like, executing on the client devices 14, 20, and 24.

In some embodiments, the server system 12 supports on-demand dynamic activation of cloud-based software components, e.g., with an elastically scalable set of lambdas, containers, virtual machines, or the like implementing various functional components described herein. Orchestration may be implemented with Kubernetes™, Apache Mesos™, or the like. Some embodiments may be implemented with AWS Lambdas™, which provides a computing environment to execute code without the need to provision or manage servers. Services may be by lambda's as respective functions, instances of which may be dynamically provisioned in response to event notifications received from an event notification generator.

In some embodiments, the server system may provide on-demand access by internal users, external users (e.g., customers, service partners), and developers, such as via infrastructure-as-a-service (IaaS), platform-as-a-service (PaaS), and software-as-a-service (SaaS) architectures, which in some cases, may be provided from a governed federation of internal (e.g., private cloud) and external cloud (e.g., commercial cloud) service providers. Some such embodiments allow for rapid and dynamic deployment and scaling of cloud-computing services. In some embodiments, a virtual appliance used to create a virtual machine within, for example, the Amazon Elastic Compute Cloud (EC2)™. In some embodiments, the server system may use Amazon Web Services™, Azure™, Google Cloud Platform™, or the like, for cloud-based components. In some embodiments, storage may be implemented with Amazon's Simple Storage Service (S3)™, Redshift™, Google Cloud Storage™, or the like.

In some embodiments, server system 12 may be implemented with tools like Gluon™, Keras™, Pytorch™, Tensorflow™, and the like, to prototype, build, and train machine-learning models, e.g., deep learning models, random forest models, deep reinforcement learning models, and the like. Supervised, semi-unsupervised, self-supervised, or unsupervised models may be used. In some cases, a collection of such models may be combined in an ensemble or pipeline.

In some embodiments, Amazon Simple Workflow (SWF)™, Celery™, Airflow™, or the like, may be used to maintain the execution state of workflows, tracks workflow versions and keeps a history of past workflow executions.

In some embodiments, AWS Data Pipeline™, Azure Data Factory™, SnapLogic Intelligent Integration Platform™, or the like, may be used to automate moving and transformation of data.

In some embodiments, Amazon Elastic Map-Reduce (EMR)™, Hadoop™, Spark™, Flink™ or the like may be used to analyze data concurrently, in a fault-tolerant, resilient fashion.

In some embodiments, Amazon's Simple Notification Service (SNS)™, Apache Camel™, or the like may push messages from software applications to subscribing endpoints and clients, and may be used as monitoring and management system.

In some embodiments, a cloud computing resource management application may provide one or more interfaces for configuring data sources from which performance or relationship data may be collected. Each data source may be a source defined by a particular cloud computing service or may be a source external to any cloud computing service.

In some embodiments, a cloud computing management application may be configured to generate topology map, bioinformatic or computational biology visualizations of resources based on data collected and stored by a data collection module. A topology map, bioinformatics or computational biology visualization may include a geolocation-based display of a set of nodes, each representing one or more cloud computing resources, and edges, each representing a relationship between two or more cloud computing resources.

Embodiments are expected to address various technical issues described below that arise at scale. In some embodiments, the computing environment 10 is geographically distributed, for example over the United States, North America, or the world. In some embodiments, components like the pathogen-surveillance server system 12 may be replicated with different instances serving and storing data about different geographic areas corresponding to the territory of various sovereign entities with an interest in how data is handled in their territory, in some cases without data being moved between territories for some jurisdictions. In FIG. 1, three mobile computing device 14 are shown by way of example, but it is expected that commercial deployments will involve substantially more, for example, more than 1 million, more than 10 million, more than 100 million, or more than 1 billion computing devices 14 corresponding to corresponding numbers of members of the public participating in the computing environment 10. Similarly, the other illustrated components may be replicated with multiple instances corresponding to other examples of the various described components, with the depicted examples merely serving to show one example of the type of systems with which the mobile computing devices 14 and server system 12 may interface.

In some embodiments, the computing environment 10 may further include an electronic medical record system 16, various public (or private) application program interface servers 18, computing devices of parties authenticated to supply information about places-of-interest 20, administrator computing devices 22, and healthcare worker computing devices 24. It is expected that commercial embodiments will interface with multiple instances of each of these components in some deployments consistent with the present techniques. In some embodiments, the illustrated components may communicate via the Internet 26 and various other intermediary networks, like cellular networks, wireless area networks, personal area networks, local area networks, and the like.

In some embodiments, the mobile computing devices 14 and other described computing devices may include the components of the computing device described below with reference to the last figure. Some embodiments of mobile computing devices 14 may include various software and hardware components by which some aspects of the present techniques may be implemented. In some embodiments, the mobile computing devices 14 may include memory 30 (which may include persistent and dynamic memory), one or more processors 32 (such as a central processing unit (CPU), and various hardware accelerators, like graphics processing units, machine learning accelerators, and the like), a cellular radio 34 (for example a baseband processor, MAC, PHY, and antenna for a 3G, 4G, or 5G, or later generation cellular network), a Wi-Fi™ radio (again having a network interface with a MAC, PHY, and antenna), a Bluetooth™ radio 38, a near field communication radio 40, a global positioning system sensor 42 (or other satellite navigation signals sensor, like GLONASS or Galileo sensors), and an ultrawideband radio 44. In some embodiments, components 34, 36, 38, 40, and 44 may both transmit and receive signals according to their respective protocols and allocated frequencies.

In some embodiments, the mobile computing devices 14 may further include a trusted execution environment 46 having a separate processor 48 (like a microcontroller or central processing unit) and memory 50. In some embodiments, the trusted execution environment 46 may be in a physically distinct region of a system-on-a-chip from the components 30 and 32 or on a separate chip, in some cases with the memory 50 being in a different physical address space the memory 30, for example, on a different memory bus or in a different range of addresses thereon for which the processor 32 or memory controller thereof is not configured to read or write directly to or from. The term "trusted" in this context is not indefinite in that it requires some measure of subjective trust, but rather refers to a term of art in which a class of execution environments are typically identified in the field and distinguished from untrusted computing environments on the same device. In some embodiments, the trusted execution environment 46 may store relatively sensitive data, like encryption keys for decrypting data in memory 30 or in memory 50, private cryptographic keys of asymmetric encryption key pairs used for authenticating a user or digitally signing communications associated with a corresponding public cryptographic key or decrypting communications encrypted with the corresponding public cryptographic key. In some cases, a public key of a cryptographic key pair (e.g., generated and exchanged with Diffie-Helman, RSA, ElGamal, elliptic curve, or various other asymmetric or hybrid cryptographic protocols) may include a pubic key by which a user is identified by and to system 12 and a private key by which the user is authenticated (in some cases, without revealing the private key to system 12). In some embodiments, the trusted execution environment 46 may communicate with the processor 32 via a relatively narrow channel, for example, via interrupts or other messaging protocols that have a relatively low attack surface.

In some embodiments, the mobile computing devices 14 further include a battery 52 that powers operation of the device and a camera 54. Each of the illustrated components may be in communication with processor 32, which may coordinate their operations. Some embodiments may further include an inertial measurement unit (IMU) having various accelerometers and gyroscopes (like a six axis IMU) and a magnetometer collectively used for dead reconning indoor positioning when GPS signals or cellular or WiFi™ triangulation are not available due to signal attenuation by a surrounding structure.

In some embodiments, the processor 32 may execute an operating system 56 (which in some cases is not executed by the trusted execution environment 46, which may have a separate operating system or may function without an operating system, for instance being implemented as a microcontroller or with a unikernel). The operating system 56 may provide an environment in which various services are exposed to a native application 58 configured to communicate with the server system 12. In some embodiments, the services include a geolocation framework 60. In some embodiments, the native application 58 may register with the operating system to receive events detected by the geolocation framework 60, for example, registering a callback function that, when called by the geolocation framework 60, causes the native application 58 two execute various responsive routines, like event handers that supplement geolocation histories in user profiles and request updates to risk scores.

In some embodiments, the geolocation framework 60 may be configured to emit events to the native application 58 responsive to various criteria specified by the native application 58, for example, the user moving more than a threshold amount, a change in a detected instance of the user dwelling within a location (for example being within a specified area for longer than a threshold duration), the user changing location by an amount sufficient to modify base stations or cellular towers communicating with radios 36 or 34, the user moving by more than a threshold amount as detected by an inertial measurement unit of the mobile computing device 14, or the like. Offloading detection of these events to the framework is expected to reduce battery and bandwidth consumption, as the framework may provide similar services for a variety of native applications, which is less resource intensive than having each application do the same.

In some cases, it may be less power intensive to obtain coarse geolocation measurements (like which cellular tower is proximate) than fine-grained geolocation measurements (like with GPS). Some embodiments of application 58 may selectively switch the framework 60 between which type of location measurement mode is used to preserve the battery 52. For instance, coarse geolocation measurements may be used when the native application detects that the user is moving faster than a threshold speed, like in a car, while fine-grained measurements may be used when the user moves slower and is in a crowded wireless environment, like in a densely populated area.

In some embodiments, the geolocation framework 60 may further monitor whether the user's geolocation has crossed a boundary of a geo-fence registered by the native application 58 with the geolocation framework 60, for example, at the behest of the server system 12 upon the server system 12 supplying a set of local, potentially relevant geo-fences to the native application 58 upon being queried for such geo-fences, for instance, after the native application 58 receives a signal indicating the user has moved by more than a threshold amount, or geofences corresponding to a predicted future location determined with the techniques discussed below. In some embodiments, geo-fence traversal may be detected remotely by the server system 12 or some other third-party service, for its instance responsive to the native application 58 emitting a signal indicative of a user's new geolocation. In some cases, places-of-interest with higher than a threshold pathogen risk may be geofenced, detecting traversal of which may cause the native application 58 to present a warning to the user.

In some embodiments, the native application 58 may further register to receive updates from the Bluetooth radio 38, NFC radio 40, ultrawideband radio 44, cellular radio 34, Wi-Fi™ radio 36, and an inertial measurement unit of device 14. In some embodiments, for example, indoor positioning may be sensed with the ultrawideband radio 44, for instance responsive to ultrawideband signals of various ultrawideband transmitters positioned in an indoor space, or responsive to identifiers of Bluetooth™ beacons received by the Bluetooth radio 38. Similarly, relatively precise positioning may be sensed with the near field communication device 40, for instance, responsive to the user placing the device within some threshold distance, like less than a meter of a transmitter in a point-of-sale terminal or NFC access panel of an electronic door lock.

In some embodiments, the native application 58 may be downloaded and installed on the mobile computing device 14 from a remote repository of native applications, such as one hosted by a provider of the operating system 56, like the Apple App Store™ or Google Play Store™. In some embodiments, the native application 58 may be provided by the same entity that provides the server system 12, and that entity may co-host a copy of the native application code in the same code repository as one hosting the code of the system 12. In some embodiments, upon installation, a user may register an existing account or create a new account with the server system 12, which may include populating a user profile with various physiological attributes (including medical conditions), psychographic attributes (e.g., values, desires, goals, interests, and lifestyle choices), and demographic attributes (like age, weight, gender, medical issues, and the like), and pathogen location and behavior risk avoidance preferences, examples of all of which are described in the provisional applications incorporated by reference by this filing.

In some embodiments, some or all of the data of the user profile may be stored exclusively on the user's mobile computing device 14, for instance in encrypted memory with the decryption key (for example, a symmetric encryption key or asymmetric encryption key) stored in memory 50, or some or all of the data may be stored in the server system 12. In some embodiments, less sensitive data may be stored in the server system 12 (like ZIP code), with more sensitive data (like full address) stored exclusively on the mobile devices 14. In some embodiments, the user profile data may be encrypted while in flight and at rest, and the data of the user's profile may be provided in anonymized form to the extent is provided to the server system 12. User profiles may include any subset of the various types of data described as being in the user profiles herein, and user profiles need not include all such fields to qualify as such, which is not to suggest that any other feature is not also amenable to variation.

In some embodiments, the data provided to the server system 12, to the extent any user profile data is provided, may be further protected with differential privacy techniques. In some embodiments, attributes of the user profile may be modified with a respective value randomly (e.g., pseudo-randomly) selected from a corresponding distribution for the attribute, like a Gaussian distribution from which a value is selected to inject noise by adding the value to the value of the user's profile. In some embodiments, the attribute-specific distribution may be selected such that a measure of central tendency of that distribution (like a mean, median, or mode) matches the unmodified value in the user profile. In some embodiments, this technique may allow the server system 12 to accurately compute population-level statistics, without the server system 12 having access to the unmodified values in user profiles through application of the central limit theorem.

In some embodiments, the native application 58 may execute steps of the various processes described below with reference to flowcharts and data models. In some embodiments, the native application may further register to receive push notifications from the server system 12, for instance via the Firebase Messaging Service™ or Apple Push Notification Service™.

In some embodiments, when the user is not interacting, the native application 58 may execute as a background process of the mobile computing device 14, for instance, in a low-power mode, ready to receive and process updates as the user moves through various geographic areas and visits various places-of-interest. Some embodiments, the native application 58 may further have access to various other services from which future movements may be inferred, for example, a calendar of the user (either hosted on the mobile device 14 or in a remote server) and a navigation application (like a mapping application) in which the user requests and obtains routing information by which the user navigates to various geographic places specified by the user. In some embodiments, the native application 58 may obtain and process various geolocations to be potentially visited to make the types of predictions described below. Examples include determining that the calendar or requested route in a mapping application indicates the user intends to travel to a identified place-of-interest in the future, querying from the server system 12 a risk score of that place-of-interest, determining whether that risk score exceeds a threshold, and in response to determining that the risk score exceeds a threshold, causing a user interface to be presented to the user indicating a warning and in some cases suggesting an alternative to the problematic place-of-interest, such as a another business providing goods or services in the same category that is geographically proximate (for instance, the closest or within some threshold distance or travel time of the user's current location or predicted future location) or alternatively or additionally, suggesting an entirely new route with lower risk factors. In some cases, future visits to places-of-interest may be inferred from a person's historical visits, e.g., by training a hidden Markov model (or other dynamic Bayesian network), recurrent neural network, or transformer architecture on a person's geolocation history and querying the model for predictions of future visits given a recent (within a threshold number of places or amount of time) set of places visited or given a day of the week.

Reference herein to various scores or probabilities being compared to thresholds should be read broadly as encompassing both scenarios where increasing score has one semantic value and scenarios where describing the score has the same sematic value. For instance, reference to a determination that a score exceeds a threshold should also be read as referencing a scenario where the inverse or negation of that score is less than a threshold. Similar principles apply to probabilities being compared to thresholds, e.g., determining that the probability of an event occurring exceeds a threshold is equivalent to determining that the probability of the event not occurring is less than the threshold.

In another example, the native application 58 may register to receive information about social networks in which the user is a member, for instance from Facebook™, LinkedIn™, Instagram™, workplace organization charts, or the like, provided that the user authorizes such access. In some embodiments, the user's social network may be interrogated to identify other members of the public adjacent the user in the social graph or within some threshold distance of the user in a social graph, for instance less than two less than three or less than four links in a social graph. These other people may be identified (e.g., pseudonymously or anonymously) and associated with the user in the user profile, in some cases with those other members of the public being associated with their own unique identifiers within the pathogen-surveillance distributed application implemented with the computing environment 10, of which the user of the computing device 14 may have one as well. In some embodiments, these identifiers may be unique to individuals, persistent, but not contain any personally identifiable information. Or in some cases, these identifiers may mutate over time, in some cases in a deterministic way and in some cases in a nondeterministic way, to make it harder to track the users over time to protect user privacy. In some embodiments, a user may specify their social network manually by selecting from their contacts or other users having profiles within the pathogen-surveillance distributed application being described. In some cases, the resulting records may be stored in the user's profile.

Interaction with EMR records, to the extent implemented in some embodiments, is done in a privacy-sensitive, HIPPA-compliant manner, with user consent. In some embodiments, functionality of the native application 58 or system 12 may be integrated into an electronic medical record system, or the native application 58 or server system 12 may further authenticate itself to the electronic medical record system 16 and access the user's medical records, provided that the user authorizes such access. In some embodiments, these medical records may supplement the self-reported medical attributes of the user. In some embodiments, the native application 58 may further have write access to such records in the electronic medical record 16 or the server system 12 may have write access, for instance with the ability to write a personal risk score or data indicative of patterns of behavior relevant to diagnosing and otherwise assisting the user. Some embodiments may interface with a diverse set of electronic medical record systems 16, e.g., having different APIs and data formats. In some cases, an EMR system may cause messages to be sent that prompt users to install the native application to view context to a risk-related message or the message itself, which may tend to increase the install base.

In some embodiments, the native application 58 or server system 12 may further register to receive data from various wearable and non-wearable biometric monitoring devices of the user, like smart watches with pulse oximeters, movement trackers, heart rate sensors, sleep sensors, and the like, or smart scales, blood monitoring devices, blood sugar level sensors, blood pressure sensors, and the like. In some embodiments, upon being authorized by the user, such data may be processed by the native application 58 or stored in the user profile to further augment the personal risk assessment.

Details of examples of specific risk score calculations based upon the types of data described as accessible to the native application 58 are described with greater detail below with reference to the various flowcharts.

In some embodiments, the pathogen-surveillance server system 12 may execute various processes like those described below with reference to flowcharts to surveil the spread of various pathogens and variants thereof and compute scores indicative of risk for those pathogens attributable to individuals, organizations, and places-of-interest. Further, some embodiments may effectuate various types of messaging described below to mitigate that risk, in some embodiments using techniques described below that afford various privacy protections and benefit from information supplied by parties operating or with intimate knowledge of places-of-interest. In some embodiments, the server system 12 may include an application program interface server 70, a web server 72, a controller 74, an anonymized user profile repository 76, a cache server 78, an orchestrator 80, a rea-time stream processing compute cluster 82, and a geographic information system 84. In some embodiments, the illustrated components of the server system 12 may be implemented in a monolithic architecture on a single computing device or as a distributed architecture, for instance, as a microservices architecture with different instances of each component or various services constituting the components implemented as virtual machines, containers, lambda functions, unikernels, or standalone computing devices implemented in a private, public, or hybrid cloud computing physical architecture.

In some embodiments, the servers 70 and 72 may by bound to a network socket to receive network communications addressed to a corresponding port number to which they are bound. In some embodiments, the servers 70 and 72 may be nonblocking web servers, for instance implemented with promises or deferred's, operative to service a relatively large number of concurrent sessions, such as more than 100, more than 1000, or more than 10,000. In some embodiments, network communications may include a session identifier by which communications may be associated with previous communications in the same session. In some embodiments, a stateless communication protocol may be used, and some embodiments may implement, for example, a representational state transfer, or REST, protocol.

In some embodiments, communications via the servers 70 and 72 are coordinated by the controller 74, which may coordinate the operation of the other components of the server system 12. In some embodiments, the controller 74 includes a view generator operative to generate user interfaces (e.g., data to populate UI templates or HTML, CSS, and JavaScript™ directly) for obtaining information and presenting outputs to users. In some embodiments, the controller 74 executes the various processes described below with reference to flowcharts attributable to the server system 12 by coordinating with the other illustrated components.

In some embodiments, the anonymized user profiles 76 may be stored in the server system 12, though it should be emphasized that some embodiments may leave this information exclusively on the mobile computing devices 14 to further enhance privacy, which is not to suggest that any other feature is not also amenable to variation. In some embodiments, these anonymized user profiles 76 are stored in encrypted form and associated with identifiers that distinguish among users of the server system 12 without correlating with personally identifiable information of the user. In some embodiments, the user profiles 76 are different from user profile stored on the mobile computing devices 14, for instance, the user profiles in the repository 76 may have reduced granularity (storing ZIP code rather than street address, or decade of age rather than exact age), the user profiles in the repository 76 may have been modified with differential privacy techniques that inject noise, or the user profiles in the repository 76 may have a subset of the data stored in the user profiles on the mobile computing devices 14, each to further enhance privacy. In some embodiments, the illustrated repository is a relational database or a noSQL database, such as a key-value store or document-based database, for instance based upon XML or JSON documents.

In some embodiments, the cache server 78 includes an instance of Redis™ or Memcached™ to facilitate relatively fast responses to request to the server 70 and 72 implicating recently accessed data. In some embodiments, the recently accessed data may be indexed with a hash value based upon the content of the data or an identifier of the data, such that the recently accessed data may be relatively quickly indexed into, for instance, via a key-value store where keys correspond to the hash values, like a hash table. In some embodiments, the cache server 78 may, for some periods of time maintain, data that is inconsistent with the more authoritative records in the user profile 76, geographic information system 84, or other repositories of the server system 12, until the corresponding caches are invalidated or updated with new values.

In some embodiments, the server system 12 includes a natural-language-text generation model 79 that implements behavior and organizational modification messaging based upon pandemic risk scoring, as described in greater detail below, including in passages with reference to FIG. 5 and FIG. 6.

In some embodiments, the orchestrator 80 may be operative to orchestrate operation of various components by which the pathogen-surveillance server system 12 is implemented. In some embodiments, this may include elastically scaling, managing, and configuring compute resources available based upon demand. Some embodiments may dynamically instantiate additional virtual machines, containers, unikernels, or the like responsive to need and destroy those instances when the need passes. Some embodiments may include components by which a private domain name system is implemented to facilitate communication among the managed components, by mapping Internet Protocol addresses of those components to domain names within a private domain name space of the server system 12. In some embodiments, the orchestrator 80 may be implemented with Kubernetes™ or Docker™, for example.

Some embodiments may further include a real-time stream processing compute cluster 82. Examples include compute clusters implemented with Apache Spark™, Flink™, or the like. In some embodiments, data may be stored in resilient distributed datasets, which may include a read-only multiset of data items. These data items may be distributed among a cluster of computing devices in a manner that affords fault tolerance in the event that one of those computing devices fail, e.g., with redundancy. The data items may form a distributed shared memory that affords more flexibility than non-shared approaches like in some forms of MapReduce, which is not to suggest that use of MapReduce or non-shared approaches is disclaimed. In some cases, the analysis may be iterative, in the sense that the same data item may be processed multiple times, in some cases responsive to branching logic, and in some cases, producing transformed data items, which is expected to afford lower latency than some MapReduce implementations. In some cases, the compute cluster may be implemented with a cluster manager and distributed storage system, and the system may be configured to perform streaming analytics by performing transformations on mini-batches of data, in some cases implementing a lambda architecture. Or some embodiments may respond to events (e.g., those implemented with Apache Storm, as applied in Flink™), rather than mini-batches, to reduce latency arising from mini-batch durations. Some embodiments may implement structured streaming with datasets in continuous processing.

Some embodiments may further include a geographic information system 84. The term "geographic information system" is a term of art used to refer to a particular class of data repositories configured to store information about geographic places. In some embodiments, the geographic information system 84 may facilitate relatively fast access to information about designated places in queries with a data model described below with reference to FIG. 3. Some embodiments may maintain records of places-of-interest, like businesses, parks, government offices, schools, golf courses, municipalities, cities, counties, states, and countries, each of which may be represented by bounding polygons having vertices expressed as latitude and longitude coordinates, each having a unique identifier and a record indicating attributes of the corresponding place-of-interest. Examples of such attributes may include location risk scores and location attributes relative thereto described below, along with names of the place, categories of the place in an ontology of places, like business→restaurant→Italian food.

In some embodiments, the geographic information system 84 may store such records for more than 10,000, more than 100,000, more than 1 million, or more than 10 million places-of-interest in a geographic area. Some embodiments may be configured to respond to a query specifying a single lat-long coordinate by returning one or more places-of-interest encompassing that coordinate. Servicing such queries may be relatively slow with some traditional approaches that require comparing that lat-long coordinate to every polygon in the entire database to determine which polygons include the lat-long coordinate (some of which may be overlapping polygons). Point-in-polygon algorithms, like the winding algorithm, or the ray-tracing algorithm, are relatively computationally expensive, and replicating them, for instance, 10 million times for every place-of-interest to determine which places-of-interest include that point is expected to impart unacceptable latency for some use cases.

To mitigate this problem, some embodiments may implement a two-layer data model in which a geographic area is quantized with a grid having unit tiles, and identifiers of those unit tiles index into the subset of bounding polygons within those unit tiles, such that identifying a unit tile in which a point resides allows just the subset of polygons within that unit tile to be selected and compared to that point, potentially resulting in a dramatic reduction in compute resources needed to respond to a query in some designs. Further, in some embodiments, those unit tiles may be addressed with, for example named by, identifiers that correspond to their geographic area of coverage, for instance, by naming unit tiles according to a threshold number of significant digits of latitude and longitude coordinates corresponding to their geographic area. Or some embodiments may name tiles according to a location on a space filling curve, like a Hilbert curve, Morton curve, or Z curve, and in some cases, those locations also correspond to a digital representation or binary representation of a threshold number of significant digits of the geolocation coordinates.

In some implementations, a future geolocation of a user, or a movement of a user may generate a new geolocation for which an update to risk scores is requested. This may result in a query to the server system 12 and the geographic information system 84 requesting information about places-of-interest encompassing the new geolocation, e.g., embodiments may receive a query specified by latitude and longitude of a point. In response, some embodiments may truncate a threshold number of significant digits, for instance, by discarding less significant digits than that threshold, appending the resulting to coordinates to one another or computing a hash value based on both coordinates to produce a single value, and looking up the corresponding tile name with a content addressable lookup based on that single value that then returns the subset of polygons of places-of-interest within the corresponding tile. Some embodiments may then execute a point-in-polygon algorithm on each of those responsive subset of polygons to determine which include the point specified in the query.

A point geolocation be determined to be within a place-of-interest with a variety of techniques. In some cases, the place-of-interest may be defined by a center point (e.g., a latitude and longitude) and a radius, and some embodiments may calculate a distance between the center point and the point geolocation and determine whether the point geolocation is within the geofence by comparing the distance to the radius, with distances exceeding the radius indicating the point geolocation is outside of the geofence. In some cases, the place-of-interest may be defined by a polygon having latitude and longitude vertices. Some such embodiments may execute (e.g., on the client or server) a ray-casting algorithm or a winding number algorithm to determine whether a current location is within a geofence. For instance, some embodiments may determine whether a point geolocation is within a polygon corresponding to a geofence by counting a number of times a ray originating at the point geolocation intersects a side of a polygon defining a geofence and, then, determining whether the point geolocation is within the geofence based on whether the count is odd (corresponding to being inside) or even (corresponding to being outside). In some such implementations, every edge of the polygon may be tested for intersection with the ray, and vertices may be tested for intersection with the ray and tracked in memory as already having been deemed intersected to avoid double counting of vertices for adjacent sides. Alternatively, or additionally, the point geolocation may be compared to a geofence by summing angles between rays extending from the point geolocation and vertices defining each sequential side of the polygon. Some embodiments may deem the point geolocation to be inside the geofence in response to determining that the sum is non-zero. Some embodiments may calculate such angles according to an inverse trigonometric function, or to expedite processing and avoid computationally expensive calculations, some embodiments may leverage the closed shape of the polygon and simply account for which quadrant each additional edge places each sum.

Some embodiments include the electronic medical record system 16 storing records indicative of medical conditions and healthcare histories of users, which may be interrogated to inform user profiles and various risk scores described below. Further, the user's risk score may be discussed by a treating physician or other medical associate authorized to access such information or presented to the user via the electronic medical record systems mobile and web-based solutions.

In some embodiments, the computing environment 10 further include public API servers 18 or private servers that expose APIs (or user-facing interfaces suitable for scraping) from which data relevant to pandemic surveillance may be obtained. Examples include weather data, traffic data, census data, waste water data, telecommunication network footfall data at the building or other bounding box level, commercial and residential building infrastructure data, Department of Education data for each school, including its district bounding box, physical location, number of students, faculty and administrators, animal infection data, Centers for Disease Control reports about prevalence of various pathogens and variants thereof at various geolocations, social media and news feeds with natural language text mentioning geolocations and having discussion of prevalence of various pathogens and various geolocations from which prevalence may be inferred, Centers for Disease Control models of various pathogens (like $R_0$ and $R_t$ values, case fatality rates, vaccination rates, seroprevalence rates, the like), and corresponding services from the World Health Organization and other countries' governments.

Some embodiments may further include as part of the computing environment 10 computing devices of account holders or other entities authorized to authoritatively report on attributes of places-of-interest, as indicated by block 20. In some embodiments, the server system 12 may host a web form or expose an API by which such information be submitted. Examples of such information include types of air filtration, rates of air turnover through the filtration system, whether the place-of-interest is indoors or outdoors, whether UV lighting is used to sanitize surfaces, cleaning protocols implemented at the place-of-interest or certifications thereof, whether food is prepared at the place-of-interest, whether food is consumed at the place-of-interest, demographics of people visiting the place-of-interest and density of people or number of people visiting the place-of-interest at various times of day, and the like.

Some embodiments may further include an administrator computing device 22 by which the server system 12 may be configured and managed.

Figure 2:
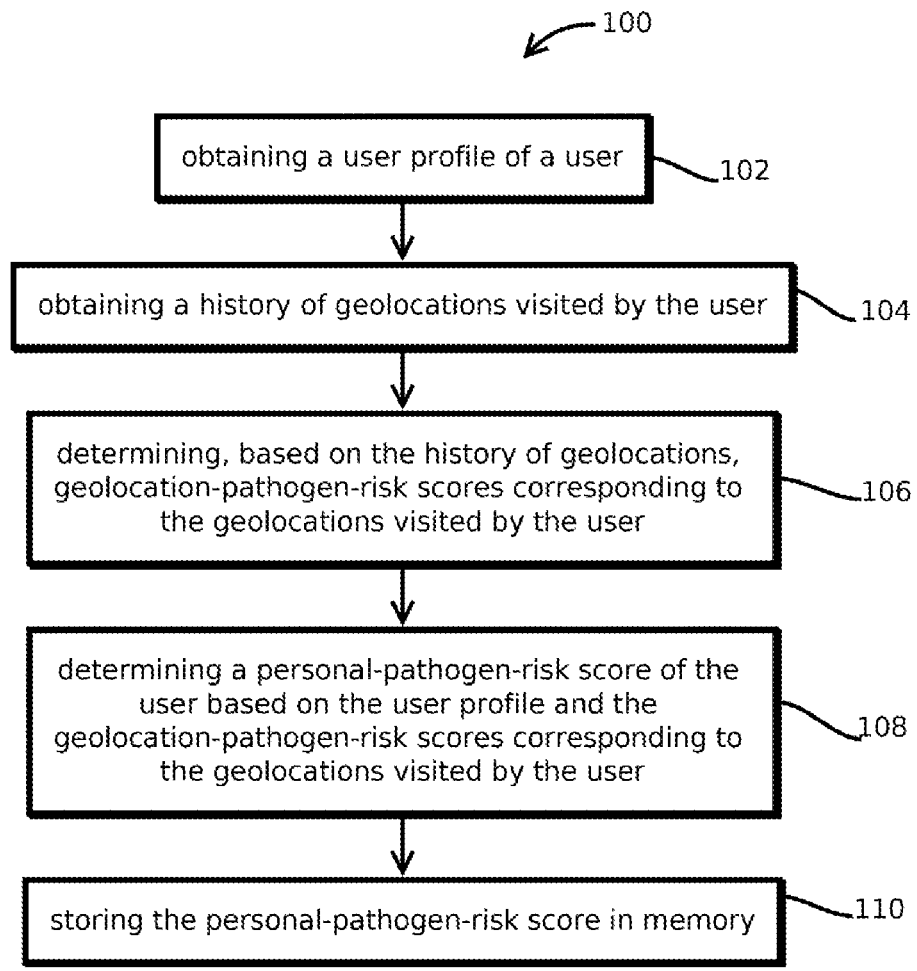
FIG. 2 is a flow chart of an example of a personal-pathogen-risk-scoring process that may be executed by the system of FIG. 1.

Some embodiments of the computing environment 10 may further include a computing device of a healthcare worker 24 by which the healthcare worker interacts with the electronic medical record system 16 to access records about patient medical conditions and other physiological attributes or demographic attributes of the user in the course of providing medical care. In some embodiments, user interfaces prompted by risk scores calculated with the described techniques may be presented on a display screen or other output of the healthcare worker computing device 24, for example, in the manner described below with reference to FIG. 2.

The mobile computing device 14 may be any of a variety of different types of computing devices that tends to be present with a user as they move about their day. Examples include mobile phones, wearable computing devices (like health trackers and head-mounted displays), in-automobile computing devices, tablet computers, laptop computers, and the like.

Personal Pathogen-Risk Index

Details of the pathogen-surveilling workflows of the server system 12 are described in greater detail below with reference to the various flowcharts and diagrams of data structures. In some embodiments, this may include executing some or all of a process illustrated in FIG. 2 by which a personal pathogen risk score of a user is computed with process 100. In some embodiments, the operations of process 100 may be executed entirely by the server system 12, entirely by the mobile computing device 14, or through cooperation of the of the two computing devices 12 and 14. The illustrated operations may be executed in a different order, some operations may be executed multiple times, some operations may be omitted, some operations may have additional replications, and operations may be executed serially or concurrently in any suitable permutation, none of which two is to suggest that any other feature described herein is not also amenable to variation. The same qualification applies to the various other processes and functionality described herein. Further, like the other processes and functionality described herein, the process 100 may be implemented by executing, with one or more processors, instructions stored in a tangible, non-transitory, computer readable medium, in some cases with the same processor executing all instructions, or in some cases with different processors executing different subsets of the instructions. In some embodiments, this process and the other functionality described herein may be implemented with one or more computing devices like those described below with reference to the last figure.

In some embodiments, the process 100 may be initiated responsive to a user request for a personal pathogen risk score, or in some cases, the process 100 may be initiated automatically, for instance during a scheduled batch process to update such scores, like run nightly or daily or hourly, or responsive to an event that potentially affect such a score, for instance, responsive to the user visiting a new location, supplying new information about their medical state, a person in the social graph of a user for whom the score is to be calculated providing new information in these categories (like reporting an infection or exposure thereto), a place the user visited receiving updated information (like a report that someone else contracted a virus at the place-of-interest during a time the user visited or within some threshold duration before their visit), updated information about attributes of such places that affect propensity of viruses or other pathogens to be transmitted, or a change in a model from which such scores are computed.

Some embodiments include obtaining a user profile of the user, as indicated in block 102. In some embodiments, this may include accessing a user profile that has been encrypted by accessing a corresponding key in a trusted execution environment in accordance with the techniques described above. In some embodiments, a user profile or part thereof may be encrypted and stored is a ciphertext on the mobile user device 14 and a key to decrypt that ciphertext may itself be encrypted and stored in the same memory. Some embodiments may pass the ciphertext of that key into the trusted execution environment where it is then decrypted and used to decrypt the ciphertext in the memory accessible to the operating system. Or in some cases, the entire ciphertext of the user profile is passed of the trusted execution environment, where it is decrypted, and returned for processing and plaintext form. In some embodiments, obtaining a user profile includes accessing user profile with the server system 12 described above. In some embodiments, the access may be authenticated by the user of the mobile computing device, for instance with by the user cryptographically signing a challenge, like a high entropy value, such as a random value of more than 256 bits, sent by the server system 12 to the mobile computing device 14, which may cause the native application 58 thereon to request the trusted execution environment to cryptographically sign the challenge value with a private key that is then reported back in the form of a digital signature reported back to the server system 12 and used by the server system 12 to verify that the party cryptographically signing the challenge has demonstrated proof of access to the private key without providing the private key outside of the trusted execution environment. In some cases, obtaining the user profile includes requesting information in the user profile from the user, the electronic medical record system 16, or the various other third-party applications described above having data about users, like calendar services, and social networks. In some embodiments, the profile of the user further includes a geolocation history of the user, like lat-long timestamped breadcrumb histories or a history of geolocations in which the user has been determined to dwell at the geolocation, such as a place-of-interest, for more than a threshold amount of time, or a residence or work location inferred or specified by the user. In some cases, dwells may be detected by the geolocation framework 60, the native app 58, the server system 12, or a third-party service like Radar™ for detecting geofence traversal and dwell time.

Embodiments may include obtaining a history of geolocations visited by the user, as indicated in block 104. In some cases, these geolocations are expressed as lat-long coordinates, tile identifiers, identifiers of places-of-interest visited, or the like. In some cases, these geolocations in the history extend back a threshold duration of time, such as those in the within the last week, two weeks, month, or less or longer. In some embodiments, the history of geolocations is obtained from the user profile or from some other record. In some cases, such geolocations in the user's history may further include an elevation dimension, like a height or floor of a building.

Some embodiments include determining, based on the history of geolocations, geolocation-pathogen-risk scores corresponding to the geolocations visited by the user, as indicated by block 106. These risk scores may be calculated with techniques described below with reference to subsequent flowcharts. In some embodiments, the geolocation-pathogen-risk scores may be precalculated and stored in the geographic information system 84 by the server system 12. To obtain the scores, some embodiments may query the geographic information system 84 with each visited geolocation in the history, which may include submitting queries for points-of-interest corresponding to (for example, encompassing in this context) lat-long coordinates in the geolocation history. In some embodiments, servicing this query may include the steps described above by which such queries may be expedited, using data structures like those described below with reference to FIG. 3, which in some cases, may include multiple layers for some polygons corresponding to different floors of a building.

In some embodiments, the geolocations may be filtered to exclude those for which the user was present for less than a threshold amount of time, in some cases with that threshold depending upon attributes of the geolocation, like the self-reported attributes described below that are indicative of how quickly various pathogens are expected to spread, for instance, based upon airflow, filtering, and the like. In some embodiments, these thresholds also vary according to the pathogen and the variant of the pathogen.

In some embodiments, as described in greater detail below, each place-of-interest responsive to such a query may include a plurality of different risk scores. The risk scores may indicate the likelihood of contracting a pathogen at the geolocation, or in some cases, a particular room or floor of a place-of-interest. In some embodiments, each place-of-interest may be associated with a different risk score corresponding to each of a plurality of different pathogens. In some embodiments, each pathogen may have a plurality of variants in circulation, and some embodiments may include a variant-specific risk score for the geolocation for each pathogen. In some embodiments, the risk scores may vary according to time, like time of day or absolute time, for instance, due to an infected person visiting on a particular day, or a pattern in which more people are present during certain hours at the place-of-interest. Some embodiments may store and determine pathogen-specific, variant-specific, time-specific risk scores for each place-of-interest, and in some cases, queries may specify a pathogen, geolocation, and time (like a time at which a user was at the geolocation) to retrieve relevant risk scores. Or some embodiments may access the full set of risk scores for all pathogens and all variants. In some cases, risk scores may be, or may correspond to, probability of contracting the corresponding pathogen at the geolocation. Determining in this context may include retrieving a previously computed value or computing a new value of the geolocation-pathogen-risk scores. In some cases, risk scores for geolocations may be modified to account for things that change over time, like density or amounts of visitors, weather, cleaning schedules, or the like.

In some embodiments the geolocation-pathogen-risk scores may, rather than being scalars, take the form of models or other functions from which a personalized-geolocation-risk score can be calculated based upon attributes of a user's profile. For example, in some cases the geolocation-pathogen-risk scores may take the form of a linear equation or trained machine learning model operative to receive as input several parameters from a user's profile and output a pathogen, variant, and time specific score customized to the corresponding user for that location. For example, such a geolocation-pathogen-risk score taking the form of a geolocation-pathogen-risk function may have a linear equation with a plurality of coefficients that have been curve fit based on historical data to predict a more individualized risk from exposure to that particular pathogen, at a particular time, for a particular pathogen and variant of that pathogen, for that user. In some embodiments, these functions may be evaluated on the mobile device 14 or that by the server 12.

Some embodiments may then determine a personal-pathogen-risk score of the user based upon the user profile and the geolocation-pathogen-risk scores corresponding to the geolocations visited by the user, as indicated by block 108. In some embodiments, these personalized scores may reflect an aggregate risk from exposure spanning a plurality of visited geolocations, in contrast to the personalized-geolocation-pathogen-risk scores described above based upon functions corresponding to the individual geolocations, times, variants, and the like. In some embodiments, the number of geolocations at issue may be greater than two, greater than five, greater than 10, or greater than 50 for an individual.

Some embodiments determine the personal-pathogen risk scores by computing amounts of risk attributable to each of the geolocations (which may include future predicted geolocations for forecasted risk scores) and then combining the component risks into an aggregate risk reflecting the cumulative effect of the user visiting the various geolocations on risk of the user contracting the pathogen and variant at issue. In some embodiments, this combination may be a sum of the probabilities corresponding to the different visits to different geolocations. In some embodiments, a single geolocation may have been visited multiple times, with different amounts of risk attributable to that geolocation at each visit. Some embodiments may determine separate personal risk scores for contracting, being contagious, and suffering an adverse medical consequence (including death), as described below.

In some embodiments, the personal-pathogen-risk score of a user may also be based upon personal-pathogen-risk scores of other users adjacent the user in a social network or within some other number of degrees of connection. In some embodiments, these personal scores may vary over time, and the score used may depend upon when the user was in the same location as that member of their social network, using the score of the member of the social network being contagious from when the member of the social network was at the same location as the user for whom a score is being calculated. For example, if a user visits a friend or family member who has a relatively high-risk score for being contagious, that may tend to increase the risk score for the user. Similarly, if the user visits a friend who has, in the recent past, for instance, within some threshold duration of time, themselves been present with several other people who have relatively high personal-pathogen-risk scores for being contagious, then that may tend to drive up the rescore of the risk score of the user via the friend or family member's personal risk score for being contagious.

In some embodiments, the personal-pathogen-risk score is also based upon an individualized likelihood of the user contracting a pathogen if exposed given that users demographic, psychographic, and physiological attributes. For example, children may be more or less susceptible to some pathogens relative to older people. Similarly, gender, weight, ethnicity, and other attributes of a user may make them more or less likely to contract the pathogen if exposed. In some embodiments, the personal-pathogen-risk score may be adjusted after accounting for geolocations visited with the user's likelihood of contracting if exposed, for example by multiplying the probability of contracting if exposed by the aggregate geolocation risk scores.

Some embodiments may further account for the likelihood of a person experiencing an adverse medical result upon contracting the pathogen at issue or variant of pathogen at issue. In some embodiments, this may depend upon the demographic and physiological (including medical history and comorbidities) attributes of the user. In some embodiments, a machine learning model or linear equation may accept as inputs a collection of attributes of the user from the user profile and output a probability of the user suffering a designated adverse medical event conditional upon the user contracting the pathogen or variant at issue. In some embodiments, these models may be trained upon data reported to the server system 12, in some cases after applying differential privacy techniques such that individualized data is less personally identifiable but population statistics remain valid and suitable for training models. The types of events that qualify as an adverse medical event may vary by the use case and may be predefined. Examples include staying in the hospital for a threshold duration of time, dying, missing work or school, or the like. In some cases, multiple personal-pathogen-risk scores may be calculated for each for a different type of adverse medical event upon exposure and contracting pathogen at issue.

In some embodiments, these probabilities of an adverse medical event may be weighted according to a confidence in the evidence for those probabilities, which in some cases may be learned or in some cases may be hand coded based upon, for example, medical journal articles. For example, a relatively high probability of an adverse medical event for which there is relatively little evidence or substantial variation among the existing evidence may be afforded a lower weight, which may tend to lower the personal-pathogen-risk score that is ultimately calculated, for example by multiplying the above-described modified intermediate personal-pathogen-risk scores by these weighted probabilities to produce a final personal-pathogen-risk score or set of scores corresponding different adverse medical events, in some cases for each pathogen at issue and in some cases for each variant of each pathogen at issue. In some embodiments, a personal-pathogen-risk score may be calculated that aggregates among all variants for a given pathogen, and some embodiments may compute a personal-pathogen-risk score the aggregates among all pathogens as well. Thus, a user visit to a place where likelihood of contracting to different pathogens is moderate may result in a relatively high personal-pathogen-rescore when the effects of both of those pathogens are accounted for in the resulting aggregate score. The term "personal-pathogen-risk score" is used generically to refer to both aggregate instances and the components of those aggregates as noted above.

In some cases, different pathogens may combine synergistically to make adverse medical events more likely. For instance, contracting COVID-19 and the flu may be substantially more dangerous than either one individually. Some embodiments may maintain a two, three, or four or higher dimensional matrix in which dimensions correspond to different pathogens or variants thereof and values in the matrix indicate strength of interactions therebetween. These values may be applied as weights when calculating aggregate personal-pathogen-risk scores that account for risk of an adverse medical event across multiple pathogens.

In some embodiments, information from electronic medical records from system 16 may be accounted for when determining probabilities of an adverse medical event conditional upon contracting a pathogen or variant thereof. Some embodiments may retrieve these values from a user profile or directly from the system 16 to compute the personal-pathogen-risk scores. In some cases, different medical conditions may interact more severely with different pathogens or variants thereof. Some embodiments may train a machine learning model or have hand-coded rules to modify risk score to account for such medical conditions. The electronic medical records system 16, in some embodiments, may render a comprehensive persona risk index for any pathogen taking into account all of the patient data contained in the records system which may be viewed by the patient via a mobile app or web-based system or alternatively, presented by a treating physician during any patient-|doctor interaction (whether remote or in person).

In some embodiments, the personal-pathogen-risk score may then be stored in memory, as indicated by block 110, for example, in persistent or nonpersistent memory, like in program state accessed when facilitating various forms of communication or risk mitigation techniques described below with reference to subsequent flowcharts. For example, in some cases, the stored personal-pathogen-risk score may be compared against a threshold by the system 12 or system 16, and upon determining that the score exceeds the threshold, some embodiments may cause the EMR system 16 to present a user interface to a healthcare professional, like a nurse or doctor operating device 24 in FIG. 1, prompting them to discuss the user's risk, adjust medical care to account for the user's risk, and discuss risk mitigation strategies with the user. In some embodiments, these user interfaces may be presented on the healthcare worker computing device 24, which may be configured to interface with the electronic medical record system 16. In some embodiments, the EMR system calculates the personal-pathogen-risk score after the algorithm is deployed into the system. Once the algorithm is deployed, the personal-pathogen-risk score may be calculated for each patient file. The accuracy of the personal-pathogen-risk score may be dependent on the extend of medical histories needed to calculate the score. In the case insufficient information is present in a patient file, the EMR system may store a result "Unable to Score". In this instance, the treating physical may ask the patient questions necessary to manually enter the patient factors into the EMR system. The EMR system may then calculate the personal-pathogen-risk score and allow the treating physician to discuss the results with the patient. In the case basic information is present in any patient file, the EMR system may store a personal-pathogen-risk score proxy. In the case comprehensive information is present in a patient file, the EMR system may store a personal-pathogen-risk score.

Figure 3:
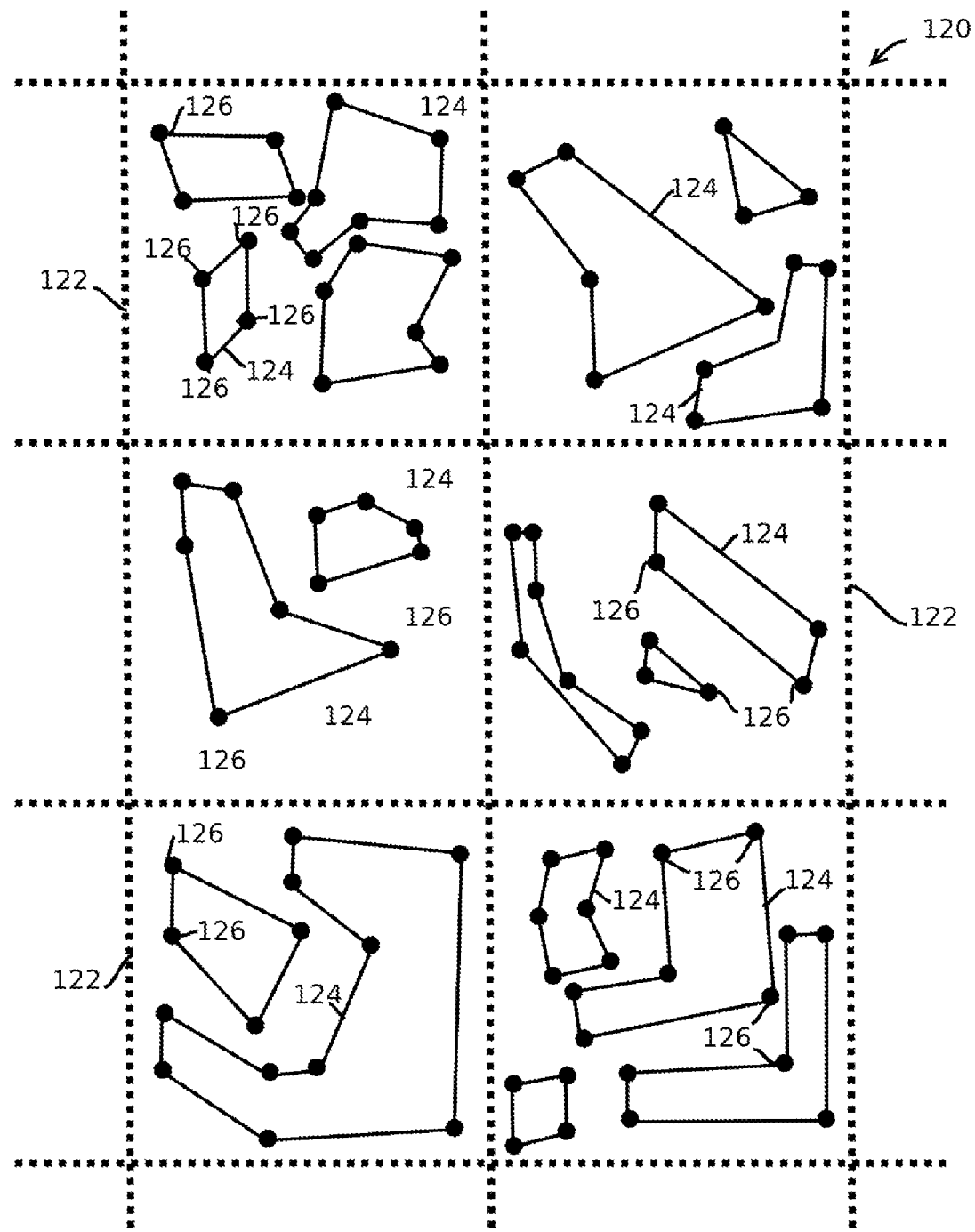
FIG. 3 is a schematic depicting a data structure for reducing latency when querying a geographic information system for pathogen-related-risk records pertaining to places-of-interest.

FIG. 3 illustrates an example of a data structure by which access to information about geolocations, given a geographic coordinate set, may be expedited. As noted above, a relatively large number of places-of-interest may be tracked, and computing a point-in-polygon algorithm for every single place-of-interest in, for example, the United States, to respond to a single query for which place-of-interest includes a latitude and longitude coordinate, is expected to be computationally challenging and too slow for many use cases. To expedite such queries, some embodiments may implement a data structure by which the query term itself, like lat-long coordinates, index into a subset of the polygons, thereby excluding the vast majority of polygons from the point in polygon computation. In some embodiments, a geographic area may be divided up according to a grid system 120 that may include a plurality of grid squares 122, which may take a variety of shapes other than squares, including rectangles, hexagons in a hexagonal tiling system, triangles in a triangular tiling system, or a variety of other regular or irregular tilings. Irregular tilings may use larger tiles for areas with relatively few places-of-interest, for example in sparsely populated rural areas, to afford more efficient use of memory, in some embodiments.

In some embodiments, each tile 122 may have an identifier or address in a data structure that corresponds to the geographic area it encompasses, and the identifier may correspond to how that geographic area is specified in the query. For example, a given tile 122 may be at an address that corresponds to a point on a space filling curve or a truncated set of lat-long coordinates that excludes less significant digits, such that each appended or hashed set of lat-long coordinates specifies some unit area, like a square kilometer, square meter, or square 10,000 km. Similarly, in some cases, the lat-long coordinates may be truncated to some number of significant digits, excluding less significant digits, converted to a binary number, which may then specify a point on a Hilbert curve or other space filling curve. In some embodiments, these addresses may then contain a pointer to the subset of bounding polygons 124 within the tile 122 that is identified. In some embodiments, each of those bounding polygons 124 may correspond to a place-of-interest, and the bounding polygons may specify the pace place-of-interest with vertices 126 corresponding to latitude and longitude coordinates that are associated with a unique identifier of the place-of-interest in the geographic information system 84. In some embodiments, each place-of-interest may further include a record including the attributes of places-of-interest and corresponding risk scores of geographic places like those described elsewhere herein.

As noted, the geolocation-pathogen-risk scores and personal-pathogen-risk scores may have a variety of uses. In some embodiments, the above-described server system 12 may use one or both of the sets of scores for purposes of human load-balancing at places of interest (e.g., indoor or outdoor places). Some embodiments may obtain or predict a number of people at, or expected to visit, a geographic place of interest, for example based upon currently reported geolocations or the above-describe techniques for predicting future geolocations of individuals. Some embodiments may model geolocation-pathogen-risk scores for the places of interest based upon predicted visits from a collection of people predicted to visit. In some embodiments, the predictions may be weighted based upon confidence in predictions of visits. Some embodiments may use these models to determine how many, or which, people can visit within a duration of time (like one-hour windows, days, afternoons, or the like) without the geolocation-pathogen-risk score exceeding a target threshold. Some embodiments may cause communications to be sent to users that would cause the predicted geolocation-pathogen-risk scores to exceed that threshold if visiting to not visit. For example, some embodiments may suggest people not visit; some embodiments may interface with a reservation server system to instruct the server system to cease granting additional reservations (or to cancel reservations); or some embodiments may send messages to people telling them that they are prohibited from visiting the places. In some embodiments, these human load-balancing techniques may reduce the need for complete shelter-in-place restrictions in geographic areas, by dynamically balancing the load of human beings visiting places of interest, in some cases accounting for the personal-pathogen-risk scores of those human beings.

Some embodiments may allocate capacity at geographic places of interest with various types of bin packing algorithms. Some embodiments may identify a collection of people predicted or requesting to visit a designated place of interest. Some embodiments may obtain personal-pathogen-risk scores of potential visitors, such as likelihood of those people having a designated pathogen or being in a contagious phase of such an infection. Some embodiments may optimize which people visit the place of interest in a designated time. For example, some embodiments may execute a greedy bin packing algorithm in which users are taken in order of identification and time slots are filled until the predicted geolocation-pathogen-risk score would cross the threshold if additional people were added. Some embodiments may apply more complicated algorithms to allocate scarce capacity. For example, some embodiments may mix people who have been vaccinated or have already had a virus with those who are presenting greater risk to increase the number of people who can visit at a designated time slot.

Some embodiments may implement cross-border risk indexing. In some cases, the above-describe server system 12 may compute country-to-country risk scores based upon the exposure risk from people departing a country A (taking into account each person's home address and the city of departure and the corresponding location risk indexes for their home and departing city) and traveling to a country B. In some cases, these risk scores may be modeled as a matrix in which a list of countries corresponds to rows and the same list of countries corresponds to columns, with values indicating the risk of moving from a row country to a column country. In some cases, the same technique may be applied to smaller geographic units, like movement between counties, states, or municipalities. Some embodiments may integrate with a country's customs and border enforcement system or air traffic or ship information system to transmit messages identifying relatively high-risk travelers, such as those scoring higher than a threshold, transiting between countries. In some embodiments, the system 12 may ingest flight manifests, as well as manifests from other modes of travel, like trains, ships, and the like, and create an inbound risk score for people coming into a country. In some cases, these inbound risk scores may be the personal-pathogen risk scores for individuals that are inbound.

Location Pathogen-Risk Index

Figure 4:
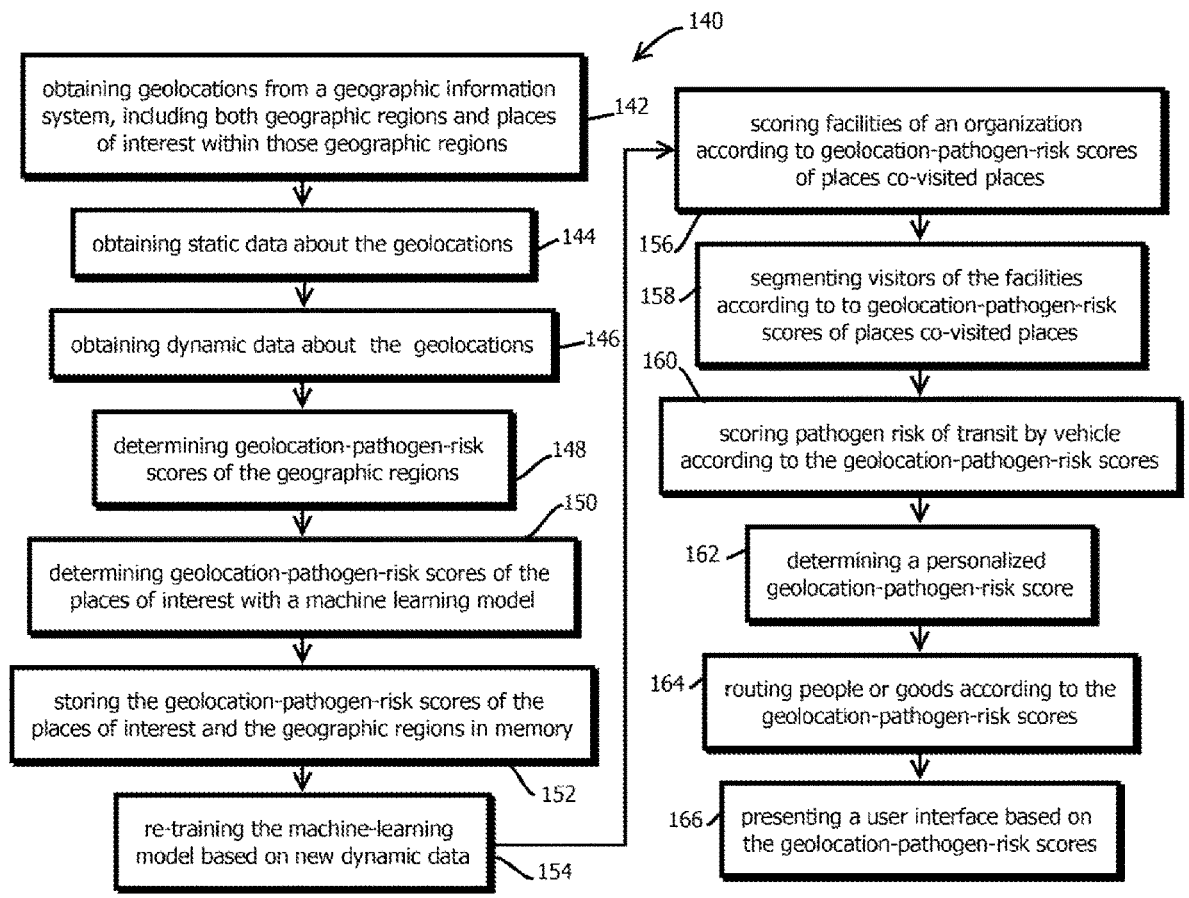
FIG. 4 is a flow chart of an example of a geolocation-pathogen-risk-scoring process that may be executed by the system of FIG. 1.

Some embodiments of the server system 12 may execute a process 140 illustrated in FIG. 4 to analyze pathogen risk by geolocation. In some cases, the process 140 or subsets thereof may be executed periodically, like daily, hourly, weekly or more or less often, or responsive to various events, like updates to the data upon which operations are based. In some cases, the data operated upon may have a relatively large scale, for instance consistent with the examples described above regarding the number of users and geographic coverage. To this end, the techniques described above for expediting processing on large data sets may be implemented, including the approaches related to stream processing and complex event processing systems with compute clusters that implement resilient distributed data sets, in some cases in combination with the machine learning techniques described herein.

In some embodiments, the process 140 may include obtaining geolocations from a geographic information system (like GIS 84), including both geographic regions and places of interest within those geographic regions, as indicated by block 142. In some embodiments, the geographic information system may organize data about geographic areas according to a hierarchical data structure in which some geolocations contain other geolocations which may then themselves contain additional smaller geolocations. In some cases, the obtained a geolocation may be those pertaining to a particular query, like a query specified by the user drawing a bounding box upon a map extent in a user interface, or the geolocations may be a comprehensive set of geolocations in a geographic area or the entirety of the geographic information system, for instance, during operations supplementing a batch process to update risk scores for a country. The geolocations, as indicated may be geographic regions (like reporting districts, such as counties, ZIP Codes, states, parishes, or other geographic areas over which data is to be aggregated, including the other examples described herein) and some may be places of interest (such as businesses, residences, parks, stadiums, and the like, including the other examples described herein). The obtained geolocations may be in the form of identifiers thereof, such as unique identifiers of those geolocations within the geographic information system, and in some cases, the obtained geolocations may include additional attributes of those geolocations, like bounding polygons, names, aliases, unique identifiers in other name spaces, and the like.

In some embodiments, the process 140 includes obtaining static data about the geolocations, as indicated by block 144. In some embodiments, the static data is data that is updated less frequently than the below-described dynamic data. Examples of each include those examples consistent with their properties described elsewhere herein. In some cases, the static data never changes, or in some cases, the static data changes less frequently than once per month, once per year, or once per decade. In some cases, the static data is not pathogen specific, for instance, the static data may remain the same regardless of what pathogen is it at issue. Examples of static data include those examples in the applications incorporated by reference, such examples including census data, data from an organization's identity management or payroll system that indicates which employees or other visitors to the facilities are assigned to which facilities, attributes of geolocations that are independent of pathogen prevalence at those geolocations, and the like. In some cases, the static data may include identifiers of geolocation in a name space or a plurality of name spaces of various sources of the static data (like servers 18), and in some cases the geographic information system may associate identifiers in other name spaces with a native namespace of the geographic information system, correlating a canonical identifier with third-party identifiers. In some cases, the static data may be obtained from third-party data sources, for instance, by querying various APIs exposed by, for example, governmental agencies, universities, real estate records, and the like.

In some embodiments, the process 140 includes obtaining dynamic data about the geolocations, as indicated by block 146. In some embodiments, the dynamic data is updated more frequently than the static data, such as more often than monthly, weekly, daily, or hourly. In some embodiments, the dynamic data is pathogen specific, for instance, pertaining to numbers or per person or per unit time rates of infection, hospitalization, death, vaccination, immunity, of various pathogens and in some cases variants thereof. In some embodiments, the dynamic data includes time series data indicating such values over a trailing duration of time, like since the beginning of a pandemic. The dynamic data may also be obtained, in some cases, from third-party data sources, for instance by querying various APIs exposed by governmental agencies (e.g., the Centers for Disease Control), universities, hospital systems, not for profits, and the like, with additional examples discussed above. In some cases, the dynamic data may include information from the above-described native applications 58, upon users consenting to such use, and upon the information being anonymized, in some cases with differential privacy techniques, or some embodiments may operate without information supplied by individual users of the mobile application, which is not to suggest that any other feature described herein is not also amenable to variation. In some cases, some of the dynamic data may be obtained as a batch download from an API exposed by a third-party server (e.g., servers 18), or some dynamic native data may be received through push communications, for instance, upon registering a callback function with such third-party servers or other applications.

Some embodiments include determining geolocation-pathogen-risk scores of the geographic regions, as indicated by block 148. In some embodiments, scores of the regions may be determined before scores of the places of interest in those regions, or vice versa, in some cases with scores in one being based upon scores in the other. In some embodiments, the scores in the geographic regions may be based on both the static data and the dynamic data. In some cases, the dynamic data is not reported at the level of geographic granularity corresponding to at least some places of interest. In some embodiments, at least some of the dynamic data may be reported, and thus obtained, at lower levels of geographic granularity, for instance, corresponding to the geographic regions. In some embodiments, different portions of the dynamic data may have different levels of geographic granularity. For example, positive test rates for infection or seroprevalence, hospitalization rates, vaccination rates, immunity rates, or accounts thereof, may be reported at the county level from various third-party servers or other data sources. In some embodiments, the static data may be more granular than the dynamic data, less granular, or portions thereof may have this property.

In some cases, the geolocation-pathogen-risk scores may correspond to, for instance, be output by statistical or machine learning models configured or otherwise trained to compute, mean, median, mode, 80th percentile, 95th percentile, or some other representative characteristic of a distribution probability of contracting a corresponding pathogen, being hospitalized due to infection, dying due to infection, missing work or school due to infection, or the like. In some cases, different scores may be calculated for a given pathogen for each of these outcomes. In some cases, different scores may be calculated for different variants of a given pathogen. In some cases, the scores may be independent of behavior or attributes of any one individual, for example, indicating a baseline level of risk designed to be informative to a broad swath of the population, managers, or policymakers. In some cases, the model may be hand coded, for instance, using epidemiological models from the art (e.g., based on SIS, SITR, SIRD, MSIR, SEIR, SEIS, or other models), or in some cases, machine learning models may be trained based upon historical behavior of the pathogen or a collection of pathogens. For example, a machine learning model like that described below for places of interest may also be trained for the geographic regions. In some cases, each of these scores may also be calculated for different segments of time, for example, with different portions of the day (like morning, evening, afternoon, or night, or one hour segments), different portions of the week (like weekdays and weekends, or each week day of the week), or different seasons of the year, indicating different levels of risk based upon different attributes of the geographic region at those times.

Some embodiments include determining geolocation-pathogen-risk scores (for example any of the forms described herein) of the places of interest with a machine learning model, as indicated by block 150. Examples of such models include empirical Bayesian kriging (EBK), EBK with independent variables, ordinary least squares (OLS) regression, geographically weighted regression (GWR), and those described in Du, P., Bai, X., Tan, K. et al. Advances of Four Machine Learning Methods for Spatial Data Handling: a Review. *J geovis spat anal* 4, 13 (2020), the contents of which are hereby incorporated by reference. In some cases, the machine learning model may be trained to allocate risk of geographic areas down to places of interest within those geographic areas, for example, unevenly on to different places of interest (which may include subregions of the geographic areas) based upon attributes of those places of interest, such as attributes in the static data or in some cases the dynamic data where the dynamic data is obtained with sufficient granularity. In some cases, this down projecting of risk may be performed at multiple levels of a hierarchical segmentation of a geographic area, like three, four, five or more hierarchical levels of segmentation, which may include regular tilings like a quad tree or irregular tilings, such as often are implemented in subdivision of geographic areas by municipalities and states. In some cases, some places of interest in the geographic region may be determined by the machine learning model to have a higher risk than other places of interest in the same geographic region based upon attributes of those places of interest. Examples of such attributes include density of people, density of movement, vaccination rates, immunity rates, seroprevalence rates, and the like. In some cases, the scores may also computed for different segments of time according to attributes of the places of interest during those segments of time, like as described above for the scores for the geographic regions. In some cases, places of interest may include hyperlocal places of interest, such as those that are smaller than 1000 m$^2$, 2000 m$^2$, or 5000 m$^2$. In some cases, the places of interest may further be segmented by floor or room of a building (which may themselves be places of interest), like a multistory building, with different floors or rooms therein having different scores. In some cases, the scores may be based upon the self-reported attributes of the buildings discussed above, with things like open-air flow and robust ventilation or clean schedules tending to drive down risk in rooms, floors, or buildings in which those attributes apply.

The machine learning model may take a variety of forms in addition to (and in some places in combination with, like in an ensemble model, the examples above). Examples include decision, regression, or classification trees, or ensembles thereof, like random forest machine learning models. Some embodiments may input a plurality of features pertaining to the place of interest, such as the types of attributes described above of such places of interest, like five or more features, 10 or more features, or 50 or more features. In some cases, these features may define an input feature space having a corresponding number of dimensions. Some embodiments may implement binary recursive partitioning, e.g., some such embodiments may iteratively bisect respective dimensions of that feature space in each iteration, testing different locations to bisect on the respective dimension to select the location on that dimension (and in some cases the next dimension to bisect) that minimizes entropy or Gini impurity in the volumes on either side of the value in the respective dimension. In some cases, the entropy or Gini impurity (which may be generically referred to as a measure of impurity) may indicate which weight (or a linear segment of a weight curve or planar weight surface) in a range of discrete weight values best characterizes allocation of risk from geographic regions to places of interest in historical data at the corresponding volume in the input feature space. In some cases, the splits may be determined with a greedy optimization that optimizes for minimizing such measures of impurity at each iteration. Some embodiments may further implement pruning to reduce the risk of overfitting, e.g., by thresholding according to a cost complexity factor.

In some cases, the machine learning model may take the form of a deep neural network operative to transform inputs into a corresponding output weight. For example, the deep neural network may include a plurality of layers of perceptrons having connections (by which outputs flow to inputs) therebetween with parameters adjusted during training referred to as biases and weights (which are different from the weights output by the model) for each perceptron. In some cases, the number of parameters of the model adjusted during training may be greater than 1000, 5000, 10,000, or 50,000, and the model may be said to have a corresponding number of degrees of freedom.

In some cases, training may be implemented with stochastic gradient descent using back propagation. In some cases, training may include iteratively computing a partial derivative of each of the respective parameters of the model adjusted during training with respect to an objective function, indicating a local slope that indicate a direction to adjust the parameter according to some stride value that may be a hyper parameter to locally further optimize the objective function. In some cases, the objective function may be a fitness function indicating how well the model (at a current iteration of training) characterizes relationships in a training set or a loss function indicating how poorly the model (at a current iteration of training) characterizes such relationships. In some cases, training may be repeated multiple times by selecting random initial values for the parameters during each training repetition to reduce the risk of landing in a local minimum, and the training repetition producing the most optimal outcome of the objective function may be selected as the trained version of the model. In some cases, training iterations may repeat until a change in the objective function between successive iterations is less than a threshold value, indicating a minimum or maximum.

In some cases, some training data may be withheld from training and use to cross validate the train models by testing the train models on the withheld training data and computing a value like an F-score. Some embodiments may determine whether this score satisfies a threshold (for example is greater than the threshold for values that tend to increase with quality or is less than the threshold provides the tend to decrease with quality). Some embodiments may also implement techniques like bootstrap aggregation to further extend the value of training sets, with some training examples occurring in multiple training repetitions, for example, by randomly selecting from a training set to form batches, for instance, either with or without replacement, each batch being a subset of the training set, and each batch used to train a repetition of training.

In some cases, the resulting weights output by the models may be normalized, e.g., over the geographic region at issue. For example, some embodiments may divide each of the weights by a sum of all of the weights to produce a coefficient. Or in some cases, this sum may include additional values to reflect regions for which weights were not obtained for places of interest. In some cases, the resulting coefficients for all place of interest in a region may sum to one. Some embodiments may then multiply the coefficient of each place of interest by the geolocation-pathogen-risk score of the corresponding region to produce the down projected geolocation-pathogen-risk score of the respective place of interest.

Some embodiments include storing the geolocation-pathogen-risk scores of the places of interest and the geographic regions in memory, as indicated by block 152. In some cases, these values may be stored in persistent or dynamic storage, for example, in program state or written to disk or a solid-state drive in a database, like in the geographic information system in a record corresponding to each of the geolocations to which the scores apply. In some cases, these scores may be computed at query time, when a query is received by the geographic information system requesting such scores, or the scores may be computed periodically or responsive to some event as a batch process, for instance, for all geolocations characterized by the geographic information system.

The stored scores may have a variety of uses, some examples of which are described above, and some of which are illustrated in FIG. 4. These operations, like the steps of the other processes described herein, in some cases may be omitted in some embodiments, which is not to suggest that any other described feature is required in all cases.

In some embodiments, the machine learning model or models may undergo active learning. In some cases, this may include retraining the machine-learning model based on new dynamic data, as indicated by block 154. Some embodiments may perform a full retraining operation, or some embodiments may initialize the retraining model to the parameters of the existing model, using a training set that reflects newly arrived data. In some cases, retraining may include training a new model downstream of the existing model that learns to correct error in the existing model when the existing model is used to predict outcomes in the new training data.

Some embodiments include scoring facilities of an organization according to geolocation-pathogen-risk scores of places co-visited by those visiting the facilities or expected to visit the facilities. For example, an employer, like a corporation or governmental entity, may maintain an account in the server system 12 indicating which places of interest are facilities of that entity, and in some cases, that entity may query the server system 12 for a reporter indicating such scores. In some cases, the risk scores may reflect behavior of people who visit the facilities or are expected to visit the facilities, such as places where those people reside, travel, or work outside of the facilities (or similar attributes of people adjacent those facility visitors/potential-visitors in a social graph).

In some cases, those predicted to visit a facility may be obtained by querying a calendar or scheduling software or customer relationship management or enterprise resource planning system, for instance, for scheduled visits by customers, contractors, or vendors. In some cases, those who visit or are predicted to visit may also be obtained from payroll systems or identity management systems of the entity. In some embodiments, the information about such individuals may be stripped of personally identifying information and may be anonymized or rendered pseudonymous in information sent to the server system 12. In some embodiments, operation on such information may be executed in a federated manner, with code running within computing devices owned or controlled by the entity operating the facilities based upon geolocation risk scores reported by the server system 12 before aggregate outcomes are reported back to the server system 12, thereby reducing the entity's cybersecurity attack surface for those seeking to obtain private information about those who visit the facilities. Or some embodiments may report this information back to the server system 12, for instance conveying the information in encrypted format in appropriately anonymizing records.

In some cases, embodiments may obtain other geolocations visited by those expected visit or who have visited the facilities, like residences of employees, and determine a risk score for the facility based upon geolocation-pathogen-risk scores of those residences or regions of those residences. For example, if a subset of employees visiting a facility reside in a relatively high-risk area, that information may tend to increase the facility risk score. In some cases, lower granularity characterizations of co-visited places, like residences, may be used to enhance privacy and limit access to the server system 12 of individuals private addresses. In some cases, the facilities geolocation-pathogen-risk score may be a measure of central tendency (for example mean, median, or mode) of the scores of the co-visited places, a visit duration or frequency weighted version of such a measure of tendency, a worst-case or greater than a threshold percentage (like 90th percentile highest risk) risk score of co-visited geolocations, or a visit duration or frequency weighted version of such a score. In some embodiments, a given person may co-visit a variety of different geolocations, and multiple co-visited geolocation risk scores may be accounted for when processing information corresponding to that information that individual. Or in some cases, a machine learning model like those described above may be trained to predict facility risk scores based upon the co-visited place's geolocation-pathogen-risk scores.

In some cases, the visitors, either current or expected, of the facilities may be grouped according to their risk contributions. For example, some embodiments may segment visitors of the facilities according to geolocation-pathogen-risk scores of their co-visited places (e.g., previous places they visited), as indicated by block 158. In some cases, the segments may be referred to as risk pods. In some embodiments, these risk pods may be relative segmentations, like top half and bottom half of risk, or absolute segmentations, like those with greater than a 10% chance of infecting others, the those with greater than a 50% chance of infecting others, and those with greater than a 90% chance of infecting others (or risk of being infected, risk of being hospitalized, or risk of dying). In some cases, these segments may be presented in reports to management of such organizations, like those running schools (e.g., students co-visits may affect risk of a school facility), governmental agencies, or corporations or not for profits. In some cases, the segments may be presented without identifying individuals in the segments in the report, but indicating group statistics, like a number of people in the segment. In some cases, the user interface with which the information is presented, for example, in a computing device of those in management, may further include a user input to select or otherwise request communications to some of the groups produced by the segmentation, for instance, causing an email, text, or push notification to be sent to those in a relatively high risk segment, instructing them to not come to the facility and work from home, or a similar type of communication to those in a low risk segment, informing them that the risk has been analyzed and they are clear to come to work and that those in higher risk groups have been asked to not come to work. In some cases, such communications may be conveyed via the above-described mobile application, or communications may be sent to other network addresses, like email and phone numbers for text or audio messages, or via social media feeds of users.

In some embodiments, the user interface presented to management of facilities may also indicate the geolocation-pathogen-risk scores of those facilities computed based upon the scores of co-visited places. In some embodiments, the user interface (which like the other user interfaces described herein, may evolve over time to reflect different information and respond to user inputs while still constituting "the" user interface, that is an antecedent of the term "the user interface" may display different information that that presented when "the user interface" is subsequently referenced) may depict a map of the facilities, with color coding or other visual weight applied to indicate risk of the facilities. For example, a spectrum of color may be scaled according to a range of risk scores, and facilities with particular risk scores may have corresponding colors applied in the user interface. In some cases, the user interface includes event handlers responsive to user selection of individual facilities (for example clicking on, touching, gazing at, or the like) to update the user interface to depict additional, more detailed information about those facilities, like which geographic regions account for which portions of the risk, a depiction of the segments of visitors to that facility according to the above-describe segmentation according to risk of visitors, or some other characterization of the distribution of individual contributions to the risk to help inform decision-making.

Some embodiments include scoring pathogen risk of transit (e.g., trip) by vehicle (e.g., ship, train, subway, bus, car, plane, etc.) according to geolocation-pathogen-risk scores, as indicated by block 160. Examples include scoring transit in vehicles in which multiple people are conveyed concurrently. In some cases, a manifest indicating which people are all to be conveyed may not be available, and some embodiments may score pathogen risk of transit based upon the departing geolocation, for instance indicating high risk for plane flights from a region with a high infection rate. In some cases, manifests may be available, for example, indicating anonymized or pseudonymous identifiers of those traveling and, in some cases, previous places those individuals have traveled. Some embodiments may score the transit according to those previous visits in the manner described above where visitors to a facility contribute to risk according to co-visited places of those individuals.

Some embodiments may determine a personalized geo-location-pathogen risk score, as indicated by block 162. In some cases, the server system 12 or native application 58 may cause individuals to be presented with customized messages to reduce their risk of pathogens. Some embodiments may determine some measure of a user's responsiveness to those messages, like a response rate or risk severity weighted response rate. Based upon this measure of responsiveness, some embodiments may determine the personalized pathogen risk score of the individual for the geolocation, with those that tend to be less responsive to messaging being presented with a higher score. In some embodiments, users may input an enhancement factor during the onboarding process or by configuring settings in the native application 58, such as a personalized risk scaling preference to indicate that they wish to be particularly cautious (or less cautious), and those individuals may be presented with a personalized geolocation-pathogen-risk score that is scaled (or offset) upwards or downwards based upon that setting, with other operations that depending upon that score particular to the user being similarly modified.

Some embodiments may include routing people or goods according to the geolocation-pathogen-risk scores, as indicated by block 164. In some cases, this may include monitoring and adjusting a logistical supply chain to reduce pathogen risk. For example, some pathogens may have fomite transmission and goods from areas with the pathogen may tend to cause its transmission, and suppliers in regions with high risk may tend to be less reliable. Some embodiments may obtain a sequence of geolocations in such as supply chain or travel route for an individual. Some embodiments may determine or obtain a plurality of alternate sequences of geolocations corresponding to different vendors or facilities in supply chain or different routes of travel. Some embodiments may obtain geolocation-pathogen-risk scores of each geolocation in each of the sequences of the different routes, and some embodiments may determine an optimal or reduced risk route to select among those candidates. In some cases, the candidate geolocations along the various routes may be represented as nodes in a graph with directed weighted edges indicating risk of goods or people leaving that node. Some embodiments may further weight the edges based upon cost, distance, or transit time to produce a risk-adjusted weight corresponding to goods or people leaving the respective node to go to subsequent nodes in a sequence. Some embodiments may compute a path across the graph (e.g., from a starting node or candidate nodes to a destination node) that minimizes the risk-adjusted score or keeps each edge along the path at less than a threshold pathogen risk. The resulting path may be selected, or a risk-ranked listing of such paths may be presented in the user interface for users to select among to reroute goods or people.

Some embodiments include presenting a user interface based upon the geolocation-pathogen risk scores, as indicated by block 166. Examples of such user interfaces are described above. In some embodiments, the user interface may include a map (e.g., a scalable and pannable map) depicting a map extent, and the user interface may be responsive to (for instance with user input responsive event handlers) user inputs to select an area of the map, for example, by drawing a bounding box. Some embodiments may receive the selection and query the geographic information system 84 for geolocation-pathogen-risk scores of geolocations within the area designated by the bounding box. Some embodiments may update the user interface to depict these risk scores, for instance, using the above-described color coding scheme. In some cases, the user interface may be responsive to user selection of individual places of interest or geographic regions to update the user interface to depict a time series depiction of the geolocationpathogen-risk score of the selected geolocation, for instance, since the beginning of a pandemic (or to show a predicted trend for such a score), and in some cases, depicting the relative contribution of subregions, like places of interest, to the aggregate score of the selection, for example, using the above-described color coding schema. In some cases, the user interface may be presented in a web browser of a remote user's computer or in the above-described native application 58, each through communication with the server system 12 via network 26, or in a computer executing the code described above with reference to the system 12, for example in a monolithic implementation.

In some embodiments, the process 140 may include producing results useful for policymakers, like indications of which static or dynamic data tends to drive or correlate with various outcomes (like infection, hospitalization, loss of work days or school days, vaccination, death, or the like). For example, some embodiments may use principal component analysis, multi-variate analysis, dynamic Baysean networks, do-calculus, or other statistical techniques to determine which static variables or types of messaging or policy choices correlate with, or cause, changes in geolocation-pathogen-risk scores or these other outcomes. Some embodiments may use machine-learning models designed to be interpretable to output results indicating which input features or intermediate-layer features exhibit correlation with outcomes. In some cases, these outputs may be presented in a report in a user interface on a policymaker's computing device through communication with the server system 12 via network 26.

Behavior Modification Messaging

Figure 5:
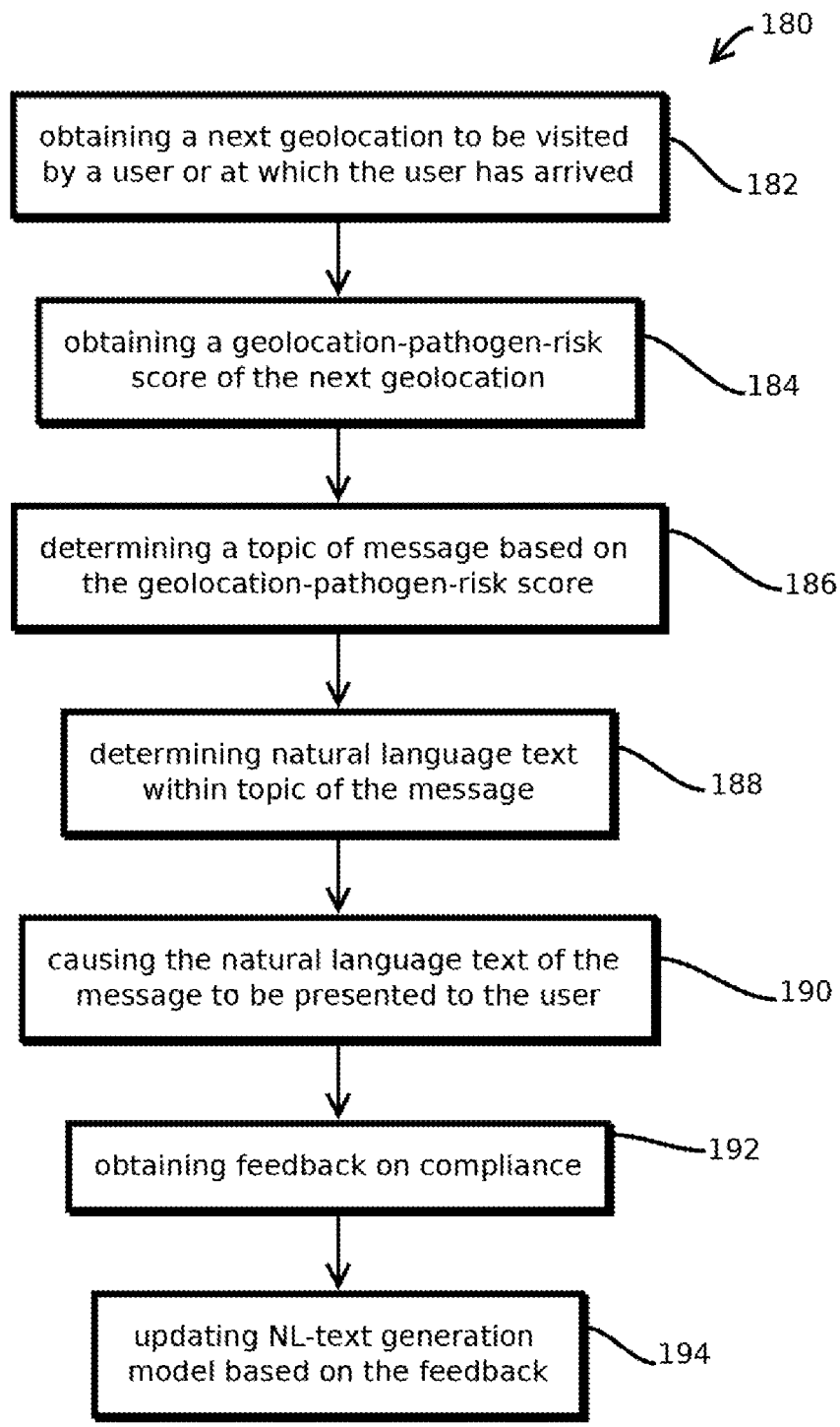
FIG. 5 is a flowchart illustrating an example of a behavior modification messaging process in accordance with some embodiments of the present techniques.

Some embodiments implement a behavior modification messaging process 180 illustrated in FIG. 5. In some embodiments, this process 180, or portions thereof, may be executed responsive to events in real time (for example within less than one minute, less than five seconds, or less than 500 ms, of receiving an event prompting execution). In some cases, the process 180 may be initiated responsive to an event indicating a user is predicted to visit a geolocation, for instance with the techniques described above, like based on API access to user calendars, inferred next locations determined with machine learning models, like long short term memory networks or hidden Markov models, or the user expressly indicating through use of the native application 58 that they intend to travel to a geolocation. Or in some cases, the process 180 may be executed responsive to a determination that the user has arrived at a geolocation, for instance, crossed a geo-fence corresponding to a geolocation, their mobile device 14 has sensed a wireless beacon broadcast at the geolocation, or the user has expressly indicated that they are at the geolocation through input to the native application 58. In some cases, the process 180 may be executed as a batch process, for instance, hourly, daily, or weekly.

In some embodiments, the process 180 may be executed by the server system 12, for example by the natural-language-text generation model 79 or in cooperation with that model, for example, at the direction of controller 74, as shown in FIG. 1 above. In some embodiments, the server system 12 may include a finite state machine 81 that implements organizational messaging to manage pathogen risk, as described in greater detail below with reference to FIGS. 6 and 7.

In some embodiments, some operations may be performed by the mobile computing device 14, for example, by the native application 58. Like the other processes described herein, the computer system implementing this process 180 may be solely constituted by the server system 12, solely constituted by the mobile computing device 14, or a combination thereof, for example in distributed applications, or some embodiments may rely on third-party computing hardware as well.

In some embodiments, the process 180 begins with obtaining a next geolocation to be visited by the user, or at which the user has arrived, as indicated by block 182. In some cases, this step of obtaining step may be implemented by obtaining an event like those described above indicating such an occurrence. In some cases, the next geolocation may be obtained from mobile device 14, and the next geolocation may include, or map to (e.g., in a one to one or one to many relationship), a record that is stored in, and retrieved from, the above-described geographic information system 84. In some embodiments, the next geolocation may be obtained as part of a sequence of geolocations the user is visiting, has visited, or is expected to visit. In some embodiments, the user may have only visited a subset of the sequence and some geolocations in the sequence may be predicted. Or in some cases all geolocations in the sequence may be predicted.

In some cases, where the user has already arrived at the geolocation, step 182 (like 182 to 190) may be performed within a relatively short duration of time of arrival, for instance within less than 20 minutes, like less than five minutes or less than one minute of arrival. In some cases, arrival may be detected by the native application 58, upon receiving an event are function callback from a geolocation framework executed by the mobile computing device 14, for instance, provided by the operating system 56 (like a corelocation framework in iOS™ or CLLocationManager framework in Android™) indicating such arrival. In some cases, where a sequence of geolocations is obtained, both the geolocations and dwell times thereof may also be obtained to produce dwell-duration weighted scores.

Some embodiments include obtaining a geolocation-pathogen-risk score of the next geolocation, as indicated by block 184. In some cases, this may also include obtaining geolocation-pathogen-risk scores of each geolocation in a sequence of geolocations visited or that are to be visited. In some embodiments, the score may be obtained by querying records corresponding to the geolocations in the geographic information system 84, which may be stored there in advance by executing the process 140 of FIG. 4. Or in some cases, the scores may be updated in real time by executing some or all of the process 140 (or the scores may be created for the first time if they do not exist by executing process 140, e.g., within less than 5 seconds, like within 150 ms). Or in some cases, the scores may be obtained from a third party.

In some cases, messages presented to users may be rate limited, to avoid overwhelming users and messages losing salience. For example, some embodiments may limit the number of messages presented to a user to less than some threshold per trailing duration of time, like two per 24 hour period of trailing duration, or two per day. In some cases, this threshold may be modulated based upon the risk score, for instance, some embodiments may determine to permit a third message in this example upon determining that the risk score exceeds some threshold, and some embodiments may extend that to a fourth message upon determining that the risk exceeds some even higher threshold.

Some embodiments include determining a topic of message based on the geolocation-pathogen-risk score, as indicated by block 186. In some cases, the message may be based upon the scores for a sequence of geolocations, for instance, based upon a maximum score, a duration weighted average score, an average score, a 90th percentile or some other threshold score or the like. In some cases, ranges of geolocation-pathogen-risk scores (or ranges of types of such scores) may be modified by users specified factors that indicate a user's preference for being particular risk adverse or risk tolerant, like those discussed above. In some cases, ranges of such scores may further be modified based upon a user's pattern of complying with behavior modification messaging, for instance, with personalized geolocation-pathogen-risk scores like those discussed above.

In some embodiments, ranges of such scores may be mapped to topics, and in some cases first or second derivatives of such scores with respect to time or sequence of geolocations in a sequence may be computed and ranges of those derivatives may also be mapped to topics. Examples of topics include warnings of high risk, all clear signals, warnings of increasing risk, warnings of accelerating risk, warnings to take risk mitigating actions, indications that risk mitigating actions can be reduced, and the like.

In some cases, each topic may correspond to a larger body of candidate specific natural language expressions of messages within that topic. For example, the "warning of increasing risk" topic may apply both to a natural language text message that "risk is increasing rapidly over the last two weeks for pathogen X at your next geolocation Y" and a natural language text message that "risk of infection is trending upward here."

In some cases, these natural language text messages in each topic may be prewritten, for instance, with more than 5, more than 50, or more than 500 in a corpus segment for each topic. In some cases, those messages may be implemented as templates, with fields that are populated to customize the message for a given context or person, consistent with examples described below. Or in some cases, the messages are generated without a template, for instance, from scratch by certain embodiments of the natural-language-text generation model 79 described below. In some cases, these candidate bodies of text, or inputs to produce those candidate bodies of text, and models relevant thereto may be part of the natural-language-text generation model 79 shown in FIG. 1.

Some embodiments may determine with a natural-language-text generation model, natural language text within the determined topic, as indicated by block 188. In some cases, this may include selecting among pre-written bodies of text, each corresponding to a different expression consistent with the topic. Examples include randomly selecting among bodies of natural language text in a corpus that are mapped to the topic in advance. In some cases, the probability of selecting various candidate messages in such a corpus for topic a may be modified based upon feedback, such that those messages tending to produce more compliance are more likely to be selected, but without repeating the same message again and again with excessive frequency.

For example, each such candidate message may be mapped to a range of integers between 0 and 10,000, and the size of the range mapped to each candidate message may be selected in accordance with the feedback, such that feedback indicating compliance tends to widen the range, and feedback indicating the absence of compliance tends to narrow the range. Some embodiments may then select a random number, like a pseudorandom number, between zero and 10,000 and then select the message text assigned to a range including that random number. In some cases, different ranges corresponding to different probabilities of being selected may be computed based upon feedback according to demographic or psychographic segment of those to which the feedback pertains, thereby making certain messages that tend to work well with a certain demographic, for example, more likely to be selected to be presented to other members of that demographic. In some cases, when the message is to be determined, the range corresponding to the user's demographic or psychographic segment (which may be determined with techniques discussed below) may be used to compare to the random value that drive selection among those messages pertaining to a topic in the corpus. In some cases, selections may be rejected or candidates may be withheld from the selection based upon those messages having been presented to the user within some trailing duration of time or trailing number of messages in a sequence of messages sent to that user, to avoid having repetitive messages sent to the user.

In some embodiments, the corpus of candidate messages may include templates having fields that can be customized for a context or person. In some embodiments, these fields may be mapped to queries to user profiles or other indicia of context, like weather, attributes of the place of interest, time of day, previous places or subsequent places in a sequence of places, a category of place being visited, or category of activity to be engaged in at the place to be visited. Some embodiments may maintain an ontology of places, like a hierarchical ontology and an ontology of activities, like a hierarchical ontology of activities. Examples include such an ontology indicating the category of restaurants includes the subcategory of Italian restaurants, which includes a sub-subcategory of northern Italian restaurants, which includes a specific place of interest to be visited. Similarly, some embodiments may include the activity of sports, which may include sub-activity of golf, which may include golf at a particular place of interest. In some cases, these ontologies may be interrogated to identify alternative activities or places of interest (e.g., other exemplars in the same category as the next geolocation) to include in fields in templates or otherwise indicate in messages generated for users to propose safer alternatives.

For example, some embodiments may rank alternatives according to geolocation-pathogen-risk scores of those alternatives and present those having greater than a threshold ranking. In some cases, the ranking may also be based on travel time or distance, for instance, with risk-weighted distance or travel time, and again those options above a threshold ranking may be presented to the user via the native application 58, in some cases with a link to navigation directions or a website or other profile of the alternative activity or place of interest, like a timeline of the places geolocation-pathogen-risk score.

In some cases, the templates may include fields about the user, like age, health status, comorbidities, goals or risk preferences entered into the native application 58, compliance rates, or the like. In some cases, this information may be stored exclusively client-side, in memory of the native application 58, and templates may be populated in part or entirely on the mobile computing device 14, by the native application 58 by querying values from memory to populate these fields. In some cases, some fields with less sensitive information may be populated by the server system 12 before a partially populated template is sent to the mobile computing device 14. For example, a template may state "please be careful. Someone with {insert query result for highest-ranking comorbidity of user} should be particularly careful about visiting this place due to risk of infection," with the text in brackets being inserted client-side, before the fully populated template is presented as a text warning to the user. Or in some cases, users may consent to have their information stored in encrypted format, with otherwise anonymous identifiers, server-side, and fields may be populated in templates before those templates are sent to the mobile computing device 14.

In some cases, templates or other messages may be formed based upon information drawn from a social graph of the user. Some people may want to be particularly careful about their risk of giving a particular pathogen to someone in their social graph or within some threshold number of degrees of connection in their social graph. In some cases, the social graphs may again be stored client-side and operations thereon may be performed client-side, for example, to populate templates or to select among candidate natural language text for messages. (It should be emphasized that natural language text may be embedded in, or referenced by, structured text while still qualifying itself as natural language text.) For example, some embodiments may recursively traverse a social graph of the user to some threshold depth and determine whether any other users within that range have greater than a threshold risk for each of a plurality of pathogens, like risk of death, risk of hospitalization, or the like.

Upon determining that some users within the threshold range of connections in the social graph present such risk, in response, some embodiments may populate a template to indicate something like "more than three people you know (or that are friends with people you know) are particularly vulnerable to pathogen X, and the risk of infection of pathogen X at the next place you plan to visit is particularly high and trending upward." In some cases, users may be reminded of risk of particular people in their social graph, like family members that are vulnerable, for instance, with fields populated with client-side operations performed by the mobile computing device 14 executing the native application 58, to prevent the need to store sensitive family information server-side, though embodiments are also consistent with that server-side approach when appropriate consent is obtained and anonymization is applied.

In some embodiments, the natural-language-text generation model may generate text expressions of less than 50 or 500 words to provide relatively concise warnings or other advice. In some embodiments, other forms of content may also be selected or otherwise generated with the described techniques, like images or audio conveying the described types of information. Examples of information presented the user may include the following: advise the user of pathogen risk associated with a geolocation; advise the user of pathogen risk associated with a sequence of geolocations visited, or to be visited, by the user; advise the user of alternative geolocations with lower pathogen risk in a same category of geolocation as the next geolocation; advise the user of pathogen-risk-reducing steps to be taken to reduce infection risk; advise the user of an increase in pathogen risk in a geographic region and steps to be taken to reduce infection risk; advise the user to get vaccinated; advise the user of an activity they could engage in upon being vaccinated; advise the user to wear a mask; advise the user to shelter in place; advise the user that their pattern of behavior presents less than a threshold risk of infection; and advise the user that their pattern of behavior presents greater than the threshold risk of infection. Or embodiments may include at least 1, 2, 3, 4, 5, 6 or more or fewer of these, in any permutation.

In some embodiments, the natural-language-text generation model may be operative to generate natural language text from whole cloth, for instance with the GPT-3 model, or various other generative models, like generative pretraining transformer natural language text models. In some cases, the natural-language-text generation model may be responsive to text sent back in response to messages, from users, like generative or retrieval-based chatbots. Some embodiments may implement models like various Seq2Seq models, such as forms of BERT.

Some embodiments may include causing the natural language text of the message to be presented to the user, as indicated by block 190. In some cases, this may include accessing a third-party service, like Firebase Messaging Service™ or Apple messaging Service™ to determine a network address at which the mobile device is accessible based upon the mobile device maintaining an updated record of such network address with the third-party service, for instance, by operation of the operating system, to reduce application-specific battery consumption of such operations and avoid having, for example, 20 different applications executing on the mobile computing device making the same types of updates to different services. In some cases, a push notification may be sent to the native application 58 for presentation on the mobile computing device 14 or for conveyance by the mobile computing device 14 to some other computing device, like a wearable computing device, such as a smart watch, or headmounted display, like an augmented reality display in augmented reality glasses. In some cases, the message may be conveyed as a text message, as an email, or as a post on a social media account. In some cases, the message may be conveyed via audio, for instance, by converting the message into audio with the text-to-speech model (e.g., DeepSpeech or Wav2letter) operated by the server system 12 and playing that audio through a phone call or via a smart speaker of the user having installed thereon an instance of the native application 58, like a "skill" in the Amazon Echo™ ecosystem. Similar techniques may be used to cause messages to be presented by smart appliances, like smart televisions, set-top boxes, in-dash automotive computing systems, and the like. In some cases, messages may be written to a patient record in an electronic medical record system for the doctor to conveyed the patient.

Some cases, the process 180 may cause messages to be sent to a relatively large number of users, at a relatively large scale, with relatively little repetition among messages received by anyone user. For example, some embodiments may be operative to generate over 1000, 10,000, or 100,000 different messages having different content. In some cases, these messages may span more than 5, more than 10, more than 20, or more than 50 different topics, and they may be customized for a population of users over a geographic area having scales like those described above.

In some embodiments, the process 180 may include obtaining feedback on compliance, as indicated by block 192, and some embodiments may include updating the natural anguish text generation module based on the feedback, as indicated by block 194. In some embodiments, the user may expressly provide that feedback, for example by selecting an input displayed along with the message by the native application 58 indicating whether they intend to or have complied or relevance of the message to their current situation. In some cases, the native application 58 may monitor whether the user traverses a geo-fence indicating that the user complied, for instance, that they went to a high-risk geolocation or went to another alternative lower risk geolocation. In some cases, these indicia of compliance may be buffered by the native application 58 over time and aggregate scores (or values with noise injected, like by using differential privacy techniques) may be reported back to the server system 12 that do not indicate whether the user in the visited any one particular geolocation. For example, an average rate of compliance over a trailing duration of three or five messages may be computed and reported. Or in some cases, these values may be determined server-side. In some cases, compliance may be inferred from the person later indicating that they contracted a pathogen in input to the native application 58.

In some embodiments, the feedback may be used to adjust the ranges described above by which message text is probabilistically selected. In some embodiments, feedback may be used to adjust other parameters of the natural language text model, for example, in other types of models. Some embodiments may implement a reinforcement learning model to select or otherwise determine messages in a sequence of messages presented to a user over time. In some embodiments, the reinforcement learning model may implement a policy and a value function, like a deep reinforcement neural network model with such a policy or value function implemented as a multi-layer network of perceptrons. Such models may be trained with the techniques described above, for example, with stochastic gradient descent, using the other approaches described above to increase the robustness of the models. In some embodiments, the value function may be configured to determine semantic similarity of messages, for instance, with an encoder model operative to transform messages in natural language into vectors in an embedding space (e.g., with word2vec, or paragraph2fec), where vector distance in the embedding space indicates semantic similarity. Some embodiments may compute this distance and penalize or otherwise devalue subsequent messages within threshold similarity distances, e.g., with the value function. In some cases, the threshold similarity distances may increase as time passes or as a number of intervening messages have been provided to the user. In some cases, the reinforcement learning model may be a to stochastic reinforcement learning model or a deterministic model. Some embodiments may train the model on historical data of the user, and some cases along with psychographic or demographic attributes of the user, and in some cases with similar values of a population of other users to select messages that tend to increase compliance, reduce infection rates, reduce hospitalization rates, or the like.

Some embodiments may implement A/B testing or other types of testing of larger set of candidate messages. Some embodiments may cause different messages to be sent to different users or sample sizes of populations of different users and determine efficacy of the candidate messages based upon the feedback. Some embodiments may then adjust the natural-language-text generation model to increase the likelihood of those messages exhibiting greater compliance being presented to users. In some cases, this testing may account for psychographic or demographic attributes of users. For example, users may be organized into cohorts or other groups by clustering users according to psychographic or demographic attributes. Some embodiments may use another encoding model trained to represent users in an another embedding space with 5 or more dimensions based upon 10 or more psychographic or demographic attributes of the users. Some embodiments may execute a density-based clustering algorithm (e.g., DB-SCAN) to group users in the embedding space and then segment groups of users to test different versions of messages on the similar topics for the same topic for efficacy in compliance.

Behavior Modification Messaging for Organizations to Reduce Pathogen Risk

Figure 6:
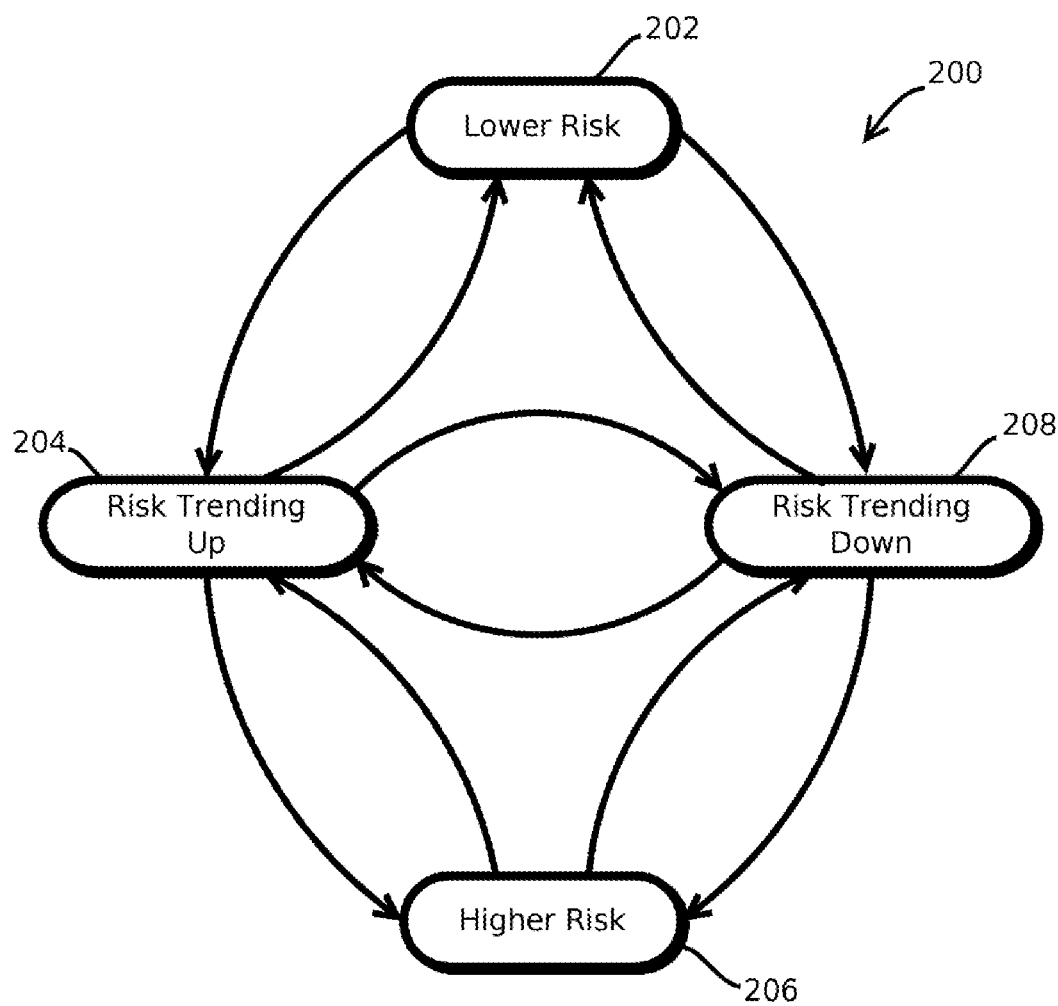
FIG. 6 illustrates states of a finite state machine consistent with some embodiments of the present techniques.

In some embodiments, the server system 12 includes a finite state machine 81 that has the states illustrated in state diagram 200 shown in FIG. 6. In some embodiments, depending upon the state of the state machine, different categories of organizational messaging may be proposed to management to guide pandemic or other pathogen risk mitigation measures among participants of an organization led by such management or other leaders. Such organizations may include corporations, not-for-profits, other business entities, armed forces, schools, and the like.

One state machine 81 and corresponding state diagram 200 are shown, but embodiments are consistent with substantially more. For example, each organization having a tenant account in a multitenant software-as-a-service implementation of the server system 12 may have a corresponding independently operating state machine 81 with the states in the diagram 200. In some cases, each facility may have such a state machine for the organization, where organizations have multiple facilities in some cases. In some embodiments, there may be a state machine 81 specific to each shift or department within a facility or floor of a facility. In some embodiments, there may be one such state machine for each of multiple pathogens, for each type of geolocation-pathogen-risk score, for each shift, for each floor, for each department, for each facility, for each tenant of the multitenant SaaS application (on some embodiments may run on-premises or in a hybrid architecture).

In some embodiments, the state machine 81 includes a state 202 corresponding to lower risk, which may correspond to the geolocation-pathogen-risk scores of the various types discussed above for the facility or organization at issue. Transitions may be determined periodically, like daily, or hourly, or more or less often, or responsive to events, like a request for an update or new data potentially affecting state.

The terms lower and higher do not require some absolute reference by which lower and higher are measured, but rather reference each other, with things referred to as lower being lower than things referred to as higher, and vice versa. Thus, use of the term should not be read as indefinite.

In some embodiments, the finite state machine 81 may transition to the lower risk state 202 upon a determination that a geolocation-pathogen-risk score for the facility or collection of facilities at issue (e.g., an average) is less than a threshold (or like the other threshold determination herein, otherwise satisfies the threshold, for instance, if it is higher than a threshold, where increasing score corresponds to lower risk). In some cases, the finite state machine may transition to or from the state 202 to or from states 204 or 208, depending upon whether risk is trending up or down, respectively.

In some cases, these trends may be determined with a first derivative (which may be an approximation and does not require a differentiable function represent the data) of geolocation-risk-scores of facilities or collections thereof at issue with respect to time. A transition may be triggered upon that first derivative being determined to be higher than one threshold or lower than another threshold to move to or from states 204 and 208. In some embodiments, the finite state machine 81 may also be configured to transition between the states 204 and 208, for instance, when risk scores oscillate over time.

In some cases, the finite state machine 81 further includes a state 206 corresponding to a higher geolocation pathogen risk of a facility or collection of facilities at issue. In some cases, the finite state machine 81 may transition to or from this state 206 or to or from states 204 or 208 upon determining that the geolocation pathogen risk for the facility or collection of facilities at issue is greater than a threshold. In some cases, the finite state machine 81 may include additional states corresponding to additional gradations of risk (e.g., three, five, ten, or more), and in some cases, each of these additional states may include transitions that pass through the trending up and trending down states 204 and 208. Some embodiments may further include additional states corresponding to a second derivative of geolocation-pathogen-risk scores with respect to time, corresponding to scenarios in which risk is accelerating up or down.

In some embodiments, each of the states 204 through 208 may have respective data and logic by which messaging to participants in an organization and guidance to leadership of an organization is implemented consistent with the corresponding state. In some cases, messages may be proposed based upon the process 180 of FIG. 5 discussed above, using the geolocation-pathogen-risk scores determined with the process 140 in FIG. 4 discussed above. In some embodiments, the types of messaging and guidance may correspond to the following examples for each illustrated state in state diagram 200.

After an organization completes profile set up, the state machine may initialize to state 202. Suggestions and participant messages may be structured around safe workforce behavior/practices and employee/contractor behavior outside of the work place. In state 202z, the organization's locations may be operating in a low risk virus environment, e.g., based on the reporting district' geolocation-pathogen-risk scores or those for the facilities. An administrator's computing device may receive 1 to 2 workforce safety messages daily. Further, the organization may develop its own workforce safety procedures, scenario appropriate ones of which may be accessed via the user interface described below with reference to FIG. 7. There may be thousands or more messages available in the system as candidates to select among.

Transition to state 204 may occur if the level of risk in a reporting district where a facility operates rises during a pandemic or if the facility's score increases. An administrator and location leadership may be informed of this risk and the related messaging platform change. In a rising risk environment, some embodiments may activate different messaging content. This content may be designed to inform the administrator and location leadership (through messages to, and presented by, their computing devices) of the nature of the increased risk and provide suggestions for lowering company and workforce risk levels. If risk levels continue to rise in the facility, the messaging content may change to display the types of actions leadership should consider to reduce the risk of participant infection and death.

If the level of risk escalates to a critical stage, e.g., where shelter-in-place is mandatory, a transition to state 206 may activate other content. In this state, some embodiments deliver messaging to support the facility's leadership and participants and their compliance with federal, state, or local restrictions. The administrator and leadership may select messages that indicate that all movement are "essential only" and increase the likelihood that participants are aware of and compliant with government mandates and reduce the risk of pathogen exposure.

In a reducing risk environment, the system may transition to state 208 and active other content. This content may be designed to inform the administrator and leadership of the nature of the decreased risk and provide suggestions for continuing to lowering risk levels. If risk levels continue to fall, the messaging content will change to display the new types of actions the leadership or other participants may take to further reduce or maintain a safe and healthy organization.

Figure 7:
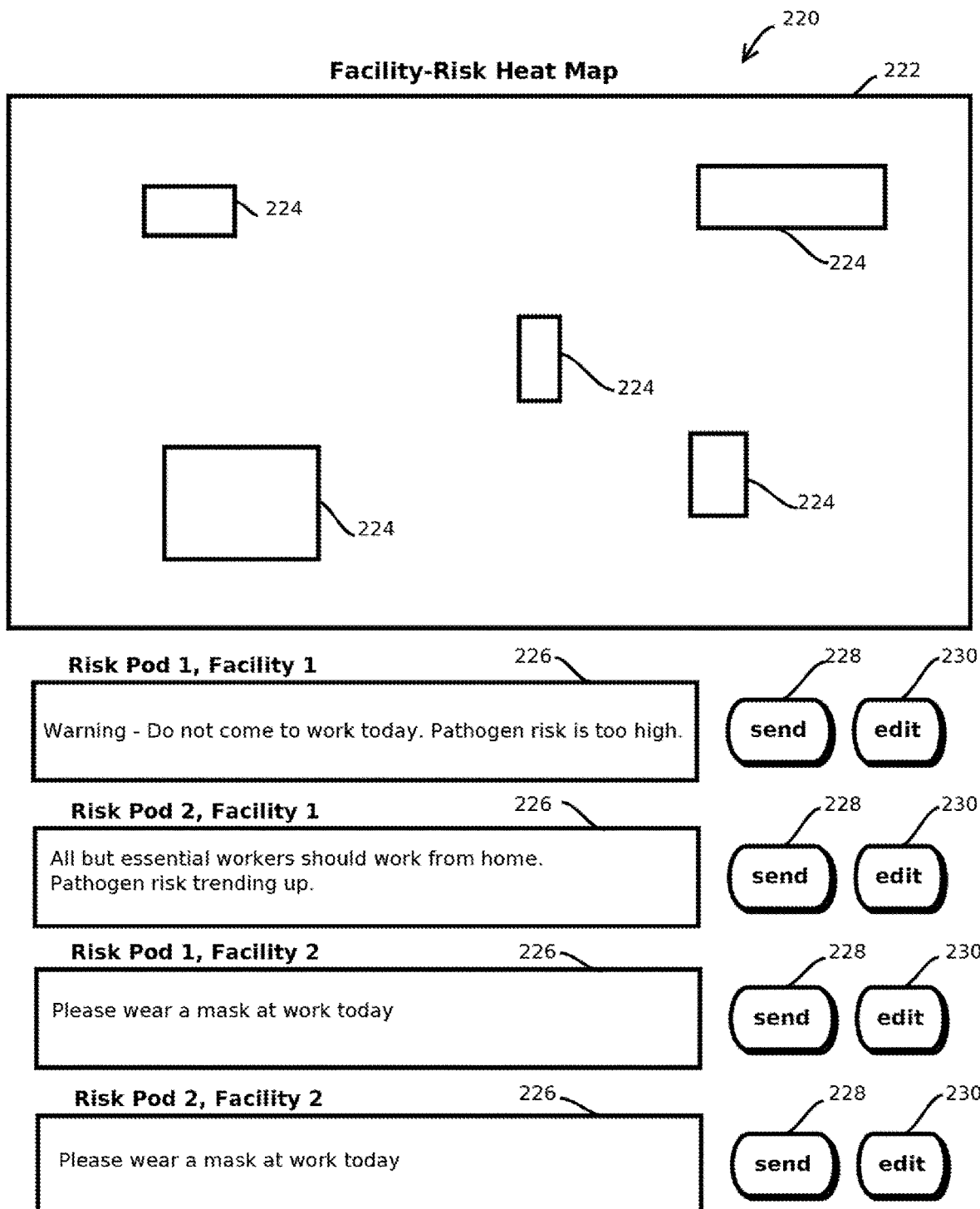
FIG. 7 illustrates an example of a user interface consistent with some embodiments of the present techniques.

In some embodiments, execution of the finite state machine 81 may cause the server system 12, for instance in cooperation with the controller 74, to cause computing devices of leadership of an organization to present a user interface like interface 220 shown in FIG. 7. In some embodiments, the user interface 220 like the other user interfaces described herein, may be presented in a web browser or in the native application 58, in some cases upon a corresponding user authenticating themselves as a member of leadership to the server system 12 through an identity management system. In some embodiments, the user interface 220 includes a facility-risk heat map 222 having a map extent shown within the illustrated rectangle and including various facilities 224 depicted therein. This map may support panning, zooming, and bounding-box-queries like those examples discussed above, which may also entail a map interface like that shown. In some embodiments, visual attributes of those facilities 224 may be modulated to indicate geolocation pathogen risk, for example color, line weight, animated movements, and the like. In some embodiments, each of the facilities illustrated 224 may correspond to a region of a display screen that when selected by the user, causing an event (like an on-touch event, a touch-release event, an on-click event, or the like) to be passed to an event handler that causes the user interface 222 update to display additional information about the respective facility, for example, upon querying server system 12 for such information. Examples include breakdowns by risk pod, trendlines for geolocation-pathogen-risk scores, aggregate statistics about vulnerability of visitors to the respective facility to pathogen at issue, and the like.

In some embodiments, the user interface 220 includes proposed natural language text 226 specific to each facility and each risk pod of each was facility. In some embodiments, the proposed text may be determined with process 180 described above. In some embodiments, there may be multiple options of proposed text. Similar UI elements may display messages to leadership that are not editable. In some embodiments, each unit of proposed text may be in a text input box that supports editing or rewriting. A rewrite or supply of new text from a user in leadership is considered an edit in this example. In some embodiments, the user interface 220 further includes inputs by which the message may be sent or with which the message may be placed into a state that supports editing, as indicated by buttons 228 and 230 respectively. Sending a message with selection of button 228 may trigger any of the various modes of conveying messages discussed above with reference to step 190 of block 180, among the other examples above.

Privacy-Safe Movement Transaction Processing to Assess Pandemic Risk

Some embodiments may implement a privacy preserving approach to gathering data about people's movements among geographic places, which in some cases may not reveal to server-side hardware (e.g., server system 12, which may include one or more servers) the identity of those people or, and some cases, which movements at different times are movements by the same person to impede attempts to deanonymize data based upon patterns of movements unique to individuals.

Some embodiments include obtaining movement transactions of a population of users, for instance in accordance with the techniques described above, by which native applications 58 executing on user's mobile computing devices 14 sense their geolocation and provide corresponding information to server system 12 that obtains the information. In some cases, the native application may be operative to generate movement transactions, each movement transaction including a starting geographic position (e.g., lat-long coordinates or place-of-interest, geographic region, or other geolocation identifier), an ending geographic position, and a datestamp, such as a timestamp with varying levels of granularity, like specific to the minute, hour, day, or week, or more or less granular, in some case for both starting and ending positions, or in some cases for just one or an average thereof.

In some embodiments, movement transactions may begin and end with the detection of dwells at geographic locations, for instance those geolocations including the geographic positions, like places of interest or geographic regions. In some embodiments, the native application 58, or the geolocation framework 60, may be configured to detect dwells and, in response, emit an event or call a previously-registered callback function that causes a new movement transaction to be created by the native application 58, for instance, indicating a movement from a previously detected well to a new dwell. In some embodiments, dwells may be detected responsive to a determination that the geolocation of the mobile computing device 14 has remained within a geographic area, like within a geo-fence, for more than a threshold amount of time, like more than five minutes, more than 10 minutes, or more than an hour.

In some embodiments, the movement transactions may be formatted or otherwise transformed from source data in a way that impedes attempts to deanonymize collections of movement transactions through statistical analysis for patterns unique to individuals. In some embodiments, movement transactions may not include personally identifiable information about users, global unique identifiers within a namespace of the server system 12 by which different users are distinguished with from one another, even if pseudonymously, or the like. In some embodiments, movement transactions are encoded in a less granular format than that with which data is sensed by the mobile computing device 14. For example, dwells detected at the level of an individual room or floor of a building may be encoded in the movement transaction as indicating the corresponding place of interest or geographic region, without identifying the individual room or floor of the building. In some embodiments, noise may be added to geolocation of starting or ending positions of dwells, for example, by randomly selecting a distance and an angle and offsetting the geolocation of starting and ending positions, or date stamps may be adjusted by adding or subtracting random offsets. In some embodiments, these random values may be selected from a normal distribution, such that aggregations of such values may produce population statistics of measures of central tendency that are unaffected by the noise, while individual movement transactions provide unreliable information about that individual movement.

In some embodiments, the movement transactions are reported to the server system 12 at the time a movement transaction concludes, or in some embodiments, native applications 58 may buffer such movement transactions, for example, for an hour, day, week, or longer or shorter duration, before a batch is sent to the server system 12. In some embodiments, the movement transactions may be conveyed to the server system 12 in a manner that either does not identify the mobile computing device or corresponding user undergoing those movements to the server system 12 or does not leave a persistent record at the server system 12 by which such information can be retrieved later. In some cases, the information may be conveyed over a network 26 in a protocol, like the Internet protocol, that includes a source network address of the sending computing device 14 in a header of an Internet protocol packet received by the system 12 when conveying movement transactions as a payload of that packet. In some embodiments, the server system 12 may immediately (e.g., within a day, minute, or 50 ms of receipt) delete the sender network address from such received packets. Similar techniques may be applied to session identifiers in some cases at other layers of a protocol stack, for example upon determining that a session has completed or more than a threshold amount of time has elapsed since a session began or was last active.

In some embodiments, movement transactions may be conveyed to the server system 12 from sending mobile computing devices 14 in a way that prevents the server system 12 from having access to the network address or other device identifier of mobile computing devices 14 by which mobile computing devices 14 (or users, or instances of native application 48) can be uniquely (or specified to some granularity, like less than 10% of users, less than 1% of users, or less than 0.0001% of users) distinguished from other mobile computing devices of a population of users. For example, some embodiments may relay movement transactions via the Tor network. In another example, a decentralized routing protocol may be implemented among peer relays implemented by the native application 58 and a population of users, for example, with one, two, three, four, five or more or fewer hops from a sending mobile computing device 14 through a sequence of relaying mobile computing devices 14 before a final relaying mobile computing device 14 advances the movement transactions from the sending mobile computing device 14 to the server system 12.

In some embodiments, the sending mobile computing device 14 may encrypt the movement transactions with a public cryptographic key of the server system 12 before sending to a first relaying mobile computing device 14. In some embodiments, such encryption may be implemented with an asymmetric cryptographic protocol, like RSA, El Gamal, lattice-based encryption, elliptic curve encryption, or the like. In some cases, relaying mobile computing devices 14 may not have access to a plain text version of the ciphertext containing movement transactions that they relay to the server system 12, which may decrypt the ciphertext with a private cryptographic key held by the server system 12 in memory and not provided to the mobile computing devices 14.

In some embodiments, mobile computing devices may select and obtain network addresses of downstream relaying mobile computing devices to relay movement transactions with a variety of techniques. In some embodiments, the mobile computing devices may make the selection in a way that does not reveal to the server system 12 which mobile computing device was selected or that the selecting mobile computing device had access to a network address of the selected mobile computing devices in some cases. In some embodiments, a distributed hash table may be used for addressing among the instances of the native application 58 executed by a population of mobile computing devices 14. Examples include distributed hash table implementations in Chord and Kademlia. In some embodiments, network addresses, like IP address or identifier suitable to communicate via Firebase Messaging Service™ or the equivalent service in the Apple ecosystem may be accessed by the mobile computing devices 14 for selected relaying mobile computing devices with such a data structure, without the centralized server system 12 having access to information by which it can be determined which peer addresses were accessed by an individual mobile computing device 14.

In some embodiments, the server system 12 may send a set of 10, 20, 100, 1000, or more or fewer such network addresses to each mobile computing device, for example, randomly selected subsets of a population of mobile computing devices 14 having the native application 58 installed thereon. In some embodiments, the native applications 58 may store these subsets of addresses in memory, and randomly select among these subsets to determine downstream relay nodes in a multi-hop path to the server system 12. In some embodiments, each hop may include a hop count appended to the package conveying the movement transactions, with each relay incrementing the count, and a final relaying computing device may route the information to the server system 12 when it determines the hop count exceeds a threshold value, like two, three, four or more. In some embodiments, this process is expected to make it difficult or impossible to deanonymize the network address of the sending mobile computing device based upon patterns of movement transactions and the final relaying move mobile computing devices network address included in a header of an Internet protocol packet received by the server system 12.

Some embodiments include obtaining the geolocation pathogen risk scores of the starting geolocations in the movement transactions received at the server system 12, for instance by querying records in the geographic information system 84, in some cases expediting such queries with the techniques described above with reference to FIG. 3.

In some embodiments, a relatively large number of such movement transactions may be processed, like more than 100 million per day or hour, more than 1 billion per day or hour, or more than 10 billion per day or hour, and some embodiments may expedite operations by performing analyses concurrently, for instance using the above-described techniques implemented on compute clusters.

In some embodiments, the movement transactions for a batch (e.g., corresponding to an hour or day) may be grouped according to ending geolocation including the ending geographic position of the movement transactions, and different groups may be assigned to different computing devices in such a compute cluster to concurrently compute geographic-pathogen-risk scores of those respective geolocations, for instance in accordance with the techniques described above with reference to FIG. 4. To this end, some embodiments include updating geographic-pathogen-risk scores of the ending geolocations based upon geographic-pathogen-risk scores of the starting geolocations involve the movement transactions ending at the ending geolocations.

In some embodiments, the updated scores are also based upon rates of traffic of people at the ending geolocations indicated by the movement transactions. Rates of traffic may be quantified with a variety of metrics including measurements of a number of people inferred to be at a geolocation at a given point of time or windowing time, measurements of a number of people inferred to be arriving at or leaving from a geolocation of a given point in time or window of time, or a combination thereof, for example a density-weighted arrival or departure rate metric based on the product of the number of people inferred to be at a geolocation and the number of people arriving at or leaving the geolocation at a point in time or window of time. The latter metric may capture a measure of how much a given person at the geolocation interacts with other people at the geolocation, as a crowded emergency waiting room with a long wait time and a lot of people arriving and leaving may exhibit different risk than a turnstile with a lot of people passing therethrough but relatively little dwell time at the turnstile. In some embodiments, individuals' arrival at and then departure from a geolocation may not be correlatable by the server system 12 in virtue of the way the movement transactions are anonymized in some embodiments, for instance without a persistent global unique identifier of users of the native application 58 being associated with each movement transaction by which arrivals and departures may be matched.

In some embodiments, rates of traffic at ending geolocations may be determined by obtaining a set of movement transactions ending at or leaving from the respective geolocation over a window of time and then sorting those movement transactions according to those times. Some embodiments may then initialize a counter, for example, at zero or based upon a previously determined count and, then, iterate through the list in order, incrementing the counter with each arrival indicated by an ending geographic position at the respective geolocation at issue, and decrementing the counter with each departure indicated by a starting geographic position at the respective geolocation at issue. In some embodiments, the counter may indicate an estimate of the number of people at the geolocation at the point in time corresponding to date stamps of movement transactions in the ordered list. In some embodiments, date stamps may be applied to both the start and the end of movement transactions by the native application 58 to support such operations, or some embodiments may assume a default dwell time and only use arrival datestamps.

In some cases, these date stamps, as noted above, may be encoded in a sufficiently course format that it is difficult to reliably correlate the arrival of a person at a geolocation with the movement transaction to which they correspond, to back out where they started from. In some embodiments, the granularity with which date stamps are reported for starting or ending geolocations may be modulated based upon the rates of traffic at those geolocations, for instance. with higher rates of traffic causing the mobile computing devices 14 to use more granular date stamped reporting and vice versa, such that geographic places with relatively little foot traffic may have relatively course date stamps applied to movement transactions ending at or starting at those geolocations, as compared to places with high foot traffic.

In some embodiments, these updated geolocation pathogen risk scores may be stored and used in the manner described above with reference to FIGS. 1 through 7.

Enriching Geographic Information Systems with Pathogen-Risk Enhancing or Suppressing Attributes of Places of Interest As noted above, in some cases, account holders, like various users, associated with places of interest (e.g., so authorized or merely having visited as explained below) may use computing devices 20 (as shown in FIG. 1) to update records in the geographic information system 84 with additional attributes of places of interest relevant to propensity of pathogens to be transmitted at the respective geolocations. Examples of such attributes include any permutation of the following or similar attributes: an attribute indicative of an air filtration system of the building; an attribute indicative of a cleaning protocol of the building; an attribute indicative of an ultraviolet light of the building; an attribute indicative circulation of outside air into the building; an attribute indicative of touchless automatic doors of the building; an attribute indicative of humidity of air in the building; an attribute indicative of temperature of air in the building; an attribute indicative of sunlight in the building; an attribute indicative of persistence of a pathogen on surfaces in the building; or an attribute indicative of sneeze guards in the building. In some embodiments, this information may be supplied via a web portal or via the native application 58 described above.

In some embodiments, upon receiving one or more of these attributes, the server system 12 may update geolocation pathogen risk scores based on the new information, for example, reducing the amount of risk indicated by such scores based upon attributes indicating risk-mitigating measures taken at the places of interest like those discussed above. In some embodiments, this may be a percentage reduction indicated by a coefficient corresponding to each attribute multiplied by the original score, some embodiments may subtract an offset corresponding to the attribute, or in some cases, the attributes (or cumulative effects thereof) may be input features to the above-described machine learning models for computing such scores. In some embodiments, the updating may be performed with the process 140 discussed above with reference to FIG. 4. As is the case with the other examples of updating herein, updating can include changing an existing value or creating a new copy or version of the value with the change present.

In some embodiments, a plurality of such attributes of a geolocation may be received, and some embodiments may determine a cumulative effect of those attributes to apply when updating geolocation pathogen risk scores. In some cases, the attributes may combine in nonlinear ways, for example synergistically, or in some cases counteracting one another. In some cases, these interaction effects may become quite complicated as additional attributes are added, for example, increasing with the possible permutations of the number of attributes, which may increase factorial a as additional attributes are tracked. In some cases, the number of attributes may be greater than 10, 50, 100, or 500.

In some cases, interactions between attributes may be inferred with a machine learning model trained upon historical data stored by the server system 12. In some cases, this may be the same model as is used to compute the above-noted geolocation-pathogen-risk scores in process 140, or it may be a different model, e.g., one downstream of that model in process 140, in a pipeline or some other ensemble.

In some embodiments, as a training set, the server system 12 may store previous changes in geolocation pathogen risk scores, previous incidents of infection, missed work, or death at geolocations, along with attributes of those geolocations. Some embodiments may predict a default number or rate of such adverse events given then existing geolocation pathogen risk scores, for example, with scores that do not account for attributes. Some embodiments may then determine an amount by which the geolocations over or under-performed these estimates and attribute those differences to the attributes, in some cases, or in some cases including additional features. Some embodiments may train a model to predict these differences given attributes based on such historical data. Examples of suitable machine learning models include deep (3, 5, 10, or 50 or more layer) neural networks, regression trees or random forest thereof, linear regressions, and the like. In some cases, these models may be trained or otherwise configured with the techniques described above.

Additionally or alternatively, some embodiments may determine initial or final inferred cumulative effects from an interaction matrix, which may be an n-by-n matrix or n-dimensional matrix, where n is the number of attributes at issue. In some embodiments, values in this matrix may indicate the cumulative effect of attributes that indexed to that location.

In some cases, some attributes may be nominal values or binary values, and some attributes may be cardinal or ordinal values. In some cases, each value or range of values in cardinal or ordinal values may correspond to a different attribute, e.g., "low, medium, or high outside airflow" or "0 to 1 watt of UV light per square meter" vs "1 to 3 watts of UV light per square meter." Or some embodiments may learn a function or have hardcoded within the model a function that indicates cumulative effects. In some embodiments, different models or interaction matrices may be maintained for different pathogens and different variants thereof, as such interactions may vary by pathogen, for instance some may be subject to fomite transmission, while others are purely aerosol, and different attributes may affect these modalities differently.

In some embodiments, attributes may only be accepted from authenticated users determined to be authorized to provide such information by server system 12. Examples include those who have previously registered as the entity owning or otherwise controlling a geolocation, like a building, for instance in an organizations account by which facilities are tracked in the manner discussed above with reference to FIGS. 6 and 7. In some embodiments, the general public may be invited to supply attributes, which may produce less reliable reporting. Some embodiments may receive a plurality of different characterizations of an attribute of a building, for instance, some indicating the presence of ultraviolet lights and others indicating the absence of ultraviolet lights. Some embodiments may reconcile these reports by, for example, determining a majority characterization and selecting the majority characterization as the attribute. Some embodiments may maintain a reputation system by which users are scored according to the historical accuracy of their reports, and some embodiments may determine a user-accuracy score that is used to weight user characterizations in such majority votes, selecting an accuracy-weighted majority as the characterization of the attribute to be used.

In some embodiments, upon updating the geographic-pathogen-risk score of a given geolocation, this change may be used to update other geographic-pathogen-risk scores of other geolocations, for example, those subject to a co-visitation, as indicated by the above-described movement transactions. For example, some embodiments may determine one, two, three, or more degree separations in a movement graph indicated by movement transactions from the given geolocation subject to the update, and some embodiments may update other geolocations geographic-pathogen-risk scores based upon the attribute that was reported or the resulting change in the given geolocations geographic risk score. For example, a report of an attribute that tends to reduce risk at a given geolocation may cause the risk score of adjacent geolocations in a movement graph to be lowered to indicate the reduced risk of someone contracting a virus while at the given geolocation and then spreading to others at subsequently visited geolocations.

In some embodiments, these updated geolocation pathogen risk scores may be stored and used in the manner described above with reference to FIGS. 1 through 7.

In some embodiments, the present filing may apply the techniques claimed in the following non-provisional patent applications filed on the same day as the first non-provisional priority date of this patent filing (and sharing a disclosure with that filing), bearing the following titles and application serial numbers, with the same inventor and assignee as that first non-provisional filing, the contents of each of which are hereby incorporated by reference: U.S.

patent application Ser. No. 17/381,954 titled PERSONAL AND CORPORATE PATHOGEN-RISK ASSESSMENT WITH PANDEMIC-BIO-SURVEILLANCE MULTI PATHOGEN SYSTEMS; U.S. patent application Ser. No. 17/381,956, subsequently issued as U.S. Pat. No. 11,586,825, titled GEOLOCATION PATHOGEN-RISK ASSESSMENT WITH PANDEMIC-BIO-SURVEILLANCE MULTI PATHOGEN SYSTEMS; U.S. patent application Ser. No. 17/382,067 titled BEHAVIOR MODIFICATION MESSAGING WITH PANDEMIC-BIO-SURVEILLANCE MULTI PATHOGEN SYSTEMS; U.S. patent application Ser. No. 17/381,932 titled NATURAL-LANGUAGE TEXT GENERATION WITH PANDEMIC-BIO-SURVEILLANCE MULTI PATHOGEN SYSTEMS; and U.S. patent application Ser. No. 17/381,937 titled ENRICHING GEOGRAPHIC-INFORMATION SYSTEMS WITH GEOLOCATION ATTRIBUTES TO ENHANCE ACCURACY OF PANDEMIC-BIO-SURVEILLANCE MULTI PATHOGEN SYSTEMS.

Figure 8:
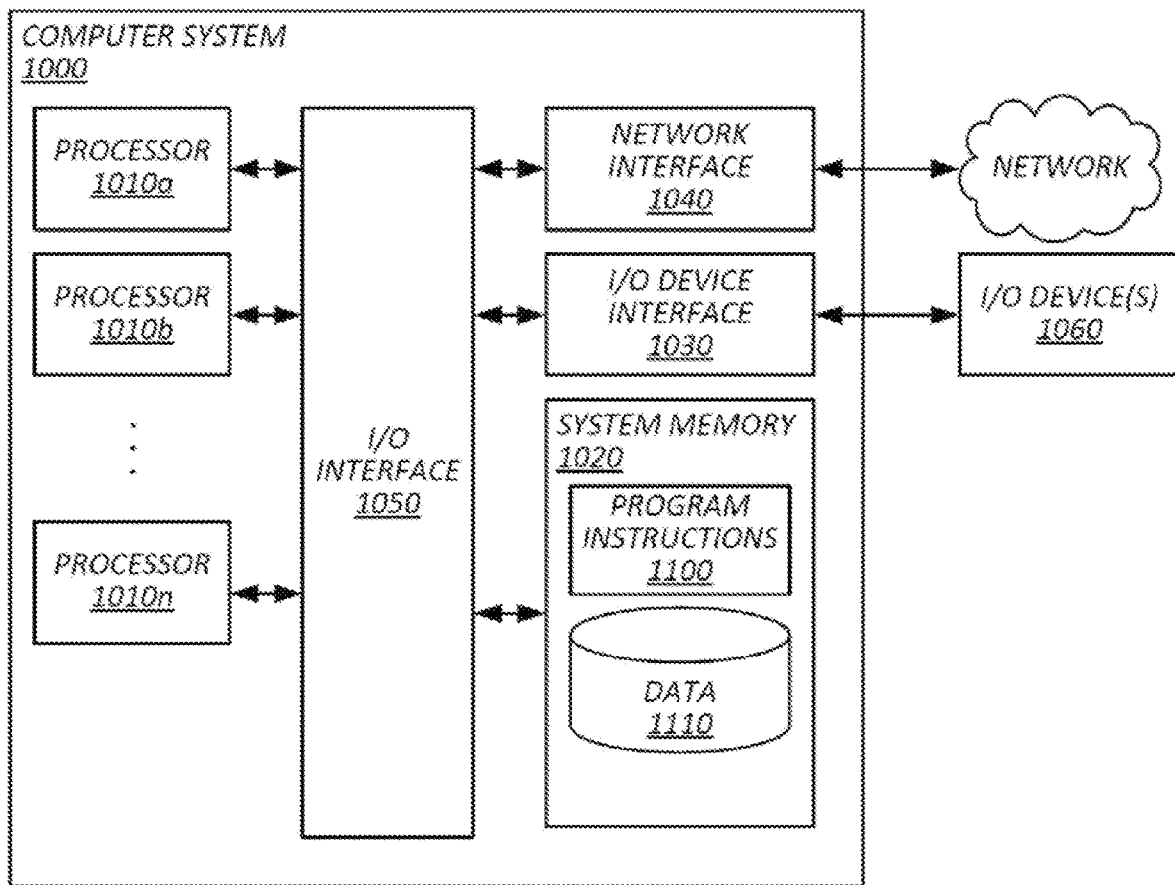
FIG. 8 illustrates an example of a computing device by which the present techniques may be implemented.

FIG. 8 is a diagram that illustrates an exemplary computing system 1000 in accordance with embodiments of the present technique. Various portions of systems and methods described herein, may include or be executed on one or more computer systems similar to computing system 1000. Further, processes and modules described herein may be executed by one or more processing systems similar to that of computing system 1000.

Computing system 1000 may include one or more processors (e.g., processors 1010a-1010n) coupled to system memory 1020, an input/output I/O device interface 1030, and a network interface 1040 via an input/output (I/O) interface 1050. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computing system 1000. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 1020). Computing system 1000 may be a uni-processor system including one processor (e.g., processor 1010a), or a multi-processor system including any number of suitable processors (e.g., 1010a-1010n). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computing system 1000 may include a plurality of computing devices (e.g., distributed computer systems) to implement various processing functions.

I/O device interface 1030 may provide an interface for connection of one or more I/O devices 1060 to computer system 1000. I/O devices may include devices that receive input (e.g., from a user) or output information (e.g., to a user). I/O devices 1060 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 1060 may be connected to computer system 1000 through a wired or wireless connection. I/O devices 1060 may be connected to computer system 1000 from a remote location. I/O devices 1060 located on remote computer system, for example, may be connected to computer system 1000 via a network and network interface 1040.

Network interface 1040 may include a network adapter that provides for connection of computer system 1000 to a network. Network interface May 1040 may facilitate data exchange between computer system 1000 and other devices connected to the network. Network interface 1040 may support wired or wireless communication. The network may include an electronic communication network, such as the Internet, a local area network (LAN), a wide area network (WAN), a cellular communications network, or the like.

System memory 1020 may be configured to store program instructions 1100 or data 1110. Program instructions 1100 may be executable by a processor (e.g., one or more of processors 1010a-1010n) to implement one or more embodiments of the present techniques. Instructions 1100 may include modules of computer program instructions for implementing one or more techniques described herein with regard to various processing modules. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 1020 may include a tangible program carrier having program instructions stored thereon. A tangible program carrier may include a non-transitory computer readable storage medium. A non-transitory computer readable storage medium may include a machine readable storage device, a machine readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory 1020 may include a non-transitory computer readable storage medium that may have program instructions stored thereon that are executable by a computer processor (e.g., one or more of processors 1010a-1010n) to cause the subject matter and the functional operations described herein. A memory (e.g., system memory 1020) may include a single memory device and/or a plurality of memory devices (e.g., distributed memory devices). Instructions or other program code to provide the functionality described herein may be stored on a tangible, non-transitory computer readable media. In some cases, the entire set of instructions may be stored concurrently on the media, or in some cases, different parts of the instructions may be stored on the same media at different times.

I/O interface 1050 may be configured to coordinate I/O traffic between processors 1010a-1010n, system memory 1020, network interface 1040, I/O devices 1060, and/or other peripheral devices. I/O interface 1050 may perform protocol, timing, or other data transformations to convert data signals from one component (e.g., system memory 1020) into a format suitable for use by another component (e.g., processors 1010a-1010n). I/O interface 1050 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computer system 1000 or multiple computer systems 1000 configured to host different portions or instances of embodiments. Multiple computer systems 1000 may provide for parallel or sequential processing/execution of one or more portions of the techniques described herein.

Those skilled in the art will appreciate that computer system 1000 is merely illustrative and is not intended to limit the scope of the techniques described herein. Computer system 1000 may include any combination of devices or software that may perform or otherwise provide for the performance of the techniques described herein. For example, computer system 1000 may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, or a Global Positioning System (GPS), or the like. Computer system 1000 may also be connected to other devices that are not illustrated, or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 1000 may be transmitted to computer system 1000 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present techniques may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may provided by sending instructions to retrieve that information from a content delivery network.

The reader should appreciate that the present application describes several independently useful techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Similarly, reference to "a computer system" performing step A and "the computer system" performing step B can include the same computing device within the computer system performing both steps or different computing devices within the computer system performing steps A and B. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device. Features described with reference to geometric constructs, like "parallel," "perpendicular/orthogonal," "square", "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first", "second", "third," "given" and so on, if used in the claims, are used to distinguish or otherwise identify, and not to show a sequential or numerical limitation. As is the case in ordinary usage in the field, data structures and formats described with reference to uses salient to a human need not be presented in a human-intelligible format to constitute the described data structure or format, e.g., text need not be rendered or even encoded in Unicode or ASCII to constitute text; images, maps, and data-visualizations need not be displayed or decoded to constitute images, maps, and data-visualizations, respectively; speech, music, and other audio need not be emitted through a speaker or decoded to constitute speech, music, or other audio, respectively. Computer implemented instructions, commands, and the like are not limited to executable code and can be implemented in the form of data that causes functionality to be invoked, e.g., in the form of arguments of a function or API call. To the extent bespoke noun phrases (and other coined terms) are used in the claims and lack a self-evident construction, the definition of such phrases may be recited in the claim itself, in which case, the use of such bespoke noun phrases should not be taken as invitation to impart additional limitations by looking to the specification or extrinsic evidence.

In this patent, to the extent any U.S. patents, U.S. patent applications, or other materials (e.g., articles) have been incorporated by reference, the text of such materials is only incorporated by reference to the extent that no conflict exists between such material and the statements and drawings set forth herein. In the event of such conflict, the text of the present document governs, and terms in this document should not be given a narrower reading in virtue of the way in which those terms are used in other materials incorporated by reference.

The present techniques will be better understood with reference to the following enumerated embodiments:

1. A tangible, non-transitory, machine-readable medium storing instructions that, when executed by one or more processors, effectuate operations comprising: obtaining, with a computer system, movement transactions of a population of users, wherein: the movement transactions each include a respective starting geographic position, a respective ending geographic position, and a respective datestamp, and the movement transactions are obtained without having server-side access to information by which the members of the population undergoing the changes in geolocation indicated by the movement transactions can be identified, either personally or pseudonymously; obtaining, with the computer system, for movement transactions corresponding to a designated window of time, geographic-pathogen-risk scores of starting geolocations that include the starting geographic positions; updating, with the computer system, for the movement transactions corresponding to the designated window of time, geographic-pathogen-risk scores of the ending geolocations based on both geographic-pathogen-risk scores of the starting geolocations involved in movement transactions ending at the ending geolocations and rates of traffic at the ending geolocations indicated by movement transactions ending or starting at the ending geolocations; and storing, with the computer system, the updated geographic-pathogen-risk scores of the ending geolocations in memory.

2. The medium of embodiment 1, wherein the movement transactions are obtained without having server-side access to information by which movement transaction can be determined to be movement transaction by the same person, including without having server-side access to unique device, client-application instance, or user identifiers by which devices or members of the population of users are uniquely distinguishable from one another.

3. The medium of any one of embodiments 1-2, wherein the movement transactions are reported by native applications executing on mobile computing devices of the population of users to a server system.

4. The medium of embodiment 3, wherein the movement transactions are conveyed from the mobile computing devices of the population of users to the server system via an encrypted message routed via one or more of the other the mobile computing devices of the population of users, the one or more of the other the mobile computing devices of the population of users not advancing a source address of an Internet Protocol packet initiating the encrypted message to the server system, such that the server system does not have information to associate movement transactions with network addresses of sending mobile computing devices of the population of users.

5. The medium of embodiment 4, wherein: the movement transactions are encrypted, with a public key of the server system, by sending mobile computing devices of the population of users, and relaying mobile computing devices of the population of users do not have access to plain text versions of the movement transactions.

6. The medium of embodiment 5, wherein: network addresses of the relaying mobile computing devices of the population of users are determined by sending mobile computing devices of the population of users with a distributed hash table, without the sending mobile computing devices querying the server system for the network addresses of the relaying mobile computing devices or otherwise revealing all of a corresponding multi-hop network path to the server system.

7. The medium of any one of embodiments 1-6, wherein the operations comprise: sending, from a server system of the computer system, to mobile computing devices of the population of users, respective relay address sets, each set including 20 or more addresses of other mobile computing devices of the population of users; relaying over two or more hops the movement transactions reported by a sending mobile computing device by, at each hop, randomly selecting among the 20 or more addresses sent to the respective mobile computing device by the server system, before relaying the movement transactions reported by a sending mobile computing device to a next hop before a final relaying mobile computing device sends the movement transactions reported by a sending mobile computing device to the server system, without conveying a network address of the sending mobile computing device to the server system.

8. The medium of any one of embodiments 1-6, wherein the operations comprise conveying movement transactions without revealing a network address of a sender to a final recipient.

9. The medium of any one of embodiments 1-8, wherein the operations comprise: obtaining movement transactions comprises obtaining set of over 100 million movement transactions corresponding to more than a 1 hour duration of time over which corresponding movements occurred; segmenting the set into subsets, wherein the subsets are grouped by geolocations corresponding to the ending geographic positions of the movement transactions in the set; and distributing the subsets among computing devices of a compute cluster storing the subsets in resilient distributed datasets, as immutable collections of objects, wherein different computing devices of the compute cluster concurrently update different geographic-pathogen-risk scores of the ending geolocations.

10. The medium of any one of embodiments 1-8, wherein the operations comprise: obtaining movement transactions comprises obtaining set of over 100 million movement transactions corresponding to more than a 1 hour duration of time over which corresponding movements occurred; segmenting the set into subsets, wherein the subsets are grouped by geolocations corresponding to the ending geographic positions of the movement transactions in the set; and sending different subsets to different computing devices of a compute cluster, wherein updating geographic-pathogen-risk scores of the ending geolocations is performed for different ending geolocations concurrently with MapReduce.

11. The medium of any one of embodiments 1-10, wherein: the ending geographic positions of the movement transactions are within a plurality of geolocations, including geolocations that are geographic regions and geolocations that are places of interest within those geographic regions; the operations further comprise: obtaining, with the computer system, first data about at least some of the plurality of geolocations, wherein: the first data is updated less frequently than a first rate, and the first data is not pathogen specific; obtaining, with the computer system, second data about at least some of the plurality of geolocations, wherein: the second data is updated more frequently than a second rate that is more frequent than the first rate, and the second data is pathogen-specific; determining, with the computer system, geolocation-pathogen-risk scores of the geographic regions based on both the first data and the second data; determining, with the computer system, geolocation-pathogen-risk scores of the places of interest with a machine learning model trained to allocate risk of geographic regions to places of interest within those geographic regions based on at least some of the first data, such that at least some places of interest in the same geographic region have different geolocation-pathogen-risk scores; and storing, with the computer system, the geolocation-pathogen-risk scores of the places of interest and the geolocation-pathogen-risk scores of the geographic regions in memory; the first data is static data; the second data is dynamic data; at least some of the geographic regions are reporting districts; at least some of the places of interest are smaller than 1,000 square meters; the geolocation-pathogen-risk scores of the places of interest and the geolocation-pathogen-risk scores of the geographic regions are specific to the corresponding geolocations and are independent of potential visitors to those corresponding geolocations; the static data includes census data updated once per decade; and the dynamic data includes amounts of infections, vaccinations, or deaths attributable to a given pathogen in the geographic regions updated at least daily.

12. The medium of any one of embodiments 1-11, wherein: the datestamps of the movement transactions indicate time of day in which the movement transaction began; the operations further comprise determining the rates of traffic at the ending geolocations indicated by the movement transactions with operations comprising: sorting, by datestamp, a set of movement transactions having ending geographic positions or starting geographic positions within a given place of interest to form a sorted list of movement transactions; iterating through the sorted list and incrementing a counter upon encountering during an iteration a movement transaction in the sorted list with an ending geographic position at the given place of interest and decrementing the counter upon encountering during an iteration a movement transaction in the sorted list with a starting geographic position at the given place of interest; and estimating a number of people at the given place of interest at a given time based on a value of the counter while incrementing through a first range of the sorted list of movement transactions corresponding to the given time.

13. The medium of any one of embodiments 1-12, wherein the operations further comprise: estimating a measure of central tendency of a number of people at the given place of interest based on values of the counter while incrementing through a second range of the sorted list of movement transactions that is larger than the first range.

14. The medium of any one of embodiments 1-13, wherein updating geographic-pathogen-risk scores of the ending geolocations comprises updating, for each of the ending geolocations, a plurality of geographic-pathogen-risk scores corresponding to a plurality of different pathogens.

15. The medium of any one of embodiments 1-14, wherein updating geographic-pathogen-risk scores of the ending geolocations comprises updating, for each of the ending geolocations, a plurality of geographic-pathogen-risk scores corresponding to a plurality of different variants of a given pathogen.

16, The medium of any one of embodiments 1-15, wherein the operations further comprise determining amounts of people visiting a given places of interest corresponding to ending geographic positions among the movement transactions with operations comprising: obtaining a latitude and longitude coordinate of an ending location of a given movement transaction among the anonymized movement transactions; truncating digits of the latitude and longitude coordinates less significant than a threshold position to form truncated coordinates; determining an identifier of a grid square from the truncated coordinates; using the identifier of the grid square as a pointer to a set of geolocations in the grid square; and computing, for at least some of the set of geolocations in the grid square, point-in-polygon algorithm results based on the latitude and longitude coordinate, using more significant digits than are present in the truncated coordinates, without computing point-in-polygon algorithm results based on the latitude and longitude coordinate for geolocations in other grid squares.

17. The medium of embodiment 16, wherein: the place of interest is a geolocation queried from a geographic information system that stores more than 100,000 geolocations, each designated with a corresponding polygon having latitude and longitude coordinates as vertices; and less than 0.01% of the geolocations are analyzed with the point-in-polygon algorithm to determine whether the given movement transaction indicates a visit, thereby reducing worst-case run-time computational complexity by more than three orders of magnitude relative to systems that analyze every one of the 100,000 geolocations to determine which are visited.

18. A method comprising: the operations of any one of embodiments 1-17.

19. A system, comprising: one or more processors; and memory storing instructions that when executed by the processors cause the processors to effectuate operations comprising: the operations of any one of embodiments 1-17.

What is claimed is:

1. A tangible, non-transitory, machine-readable medium storing instructions that, when executed by one or more processors, effectuate operations comprising:
obtaining, with a computer system, a plurality of geolocations from a geographic information system, the plurality of geolocations including both geolocations that are geographic regions and geolocations that are places of interest within those geographic regions;
obtaining, with the computer system, first data about at least some of the plurality of geolocations, wherein:
the first data is updated less frequently than a first rate, and
the first data is not pathogen specific;
obtaining, with the computer system, second data about at least some of the plurality of geolocations, wherein:
the second data is updated more frequently than a second rate that is more frequent than the first rate, and
the second data is pathogen-specific;
determining, with the computer system, geolocation-pathogen-risk scores of the geographic regions based on both the first data and the second data;
determining, with the computer system, geolocation-pathogen-risk scores of the places of interest by allocating risk of geographic regions to places of interest within those geographic regions based on at least some of the first data, such that at least some places of interest in the same geographic region have different geolocation-pathogen-risk scores; and storing, with the computer system, the geolocation-pathogen-risk scores of the places of interest and the geolocation-pathogen-risk scores of the geographic regions in memory.

2. The medium of claim 1, wherein:
allocating risk is performed with a machine learning model trained to allocate risk of geographic regions to places of interest within those geographic regions based on at least some of the first data;
the first data is static data;
the second data is dynamic data;
at least some of the geographic regions are reporting districts;
at least some of the places of interest are smaller than 1,000 square meters; and
the geolocation-pathogen-risk scores of the places of interest and the geolocation-pathogen-risk scores of the geographic regions are specific to the corresponding geolocations and are independent of potential visitors to those corresponding geolocations.

3. The medium of claim 2, wherein:
the static data includes census data updated once per decade; and
the dynamic data includes amounts of infections, vaccinations, or deaths attributable to a given pathogen in the geographic regions updated at least daily.

4. The medium of claim 1, wherein:
the second data includes anonymized movement transactions each both corresponding to a movement of a person between geolocations and including starting and ending geographic coordinates; and
determining geolocation-pathogen-risk scores of the places of interest comprises determining amounts of people visiting the places of interest during designated windows of time based on the movement transactions.

5. The medium of claim 4, wherein the movement transactions are obtained without having server-side access to personally identifiable information of the people undergoing the corresponding movements and based on geolocations sensed by mobile computing devices carried by the people undergoing the corresponding movements, and wherein at least some of the geolocations are individual floors of a multi-story building, each of at least of a plurality of the floors corresponding to a different geolocation for which a respective geolocation-pathogen-risk score is determined.

6. The medium of claim 5, wherein movement transactions are obtained without having server-side access to pseudonymous identifiers of the people undergoing the corresponding movements by which movement transactions by the same person are correlatable.

7. The medium of claim 4, wherein determining amounts of people visiting the places of interest comprises:
steps for reducing latency when querying the geographic information system.

8. The medium of claim 4, wherein determining amounts of people visiting the places of interest comprises:
obtaining a latitude and longitude coordinate of an ending location of a given movement transaction among the anonymized movement transactions;
truncating digits of the latitude and longitude coordinates less significant than a threshold position to form truncated coordinates;
determining an identifier of a grid square from the truncated coordinates;
using the identifier of the grid square as a pointer to a set of geolocations in the grid square; and
computing, for at least some of the set of geolocations in the grid square, point-in-polygon algorithm results based on the latitude and longitude coordinate, using more significant digits than are present in the truncated coordinates, without computing point-in-polygon algorithm results based on the latitude and longitude coordinate for geolocations in other grid squares.

9. The medium of claim 8, wherein:
the geographic information system stores more than 100,000 geolocations, each designated with a corresponding polygon having latitude and longitude coordinates as vertices; and
less than 0.01% of the geolocations are analyzed with the point-in-polygon algorithm to determine whether the given movement transaction indicates a visit, thereby reducing worst-case run-time computational complexity by more than three orders of magnitude relative to systems that analyze every one of the 100,000 geolocations to determine which are visited.

10. The medium of claim 1, the operations further comprising:
obtaining a geolocation to be visited by a person;
obtaining a record indicative of that person's compliance with previous behavior modification messaging regarding pathogen risk;
determining a risk modifier score based on the record; and
modifying at a geolocation-pathogen-risk score corresponding to the geolocation to be visited by the person with the risk modifier score to form a personalized geolocation-pathogen-risk score, wherein failures to respond to comply with previous behavior modification messaging regarding pathogen risk causes the personalized geolocation-pathogen-risk score to indicate more risk.

11. The medium of claim 10, the operations further comprising:
determining that the personalized geolocation-pathogen-risk satisfies a threshold; and
in response, causing a message to be presented to the person via the person's mobile computing device.

12. The medium of claim 10, wherein the record and the personalized geolocation-pathogen-risk score are updated more frequently than the geolocation-pathogen-risk score for more than 1,000,000 people.

13. The medium of claim 1, wherein the operations comprise:
performing active learning with a machine learning model as new instances of the second data are obtained over time, wherein the second data is time-series data, wherein the machine learning model is trained to allocate risk of geographic regions to places of interest within those geographic regions based on at least some of the first data.

14. The medium of claim 1, the operations comprising:
obtaining a set of facilities of an organization, each of the facilities being at different geolocations;
obtaining a set of people who visit or are predicted to visit the facilities;
obtaining, for each of at least some members of the set of people, associated geolocations, at least some of the associated geolocations being geolocations including residences of respective members of the set or people or places the respective members of the set of people have previously visited;

accessing, from each member of the set of people who visit or are predicted to visit the facilities, the geolocation-pathogen-risk scores of the associated geolocations; and determining geolocation-pathogen-risk scores, or modified geolocation-pathogen-risk scores, of the facilities based on the geolocation-pathogen-risk scores of the associated geolocations.

15. The medium of claim 14, the operations further comprising:

determining subsets of the set of people based on the geolocation-pathogen-risk scores of their associated geolocations.

16. The medium of claim 15, the operations further comprising:

causing a message to be sent to computing devices of one of the subsets having the most severe geolocation-pathogen-risk score among the subsets, the message instructing the members of the one of the subsets to not visit the facilities; and causing a user interface to be presented showing color-coded representations of the facilities with colors indicating the geolocation-pathogen-risk scores of the facilities.

17. The medium of claim 14, wherein obtaining the set of people and obtaining the associated geolocations comprises querying a payroll or identity management service of the organization to obtain residential addresses of employees of the organization.

18. The medium of claim 1, the operations further comprising:

exposing an application program interface by which third party computing services interrogate the geolocation-pathogen-risk scores of at least some of the places of interest to inform product or service recommendations involving activities at the least some of the places of interest.

19. The medium of claim 1, the operations comprising:
steps for calculating geolocation-pathogen-risk scores for a plurality of variants of a plurality of pathogens; and
steps for personal-pathogen-risk-scoring.

20. The medium of claim 1, the operations comprising:
accessing historical geolocation-pathogen-risk scores of the geographic regions in memory;
training a machine learning model to predict geolocation-pathogen-risk scores based on the historical geolocation-pathogen-risk scores; and
determining, based on the trained machine learning model, features of the first data that correlate with changes in the historical geolocation-pathogen-risk scores of the geographic regions.

21. The medium of claim 20, wherein:
the machine learning model comprises a directed cyclic graph of perceptions; and
training the machine-learning model comprises computing partial derivatives of perceptron weights of the machine-learning model with respect to an objective function that is based on differences between predictions of the machine-learning model and the historical geolocation-pathogen-risk scores.

22. The medium of claim 1, the operations further comprising training a machine learning model to allocate risk of geographic regions to places of interest by iteratively determining splits of multiple dimensions in an input feature space that includes the first data with a greedy optimization that minimizes a measure of entropy on each side of the splits, the input feature space having more than five dimensions.

23. The medium of claim 22, wherein:
the machine learning model segments the input feature space into different volumes corresponding to different weights; and
allocation risk of geographic regions to places of interest within those geographic regions based on at least some of the first data comprises:
obtaining weights for the places of interest within those geographic regions;
normalizing, within each of the geographic regions, the weights of the places of interest in the respective geographic regions to form coefficients, such that the coefficients in a given geographic region sum to 1 or less; and
multiplying the geolocation-pathogen-risk scores of the regions by the coefficients corresponding to places of interest in the respective geographic regions to allocate risk of geographic regions to places of interest within those geographic regions.

24. The medium of claim 1, the operations comprising:
obtaining a starting geolocation and a stopping geolocation of a traveler;
accessing geolocation-pathogen-risk scores of the starting geolocation and the stopping geolocation; and
causing a user interface to be presented that indicates one or more indicia of risk corresponding to the geolocation-pathogen-risk scores of the starting geolocation and the stopping geolocation.

25. The medium of claim 1, the operations further comprising:
obtaining a passenger manifest for a transit of a vehicle;
based on the passenger manifest, accessing a history of geolocations visited by the travelers identified by the manifest;
accessing geolocation-pathogen-risk scores of the geolocations visited by the travelers; and
determining a transit-pathogen-risk score of the transit based on the geolocation-pathogen-risk scores of the geolocations visited by the travelers.

26. The medium of claim 1, the operations further comprising:
causing a user interface to be presented with a map of a geographic extent;
receiving a user input defining a bounding polygon of an area within the geographic extent;
accessing geolocation-pathogen-risk scores of geolocations within the bounding polygon; and
causing a heat map to be presented in the user interface with color indicating geolocation-pathogen-risk scores of geolocations within the bounding polygon.

27. The medium of claim 26, the operations further comprising:
receiving a user selection in the user interface of a given geolocation within the bounding polygon; and
in response, causing the user interface to present a trend chart depicting variation over time of the geolocation-pathogen-risk score of the given geolocation.

28. The medium of claim 1, the operations further comprising:
obtaining sequences of geolocations of a plurality candidate paths to be traveled by goods in supply chain or a person;
accessing geolocation-pathogen-risk scores of the geolocations of the candidate paths;

determining path-pathogen-risk scores of the candidate paths based on the geolocation-pathogen-risk scores of the geolocations of the candidate paths; and selecting a path from among the candidate paths based on the path-pathogen-risk scores.

29. The medium of claim 1, wherein:

allocating risk is performed with a machine learning model trained to allocate risk of geographic regions to places of interest within those geographic regions based on at least some of the first data;

the first data is static data;

the second data is dynamic data;

at least some of the geographic regions are reporting districts;

at least some of the places of interest are smaller than 1,000 square meters;

the geolocation-pathogen-risk scores of the places of interest and the geolocation-pathogen-risk scores of the geographic regions are specific to the corresponding geolocations and are independent of potential visitors to those corresponding geolocations;

the static data includes census data updated once per decade;

the dynamic data includes amounts of infections or deaths attributable to a given pathogen in the geographic regions updated at least daily;

the second data includes anonymized movement transactions each both corresponding to a movement of a person between geolocations and including starting and ending geographic coordinates;

determining geolocation-pathogen-risk scores of the places of interest comprises determining amounts of people visiting the places of interest during designated windows of time based on the movement transactions;

the movement transactions are obtained without having server-side access to personally identifiable information of the people undergoing the corresponding movements and based on geolocations sensed by mobile computing devices carried by the people undergoing the corresponding movements;

movement transactions are obtained without having server-side access to pseudonymous identifiers of the people undergoing the corresponding movements by which movement transactions by the same person are correlatable;

determining amounts of people visiting the places of interest comprises:

obtaining a latitude and longitude coordinate of an ending location of a given movement transaction among the anonymized movement transactions;

truncating digits of the latitude and longitude coordinates less significant than a threshold position to form truncated coordinates;

determining an identifier of a grid square from the truncated coordinates;

using the identifier of the grid square as a pointer to a set of geolocations in the grid square; and computing, for at least some of the set of geolocations in the grid square, point-in-polygon algorithm results based on the latitude and longitude coordinate, using more significant digits than are present in the truncated coordinates, without computing point-in-polygon algorithm results based on the latitude and longitude coordinate for geolocations in other grid squares;

the geographic information system stores more than 100,000 geolocations, each designated with a corresponding polygon having latitude and longitude coordinates as vertices;

less than 0.01% of the geolocations are analyzed with the point-in-polygon algorithm to determine whether the given movement transaction indicates a visit, thereby reducing worst-case run-time computational complexity by more than three orders of magnitude relative to systems that analyze every one of the 100,000 geolocations to determine which are visited;

at least some of the geolocations are individual floors of a multi-story building, each of at least of a plurality of the floors corresponding to a different geolocation for which a respective geolocation-pathogen-risk score is determined; and the operations further comprise:

obtaining a geolocation to be visited by a person;

obtaining a record indicative of that person's compliance with previous behavior modification messaging regarding pathogen risk;

determining a risk modifier score based on the record;

modifying at a geolocation-pathogen-risk score corresponding to the geolocation to be visited by the person with the risk modifier score to form a personalized geolocation-pathogen-risk score, wherein failures to respond to comply with previous behavior modification messaging regarding pathogen risk causes the personalized geolocation-pathogen-risk score to indicate more risk;

determining that the personalized geolocation-pathogen-risk satisfies a threshold;

in response, causing a message to be presented to the person via the person's mobile computing device, wherein the record and the personalized geolocation-pathogen-risk score are updated more frequently than the geolocation-pathogen-risk score for more than 1,000,000 people;

performing active learning with the machine learning model as new instances of the second data are obtained over time, wherein the second data is time-series data;

obtaining a set of facilities of an organization, each of the facilities being at different geolocations;

obtaining a set of people who visit or are predicted to visit the facilities;

obtaining, for each of at least some members of the set of people, associated geolocations, at least some of the associated geolocations being geolocations including residences of respective members of the set or people or places the respective members of the set of people have previously visited;

accessing, for each member of the set of people who visit or are predicted to visit the facilities, the geolocation-pathogen-risk scores of the associated geolocations;

determining geolocation-pathogen-risk scores, or modified geolocation-pathogen-risk scores, of the facilities based on the geolocation-pathogen-risk scores of the associated geolocations;

determining subsets of the set of people based on the geolocation-pathogen-risk scores of their associated geolocations, wherein obtaining the set of people and obtaining the associated geolocations comprises querying a payroll or identity management service of the organization to obtain residential addresses of employees of the organization;

causing a message to be sent to computing devices of one of the subsets having the most severe geolocation-pathogen-risk score among the subsets, the message instructing the members of the one of the subsets to not visit the facilities;

causing a user interface to be presented showing color-coded representations of the facilities with colors indicating the geolocation-pathogen-risk scores of the facilities;

exposing an application program interface by which third party computing services interrogate the geolocation-pathogen-risk scores of at least some of the places of interest to inform product or service recommendations involving activities at the least some of the places of interest;

accessing historical geolocation-pathogen-risk scores of the geographic regions in memory;

training another machine learning model to predict geolocation-pathogen-risk scores based on the historical geolocation-pathogen-risk scores; and determining, based on the trained another machine learning model, features of the first data that correlate with changes in the historical geolocation-pathogen-risk scores of the geographic regions, wherein:

the another machine learning model comprises a directed cyclic graph of perceptions;

training the another machine-learning model comprises computing partial derivatives of perceptron weights of the another machine-learning model with respect to an objective function that is based on differences between predictions of the another machine-learning model and the historical geolocation-pathogen-risk scores;

training the machine learning model trained to allocate risk of geographic regions to places of interest by iteratively determining splits of multiple dimensions in an input feature space that includes the first data with a greedy optimization that minimizes a measure of entropy on each side of the splits, the input feature space having more than five dimensions, wherein:

the machine learning model segments the input feature space into different volumes corresponding to different weights; and allocation risk of geographic regions to places of interest within those geographic regions based on at least some of the first data comprises:

obtaining weights for the places of interest within those geographic regions;

normalizing, within each of the geographic regions, the weights of the places of interest in the respective geographic regions to form coefficients, such that the coefficients in a given geographic region sum to 1 or less; and multiplying the geolocation-pathogen-risk scores of the regions by the coefficients corresponding to places of interest in the respective geographic regions to allocate risk of geographic regions to places of interest within those geographic regions;

obtaining a starting geolocation and a stopping geolocation of a traveler;

accessing geolocation-pathogen-risk scores of the starting geolocation and the stopping geolocation;

causing the user interface to be presented that indicates one or more indicia of risk corresponding to the geolocation-pathogen-risk scores of the starting geolocation and the stopping geolocation;

obtaining a passenger manifest for a transit of a vehicle;

based on the passenger manifest, accessing a history of geolocations visited by the travelers identified by the manifest;

accessing geolocation-pathogen-risk scores of the geolocations visited by the travelers; and determining a transit-pathogen-risk score of the transit based on the geolocation-pathogen-risk scores of the geolocations visited by the travelers;

causing the user interface to be presented with a map of a geographic extent;

receiving a user input defining a bounding polygon of an area within the geographic extent;

accessing geolocation-pathogen-risk scores of geolocations within the bounding polygon;

causing a heat map to be presented in the user interface with color indicating geolocation-pathogen-risk scores of geolocations within the bounding polygon;

receiving a user selection in the user interface of a given geolocation within the bounding polygon;

in response, causing the user interface to present a trend chart depicting variation over time of the geolocation-pathogen-risk score of the given geolocation;

obtaining sequences of geolocations of a plurality candidate paths to be traveled by goods in supply chain or a person;

accessing geolocation-pathogen-risk scores of the geolocations of the candidate paths;

determining path-pathogen-risk scores of the candidate paths based on the geolocation-pathogen-risk scores of the geolocations of the candidate paths; and selecting a path from among the candidate paths based on the path-pathogen-risk scores.

30. A method, comprising:

obtaining, with a computer system, a plurality of geolocations from a geographic information system, the plurality of geolocations including both geolocations that are geographic regions and geolocations that are places of interest within those geographic regions;

obtaining, with the computer system, first data about at least some of the plurality of geolocations, wherein:
the first data is updated less frequently than a first rate, and
the first data is not pathogen specific;

obtaining, with the computer system, second data about at least some of the plurality of geolocations, wherein:
the second data is updated more frequently than a second rate that is more frequent than the first rate, and
the second data is pathogen-specific;

determining, with the computer system, geolocation-pathogen-risk scores of the geographic regions based on both the first data and the second data;

determining, with the computer system, geolocation-pathogen-risk scores of the places of interest by allocating risk of geographic regions to places of interest within those geographic regions based on at least some of the first data, such that at least some places of interest in the same geographic region have different geolocation-pathogen-risk scores; and storing, with the computer system, the geolocation-pathogen-risk scores of the places of interest and the geolocation-pathogen-risk scores of the geographic regions in memory.

* * * * *